(12) United States Patent
Windhab et al.

(10) Patent No.: US 6,664,071 B1
(45) Date of Patent: Dec. 16, 2003

(54) PHOTODETECTOR AND THE USE OF THE SAME

(75) Inventors: Norbert Windhab, Hattersheim (DE); Hans-Ulrich Hoppe, Langenbach (DE); Donald Lupo, Dublin (IE)

(73) Assignee: Nanogen Recognomics GmbH (DE)

( * ) Notice: Subject to any disclaimer, the term of this patent is extended or adjusted under 35 U.S.C. 154(b) by 0 days.

(21) Appl. No.: 09/622,956

(22) PCT Filed: Feb. 25, 1999

(86) PCT No.: PCT/EP99/01206

§ 371 (c)(1),
(2), (4) Date: Sep. 26, 2000

(87) PCT Pub. No.: WO99/45595

PCT Pub. Date: Sep. 10, 1999

(30) Foreign Application Priority Data

Mar. 3, 1998 (DE) .......................... 198 08 936

(51) Int. Cl.[7] .................. G01N 33/533; G01N 33/534; G01N 33/535; G01N 33/553; C12N 11/14; C12N 11/02; H01L 27/00

(52) U.S. Cl. .............. 435/7.94; 257/43; 257/635; 257/642; 257/644; 435/7.91; 435/6; 435/40.5; 435/40.52; 435/176; 435/177; 435/180; 435/808; 436/172; 436/525; 436/544; 436/545; 436/546; 436/805

(58) Field of Search .................. 436/525, 544, 436/545, 172, 546, 805; 136/263, 255; 257/40, 43, 635, 642, 644; 435/7.91, 7.94, 6, 40.5, 40.52, 177, 176, 180, 808

(56) References Cited

U.S. PATENT DOCUMENTS

| | | | |
|---|---|---|---|
| 4,786,813 A | 11/1988 | Svanberg et al. | 250/461.1 |
| 5,062,942 A | 11/1991 | Kambara et al. | 204/299 |
| 5,334,856 A | 8/1994 | Otsuka et al. | 257/40 |
| 5,384,764 A | 1/1995 | Nordal | 369/275.1 |
| 5,683,833 A | 11/1997 | Häussling et al. | 429/192 |
| 5,858,668 A | 1/1999 | Neuenhofer et al. | 435/6 |
| 5,885,368 A | * 3/1999 | Lupo et al. | |

FOREIGN PATENT DOCUMENTS

| | | |
|---|---|---|
| DE | 2164725 | 7/1972 |
| DE | 4306407 | 9/1994 |
| DE | 19534122 | 3/1997 |
| EP | 0718858 | 12/1994 |
| WO | 96/31909 | 10/1996 |
| WO | 97/10617 | 3/1997 |

* cited by examiner

Primary Examiner—Mary E. Ceperley
(74) Attorney, Agent, or Firm—Connolly Bove Lodge & Hutz LLP

(57) ABSTRACT

A device for the detection of electromagnetic radiation, wherein the device has
  (i) a photoactive layer of a semiconductor having a band gap of greater than 2.5 eV,
  (ii) a dye applied to the semiconductor, and
  (iii) a charge transport layer comprising a hole conductor material, where the hole conductor material is preferably solid and amorphous.

24 Claims, 11 Drawing Sheets

PHOTODETECTOR AND THE USE OF THE SAME

BACKGROUND OF THE INVENTION

1. Field of the Invention

The invention relates to an opto-electronic detector for the qualitative and quantitative determination of electromagnetic radiation, in particular visible radiation. It furthermore relates to a structured matrix of opto-electronic detectors, to arrangements for optical data storage and reading, and to sensor elements and arrangements for immunodiagnostics and DNA analysis.

2. Description of the Prior Art

Specifically, the invention relates to a photodetector, or a matrix of photo-detectors, whose particular use is in the area of detection of labeled or non-labeled chemical substances for quantitative or qualitative diagnostics, for quality assurance or for chemical analysis.

Such detectors are preferably used where the occurrence, the intensity and the wavelength of electromagnetic radiation, in particular visible and near infra-red radiation, is to be determined, the radiation preferably having a wavelength in the range from 400 to 1000 nm, particularly preferably from 400 to 700 nm, very particularly preferably from 450 to 700 nm.

Typical detectors for visible radiation are Si or Ge photodiodes, CdS or CdSe photoconductivity detectors, and vacuum photodiodes and photo-multipliers. Such detectors and their use are described in "Building Scientific Instruments" (J. Moore, C. Davis and M. Coplan, London: Addison-Wesley, 1983).

A special application is the specific detection of biologically relevant molecules by so-called "molecular recognition reactions", such as immuno-diagnostics or gene probe techniques. These methods are known to the person skilled in the art (Lit C. Kessler (Ed.) *Nonradioactive Labeling and Detection of Biomolecules*, Springer-Verlag Berlin, Heidelberg 1192): these include, in particular: immunoassays (determination of metabolites, hormones, DNA, proteins, viruses, environmental toxins, etc.), DNA fingerprinting, DNA sequencing, nucleic acid hybridization assay; Northern blotting, reporter gene assay, Southern blotting, Western blotting, peptide or allergen arrays, combinatorial arrays (arrays are fields or matrices) and the investigation of tissue samples, microsections, and living cells stained directly (dye) or indirectly (for example dye conjugates with antibodies) or immobilized on the surface, cell organelle or in the cell interior ("cell lawns") or cell constituents.

In a simple, specific example, a molecule (for example an antibody, an antigen, an anti-antibody, or a fragment of the above) which is complementary (i.e. adheres specifically) to the molecule to be recognized is, to this end, chemically labeled by means of chemiluminescent substrates or chemiluminescent catalysts (for example enzymes). These labels can be utilized to amplify the signal, since, for example, enzyme reactions can, through high conversion, supply a multiple of photons per bound enzyme or bound molecule.

Other methods utilize substrates which manifest themselves in a color reaction, i.e. can be measured through the specific absorption of a light beam through shadowing at the detector.

FIG. 1 describes an illustrative diagram of a selective immunotest in sandwich arrangement. The soluble antigen (13) binds selectively to the immobilized antibody I (14), and a soluble antibody II (12) is specific for the same antigen and is bound to an enzyme (11). The products (17) of the enzyme-catalyzed reaction (18) can be detected directly (chemiluminescence) or indirectly (fluorescence, scintillation proximity, colorimetric shadowing) by the detector described here (16). In the case of a position-resolving detector, further tests can be carried out simultaneously with the same sample, such as, for example, antibody III (19), which, in the example, has not bound any antigen which selectively binds to it. Other (especially ELISA) tests with and without immobilization techniques are conceivable (cf. also A. M. Campbell "Monoclonal antibody and immuno-sensor technology", Elsevier, Amsterdam, 1991).

Fluorescence chromophores, which, due to excitation, emit light having a different wavelength, and radioactive labels, which, in the scintillation proximity assay, apply a radioactive label in the molecular vicinity of a scintillation dye in the event of binding, are amongst the most sensitive methods, since the energy which generates the signal at the detector is not identical with the excitation energy. All these methods emit light having a very precisely defined wavelength.

If a molecule is recognized in a localized manner, qualitative and/or quantitative detection takes place by measurement of the light absorption or emission. The detection limits for such systems are in the molecular range; large dynamics, i.e. a quantitative statement over many orders of magnitude of the analyte concentrations, is often necessary. For analysis of tissue samples or blotting techniques, and for analysis of electrophoresis gels, and for every miniaturization and parallelization of an analytical instrument, position resolution in an arrangement which can be structured as desired is desirable. These requirements are satisfied to a very particular extent by the detector described here (Bullock, Petrusz, Techniques in Immunochemistry, Acad. Press 1982).

The commercially available instruments are large, expensive or not suitable as "field instrumentation". They use complex photomultipliers or cooled vacuum or CCD cameras. A particularly advantageous embodiment for diagnostic application is a portable diagnosis system or one which can be connected to conventional personal computer stations. With respect to the risk of cross-contamination in the case of analysis robots, the disposable detector analysis kit is recommended. With regard to very sensitive diagnosis samples which basically require fast, direct analysis at the site of sampling owing to stability problems, the risk of contamination and a restriction to the amount of sample, miniaturization is necessary.

However, miniaturization of the known optical methods comes up against feasibility limits (cf. A. M. Campbell "Monoclonal antibody and immuno-sensor technology", Elsevier, Amsterdam, 1991).

Only a limited number of semi-quantitative, convenient test systems are known which allow "field analysis" of this type without further technical complexity, for example after color reactions directly on a color location scale.

U.S. Pat. No. 5,384,764 describes a device for optical data storage which comprises a storage medium into which holes can be burnt by writing by means of a light source and later read out as information, wherein a matrix of microlenses is positioned in the spatial vicinity of the storage medium for imaging purposes. However, the invention contains no details of a detector matrix or any teaching regarding inexpensive production of an integrated component.

The journal c't, issue March/1998, p. 18, describes a component for optical data storage which consists of a light-generating layer of a polymer, a switchable storage layer of a protein and a detector layer of a second polymer, and also a network of crossed electrodes. The color of the protein layer can be switched through the electroluminescence of a pixel defined by the crossing of two electrodes, so that on reading the same pixel, the intensity of the light penetrating into the corresponding photodetector pixel is changed.

For applications in sensor technology, diagnostics and DNA analysis and in optical data storage, it is advantageous for a matrix to be produced from small photodetectors. Vacuum photodiodes and photomultipliers can have high sensitivity, but are unsuitable for the production of matrices comprising a large number of small detectors. Conventional solid-state photodetectors can be converted into matrices, and photodiode arrays and CCD cameras are known. However, these products are too expensive for many of the above-described applications, in particular for disposable elements. Polymeric detectors, as described in c't, can be produced inexpensively, but their sensitivity is limited; furthermore, the possibility of determining the absorption wavelength is limited in such detectors.

There is therefore a necessity to develop detectors which can be produced as a matrix at low cost and which can be optimized for maximum sensitivity in various wavelength ranges.

DE-A 43 06 407 describes a detector for checking the wavelength range of electromagnetic radiation which has a photoactive layer produced from titanium dioxide of high porosity. A liquid electrolyte as charge-transport medium and a dye are embedded in the photoactive layer, the dye being selected in such a way that it can be excited by electromagnetic radiation of a defined wavelength.

However, the use of an electrolyte liquid is basically disadvantageous since it is associated with problems, for example with leaking of the cell and photocorrosion. This disadvantage becomes particularly severe if a matrix of small, mutually separated photodetectors is to be produced at a low price.

The invention therefore has the object of providing a detector with which the occurrence and the wavelength of electromagnetic radiation can be determined in a simple manner and in addition quantitatively.

PCT/EP96/03944 describes a photovoltaic cell which comprises a hole conductor material. In a particular embodiment of the cell, it comprises a photoactive layer produced from a semiconductor having a high band gap, for example greater than 2.5 or 3 eV, with high porosity, in which a solid, amorphous hole conductor as charge-transport medium and a dye as light-absorbing element are embedded. Such photovoltaic cells are suitable for the production of electrical energy from light at relatively high intensity, but are not employed for detecting radiation of low intensity.

SUMMARY OF THE INVENTION

It has now been found, surprisingly, that photodetectors can also be produced with a solid amorphous hole conductor material as charge-transport layer. Such photodetectors are particularly advantageous if they have a photoactive layer produced from at least one semiconductor having a high band gap, preferably above 2.5 to 3 eV, with high porosity, in which a solid, amorphous hole conductor as charge-transport medium and a dye as light-absorbing element are embedded, the dye being selected in such a way that it can be excited by electromagnetic radiation of a defined wavelength.

The invention therefore relates to an opto-electronic radiation detector which has a photoactive layer produced from at least one semiconductor having a high band gap, preferably above 3 eV, with high porosity, in which a solid, amorphous hole conductor as charge-transport medium and a dye as light-absorbing element are embedded. Particular preference is given to detectors of this type in which the semiconductor is a metal oxide, very particularly preferably those containing titanium oxide.

The invention furthermore relates to a matrix of photodetectors according to the invention.

The invention furthermore relates to an element for optical data storage which comprises a matrix of detectors according to the invention.

The invention furthermore relates to sensor elements, immunoassay elements and DNA analysis elements which comprise a detector matrix according to the invention, and also to sensor, immunoassay and DNA analysis devices wherein a sensor element, immunoassay element or DNA analysis element is read by a reading device comprising a detector matrix according to the invention.

The invention therefore furthermore relates to chemical analysis systems constructed using the specific detector system, for environmental quality analysis, preferably in the foods area, in crop protection and very particularly preferably in human and animal medical diagnostics: for example as immunoassays for the preferential determination of metabolites, hormones, DNA, proteins, viruses, environmental toxins, as instruments for carrying out DNA fingerprinting, DNA sequencing, nucleic acid hybridization assay, Northern blotting, reporter gene assay, Southern blotting, Western blotting, peptide or allergen arrays and the investigation of tissue samples, microsections, and living cells stained directly (dye) or indirectly (for example dye conjugates with antibodies) or immobilized on the surface, cell organelle or in the cell interior ("cell lawns") or cell constituents. Matrix systems of this type are also known as biochips.

The invention relates to analytical systems in which the sensitizer dye can be customized to the particular system.

The invention also relates to a detector whose dynamics can be adapted through choice of the suitable measurement mode, for example by measurement of the photovoltage.

The invention relates to a detector system with preference for the analysis of tissue samples, for blotting techniques or for the analysis of electrophoresis gels which achieves position resolution through miniaturization and parallelization and can be structured in any desired manner.

The invention relates to analysis systems of the type described which are small, convenient and inexpensively suitable as "field instrumentation" and particularly preferably can be connected to conventional personal computer stations.

The invention very particularly relates to disposable detector analysis kits in accordance with the principle described.

The invention still further relates to elements and devices in which the optical signal to be measured is generated by chemiluminescence.

However, the invention also relates to elements and devices in which the optical signal to be measured arises through fluorescence or phosphorescence, these arising through excitation by a light source located in the element or device, preferably a planar light source, particularly preferably a light-emitting film, very particularly preferably a light-emitting film comprising an organic or polymeric compound as illuminant.

DETAILED DESCRIPTION OF THE INVENTION

Due to the absence of an electrolyte, no problems with photocorrosion, for example, occur in the detector according to the invention. Owing to the lack of liquid components, the production of a matrix of small photodetectors presents no problems. Since virtually all production steps can be carried out using printing processes, expensive photolithographic steps for the production of a detector matrix can be reduced to a minimum. The detectors can be structured virtually as desired by printing processes in order to optimize them for the desired light signal geometries to be measured. They can be applied to transparent or reflective substrates, also to rigid or very thin, flexible substrates. The photocurrent and photovoltage occur even at low light intensities and enable direct measurement of the signal without external current and voltage supply; this enables use in disposable sensors, in which an external supply would be too expensive. Through the choice of a suitable measurement mode, for example through measurement of the photovoltage, signals can be detected quantitatively over many orders of magnitude.

Figure 2:
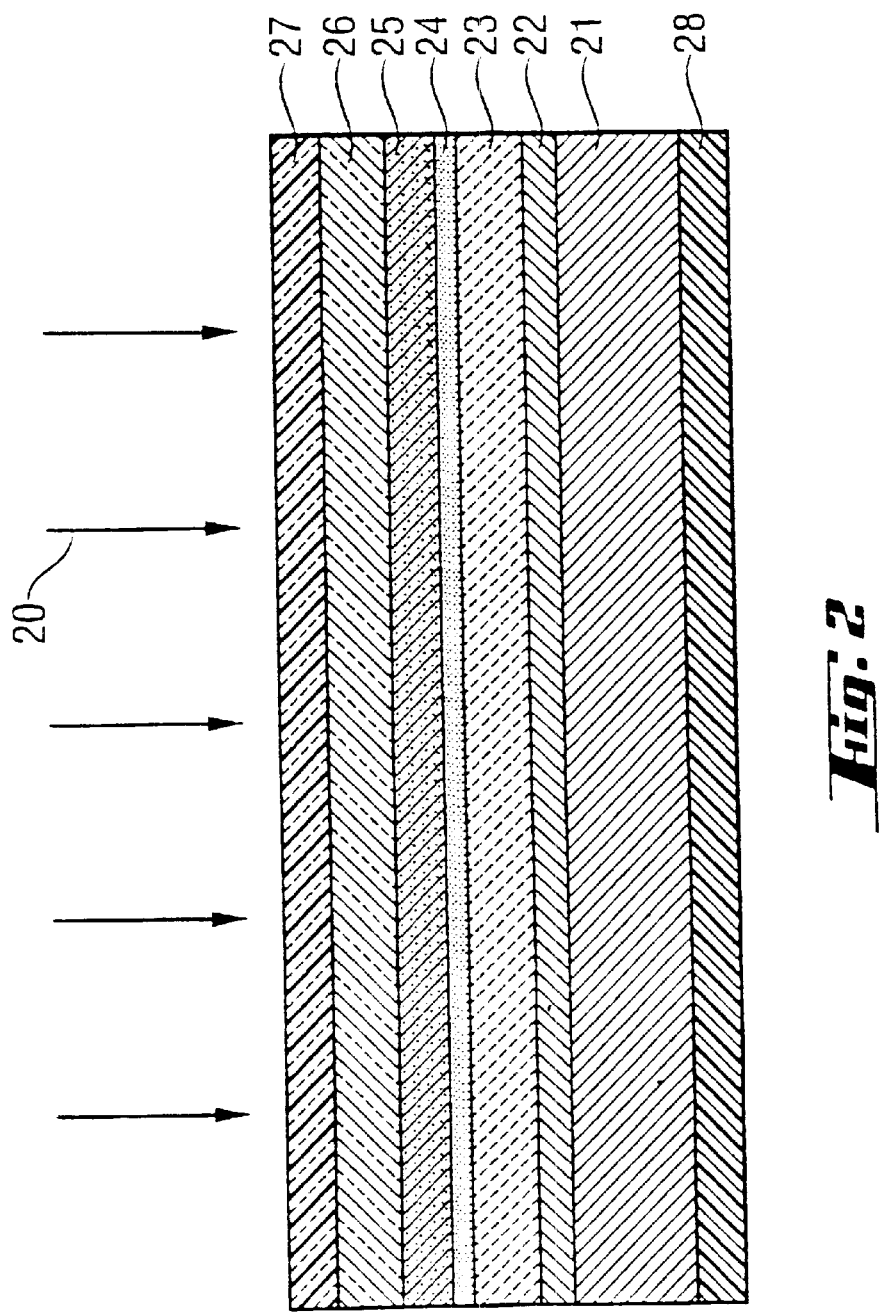
FIG. 2 illustrates a preferred detector according to the invention.

The detector according to the invention exhibits broad sensitivity. Through the targeted use of certain dyes, the selective action spectrum can be customized to the particular system. FIG. 2 shows a preferred embodiment of the detector according to the invention (not to scale). A conductive layer 22, which serves as electrode or contact and consists, for example, of a metal, such as Ti, or a metal oxide, such as fluorine-doped tin dioxide or indium-tin oxide (ITO), is applied to a support 21. A semiconductor 23, which preferably has a surface having a roughness factor of >1, is applied to the layer 22. A unimolecular layer of a sensitizer dye 24 is located on the surface of the semiconductor. This is followed by a charge-transport layer 25, which, in accordance with the invention, comprises a hole conductor material. It is limited on one side by the counterelectrode 26, which can consist, for example, of a conductive glass, conductively coated plastic, metal, a transparent conductive oxide (TCO) or another conductive, preferably radiation-transparent material. The detector can be delimited on the top and bottom by an insulating layer 27 and 28 respectively (encapsulation). It may contain a lateral border, not shown in the figure, for example a frame of an electrically insulating material, such as plastic or glass. At least one side of the detector must be transparent to the electromagnetic radiation 20 to be detected, so that this can reach the dye. The detector according to the invention additionally contains devices, not shown in the figure, for measuring the voltages, currents or conductivity changes which occur. Such devices are known to the person skilled in the art.

Figure 3:
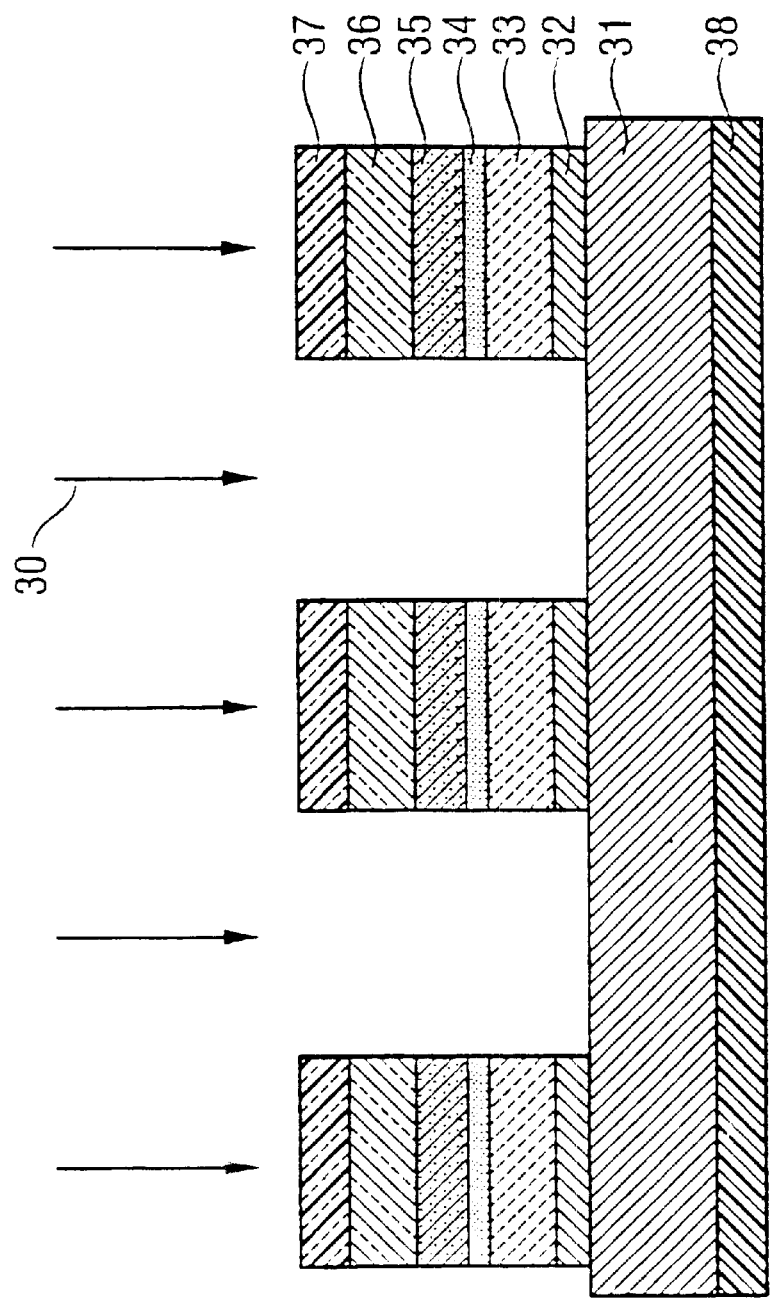
FIG. 3 illustrates another preferred embodiment according to the invention.

FIG. 3 shows another preferred embodiment of the invention. Individual detectors according to the invention with the same structure as the unstructured detector in FIG. 2 are applied to the support 31. In addition, the detector according to the invention contains devices, not shown in the figure, for measuring the voltages, currents or conductivity changes which occur. The detector matrix may be incorporated into a system with imaging optics in order to simplify measurement of the spatial distribution of the electromagnetic radiation (the reference numerals 30 to 38 correspond to the numerals 20 to 28 in FIG. 2).

Figure 4:
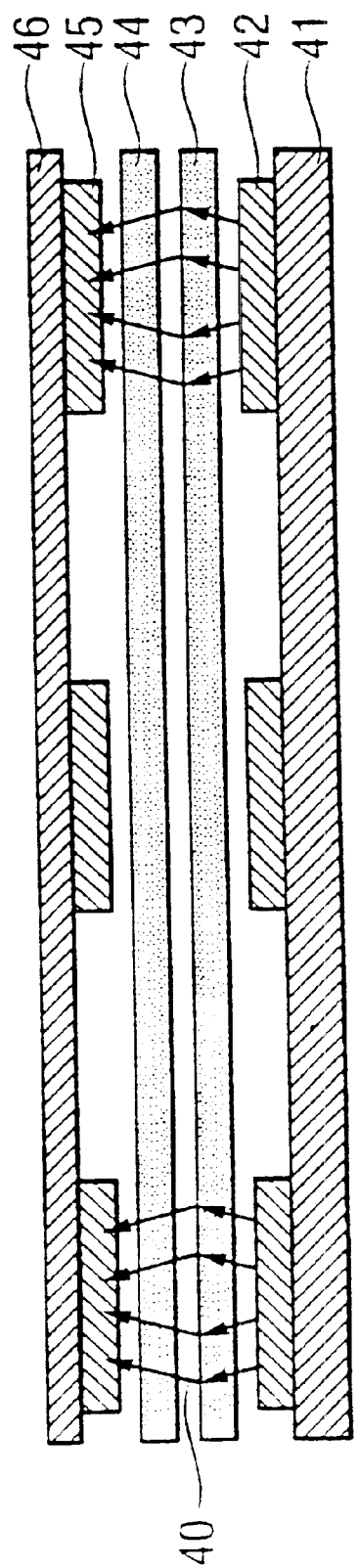
FIG. 4 illustrates a preferred embodiment of a device for optical writing and reading of data according to the invention.

FIG. 4 shows a preferred embodiment of a device for the optical writing and reading of data. A matrix of light sources 42, for example light-emitting diodes, is applied to a support 41. Through an imaging optical system 43, which can be, for example, a lens system, a thin Fresnel lens or a microlens array, the emitted light from the individual light sources is imaged pixel-wise on a data storage medium 44. The storage medium may comprise the following materials, without the invention being restricted thereto: a layer comprising a photochromic dye, a biological storage molecule, such as bacteriorhodopsin, or a light-absorbing layer, into which a hole can be burnt by absorption of light of high intensity. By addressing the light sources at high intensity, data can be written. In order to read the data, the light sources are operated at low intensity. Depending on the switching state of the storage medium, this is transparent or non-transparent to the emitted light from the light sources 42. The intensity of the light 40 transmitted by the storage medium is measured pixel-wise by the detectors 45 according to the invention. The imaging optical system may be located between the light sources and the storage medium, between the storage medium and the detectors or on both sides of the storage medium. In order to increase the sensitivity, the detector support 46 may be provided with a reflective layer, which can also be employed as working electrode.

Figure 5:
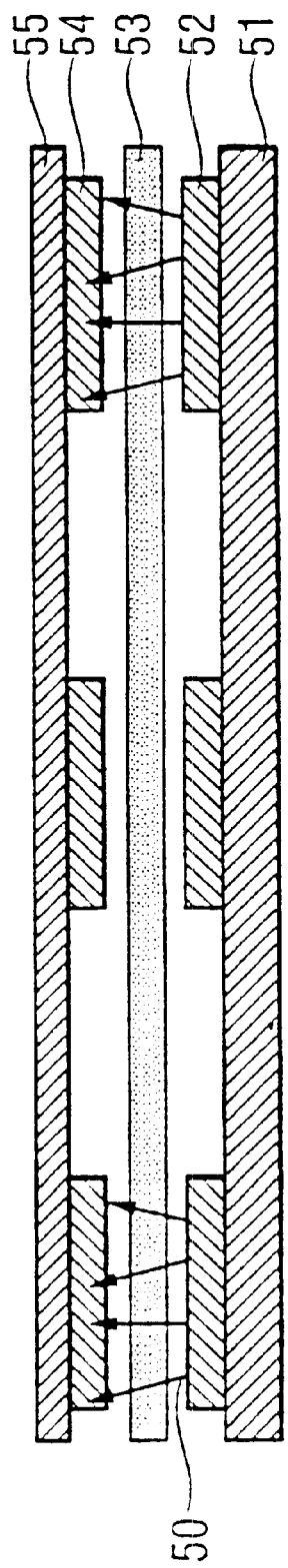
FIG. 5 illustrates another preferred embodiment of the invention for optical data storage.

Another preferred embodiment of the invention for optical data storage is shown in FIG. 5. In this embodiment of the invention, the light sources 52 are arranged on the support 51, the storage medium 53 and the detector 54 arranged on the detector support 55 are so close to one another spatially that the spatial proximity means that the emitted and detected light 50 is measured pixel-wise, and no imaging optical system is necessary to avoid interference from adjacent pixels.

Figure 6:
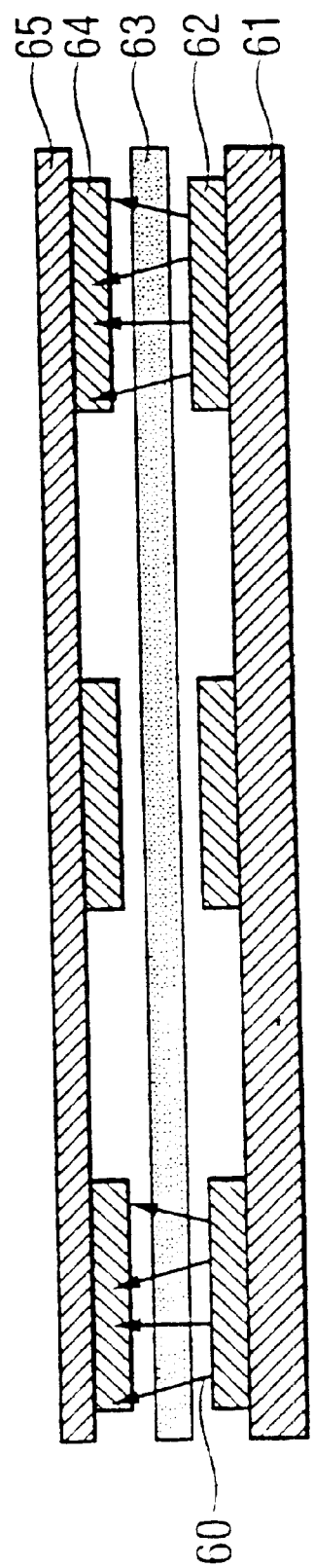
FIG. 6 illustrates a preferred embodiment of the invention in the area of sensor technology, analysis or diagnostics.

A preferred embodiment of the invention in the area of sensor technology, analysis or diagnostics is shown in FIG. 6. A matrix of recognition elements for specific substances, antigens, DNA, etc., is applied to a substrate 61. The sensor element is exposed to a test solution or a test gas. The recognition elements are labeled in such a way that, if the substance to be detected is present, the corresponding pixel illuminates due to chemiluminescence. An optical device 63, which may comprise imaging optics and/or colored filters, may, but need not, be located between the sensor pixels and a matrix of detectors according to the invention applied to the substrate 65. The pixel-wise imaging of the emitted light 60 can be achieved either through an imaging optical system or through the spatial proximity of the emitting and detecting pixels. This sensor matrix may advantageously also have elements 62 and 64, which correspond to elements 52 and 54 in FIG. 5, and filter elements, which are not shown.

Figure 7:
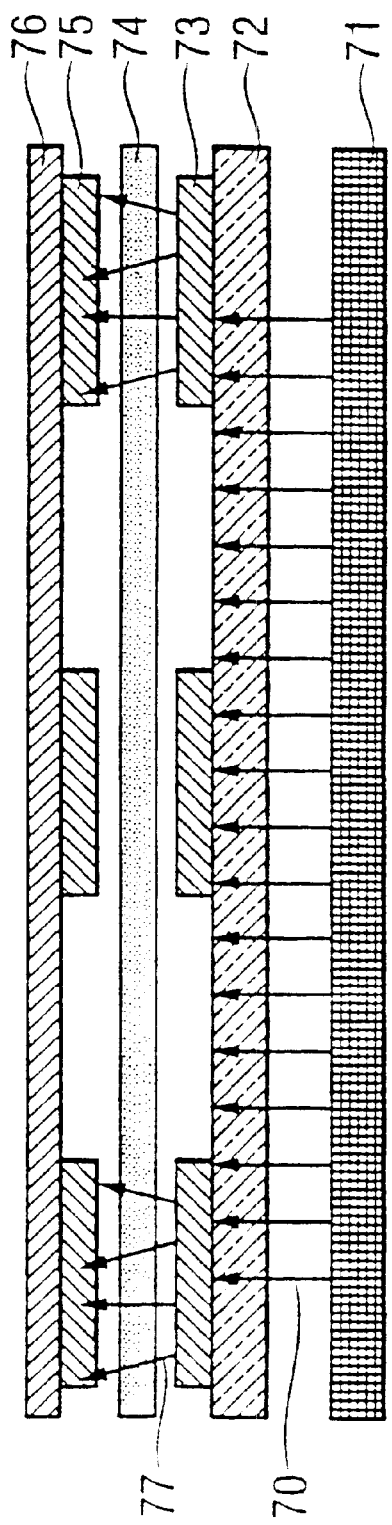
FIG. 7 illustrates another preferred embodiment of the invention for use in sensor technology, analysis and molecular recognition.

FIG. 7 shows another preferred embodiment of the invention for use in sensor technology, analysis, molecular recognition, etc. The matrix of recognition elements 73 applied to a light-transparent support 72 is functionalized in such a way that, on recognition, either the absorption of the light of a certain wavelength is changed or fluorescence or phosphorescence occurs after excitation by a light 70. The light source serving for absorption measurement or luminescence excitation is a two-dimensional light source 71, which may consist of a combination of light source, for example fluorescent tubes or LEDs, plus optical diffuser plate, or of a two-dimensional emitter. Particularly preference is given to illumination systems based on thin-film electroluminescent components, since they result in a more compact construction of the sensor element. Owing to the low operating voltage and the particularly thin construction, two-dimensional light sources comprising organic or polymeric compounds as illuminant are very particularly preferred. Such components are described, for example, in *Ber. Bunsenges. Phys. Chem.* 100, pp. 1667–1677 91996), J. Salbeck, *"Electroluminescence with Organic Compounds"* and the references cited therein. The transmitted or emitted light 77 is measured by the matrix 75 of detectors according to the invention applied to the support 76. An optical device 74, which may comprise imaging optics and/or colored filters, may, but need not, be located between the sensor pixels and the matrix of detectors according to the invention.

Figure 8:
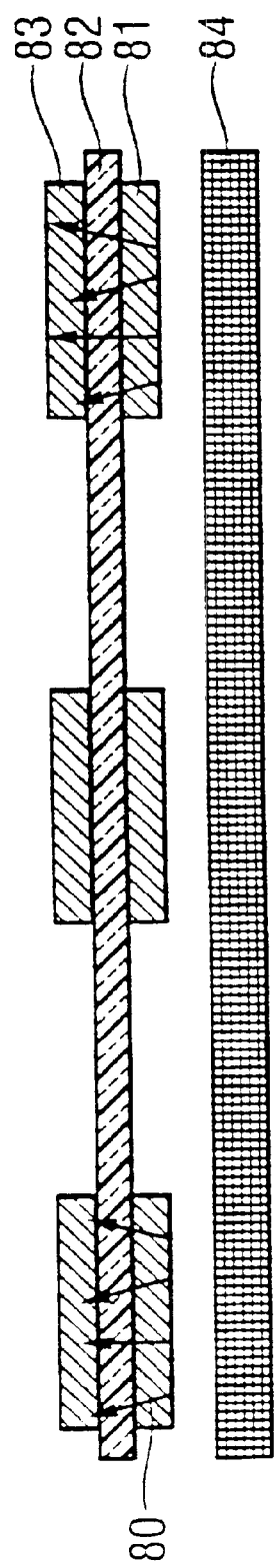
FIG. 8 illustrates a particularly simple embodiment of the invention for use in sensor technology, analysis and molecular recognition.

FIG. 8 shows a particularly simple embodiment of the invention for use in sensor technology, analysis, molecular recognition, etc. The matrix of recognition elements 81 and the matrix of detectors 83 according to the invention are applied to the opposite sides of the same thin light-transparent support 82. The support may, but need not, comprise optical elements, such as colored filters and/or imaging optics, for example microlenses or a Fresnel lens. For applications which require a light source, a two-dimensional light source 84 may optionally be part of the device; this is not necessary for chemiluminesence. The light 80 from the recognition element 81, which must be transparent compared with the support, enters and passes through the support 82 and through a light-transparent working electrode and reaches the corresponding detector 83 according to the invention.

Figure 9:
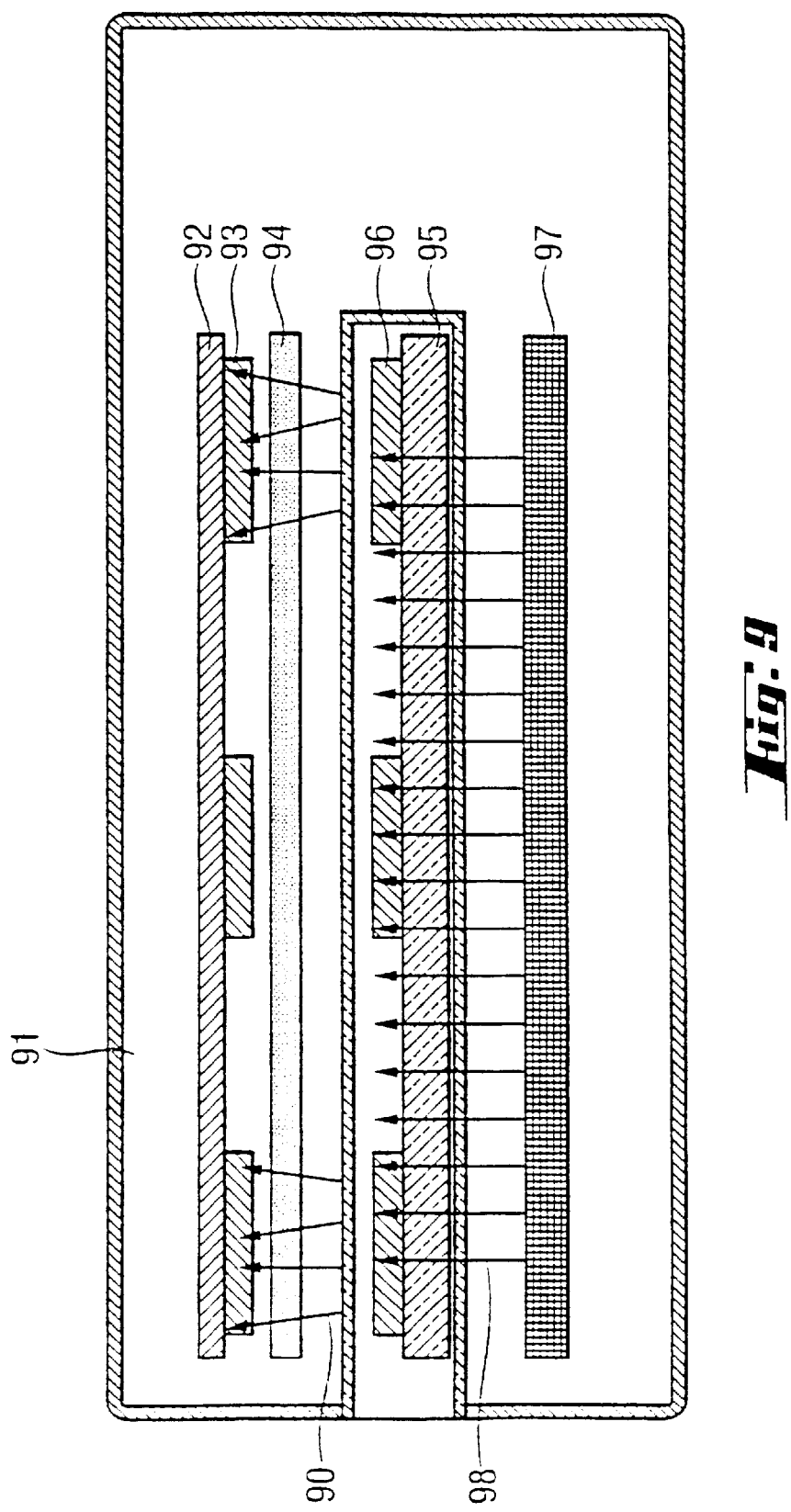
FIG. 9 illustrates another preferred embodiment of the invention for applications in the area of sensor technology, diagnostics and analysis.

FIG. 9 shows another preferred embodiment of the invention for applications in the area of sensor technology, diagnostics, analysis, etc. The matrix 93 of detectors according to the invention, which is applied to a support 92, is incorporated into a small reader 91, which may have a similar size to a portable CD player, a disk drive or a PCMCIA reader. The reader may, but need not, optionally also comprise an optical device 94 and/or a two-dimensional light source 97 which emits excitation or absorption light 98. The matrix 96 of detection elements, which is applied to the support 95, is, after exposure to the test solution or the test gas, pushed into the reader, where the signal is measured pixel-wise by the matrix 93 of detectors in the same manner as described above. The unit may optionally have connections, not shown, to a microcomputer, which can analyze the results and display them on the screen or print them out. It may optionally also contain internal devices, not shown, for the analysis and read-out of the results, for example microprocessors and displays.

Figure 1:
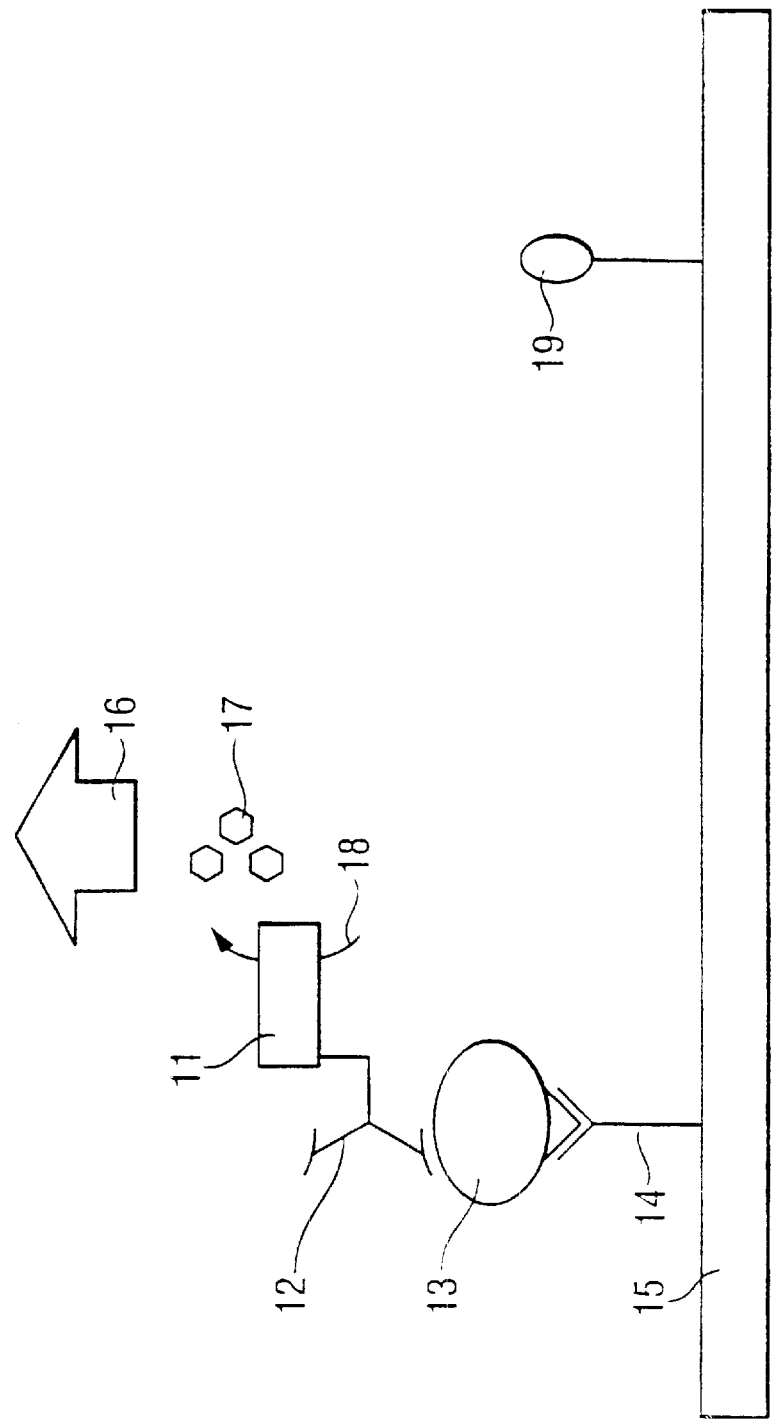
FIG. 1 describes an illustrative diagram of a selective immunotest in a sandwich arrangement.
Figure 10:
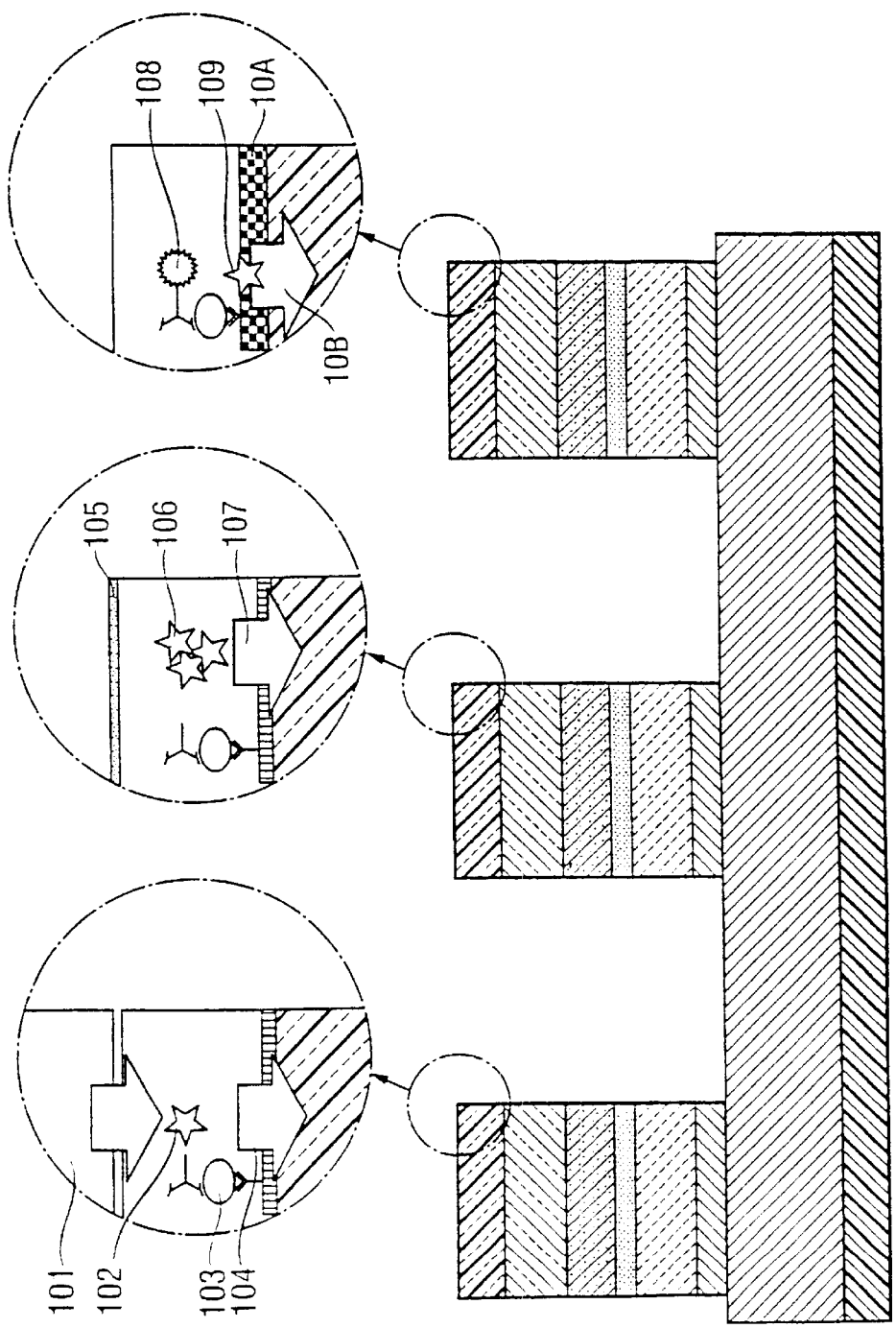
FIG. 10 illustrates three different detection principles according to the invention.

FIG. 10 shows as an example three different detection principles, on the left the calorimetric or fluorimetric case with a laser diode layer (101), from which light is incident on the binding space of the antigen (103), which interacts with the chromophore or fluorophore (102) and emits attenuated light or light of a different wavelength (104), possibly through a filter, to the detector layer. A chemiluminescence case with reflective rear wall (105) is shown in the center of the figure, where, as an example (cf. FIG. 1) in the case of binding, an enzyme which catalyzes the chemiluminescence reaction or cascade (106) is immobilized, and again light is emitted to the detector layer (107). On the right is an example of the scintillation case, in which the antigen-antibody complex is radioactively labeled (108) and a scintillation dye (109) bound in the immobilization zone (10A) is excited and emits light (10B).

Figure 11:
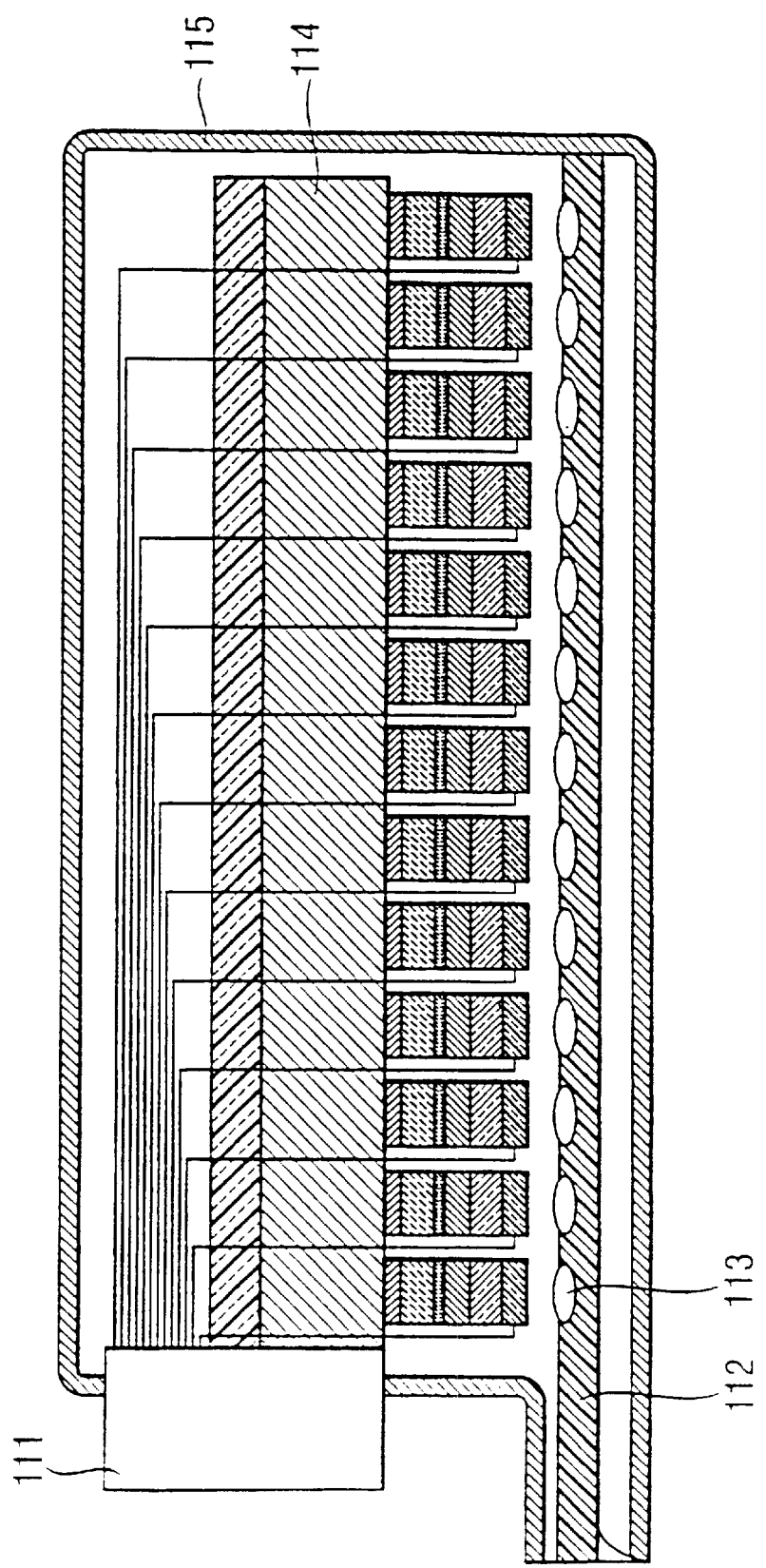
FIG. 11 illustrates how the freely structurable detector support is shaped to give the simplest immunochemiluminescence array.

FIG. 11 shows how the freely structurable detector support (114) is shaped to give the simplest immuno-chemiluminescence array. The array of detector segments, which can be read out independently and simultaneously, corresponds to the binding zones (113) immobilized, for example, on a felt or filter material (112), in which various antibody-antigen complexes can be formed selectively 13. A reaction buffer comprises the substrates, for example for a light-generating chemiluminescence reaction, which, in the event of binding, illuminates the corresponding detector segment. The instrument is accommodated in a convenient housing (115), which has an opening for sample introduction. Integrated measurement electronics (111) display the result.

For the purposes of the invention, the term hole conductor material is taken to mean a conductor material which is able to conduct a positive charge formed by the absence of an electron, with decoupled mass transport and charge transport.

In general, electron-rich, preferably organic compounds which are oxidizable, preferably reversibly, are suitable. It is generally assumed that charge transport in an organic hole conductor material takes place via the formation of free-radical cations.

The oxidation potential here is variable over broad ranges and can be matched to the specific energy level of the semiconductor or sensitizer, for example through the selection of suitable structures. It is preferably above the energy level of the ground state of the dye and below the energy level of the lowest conduction band and thus generally in the region of the band width of the semiconductor, preferably 100–500 mV above the energy level of the ground state).

Preference is given to hole conductor materials in which no mass transport takes place or in which charge and mass transport are fully decoupled. Preference is furthermore given to solid, in particular amorphous hole conductor materials.

The invention therefore also relates to the use of solid amorphous hole conductor materials for the production of charge-transport layers for opto-electronic radiation detectors for the detection of short-wave electro-magnetic radiation.

For the purposes of the invention, it is preferred for the hole conductor layer according to the invention to be prepared in amorphous form, i.e. applied in the amorphous state in the detector according to the invention.

The term "amorphous" serves to describe the state of solid bodies whose molecular units are not arranged in crystal lattices, but instead are arranged irregularly. In contrast to the case in a crystal, in which a close-range order (i.e. constant separations from nearest neighboring atoms) and a long-range order (regular repetition of a base lattice) exist between the atoms, only a close-range order exists in the amorphous state. The amorphous substance has no physically distinguished direction; it is isotropic. All amorphous substances strive for the energetically more favorable crystalline state to a greater or lesser extent. On diffraction of X-rays, electron beams and neutron beams, sharp interference rings as in a crystal do not occur in the case of amorphous solids, but instead only diffuse interference rings at small diffraction angles (halos).

The amorphous state is thus clearly distinguished from the crystalline, liquid or even liquid-crystalline state.

Particular preference is given to hole conductor materials which are soluble in organic solvents and hole conductor materials which can be melted or evaporated. Examples of organic solvents are chloroform, benzene, chlorobenzene, cyclohexanone, toluene, tetrahydrofuran, anisole, cresol, xylene, methyl lactate, methylene chloride, hexane, or other aliphatic, aromatic or alcoholic solvents. It is advantageous for the production of a hole conductor layer according to the invention if the hole conductor material is soluble in an organic solvent or can be melted. For the purposes of the present invention, soluble is taken to mean a solubility of at least 1.0 g/l at 25° C. in an organic or inorganic solvent, preferably in one of the abovementioned solvents.

Preference is furthermore given to hole conductor materials which are able to diffuse into the pores of a rough semiconductor layer owing to their size.

In the case of measurement of a photocurrent, very particular preference is given to hole conductor materials in which the drop in voltage over the hole conductor layer on irradiation with short-wave electromagnetic radiation is <500 mV, preferably <50 mV, particularly preferably <20 mV.

The hole conductor layer generally has a thickness of from 0.1 to 20 μm, preferably from 1 to 15 μm.

Very particular preference is given to Spiro compounds of the general formula (III)

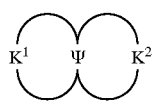

(III)

where ψ can have the following meanings: C, Si, Ge or Sn, preferably C, Si or Ge, particularly preferably C or Si and in particular C; and where $K^1$ and $K^2$, independently of one another, denote conjugated systems. The hole conductor material used is one or more 9,9'-spirobifluorene derivatives of the formula (IV)

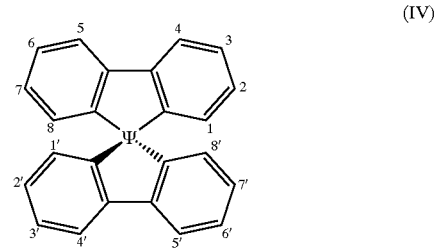

(IV)

Wherein the ψ is defined above and the benzo groups may, independently of one another, be substituted and/or fused. The hole conductor material can also be one or more 9,9'-spirobifluorene derivatives of the formula (I)

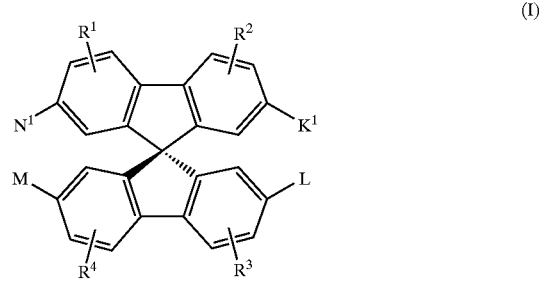

(I)

where the symbols have the following meanings:

$K^1$, L, M, $N^1$, $R^1$, $R^2$, $R^3$ and $R^4$ are identical or different and are a) hydrogen, —$NO_2$, —CN, —F or —Cl, b) a straight-chain or branched alkyl radical having 1 to 20 carbon atoms, where b1) one or more non-adjacent $CH_2$ groups may be replaced by —O—, —S—, —CO—O—, —O—CO—, —O—CO—O—, —$NR^5$— or —Si$(CH_3)_2$—, and/or b2) one or more $CH_2$ groups may be replaced by —CH=CH—, —C≡C—, 1,4-phenylene, 1,4-cyclohexylene or 1,3-cyclopentylene, and/or b3) one or more H atoms may be replaced by F and/or Cl, and/or c) one of the following groups:

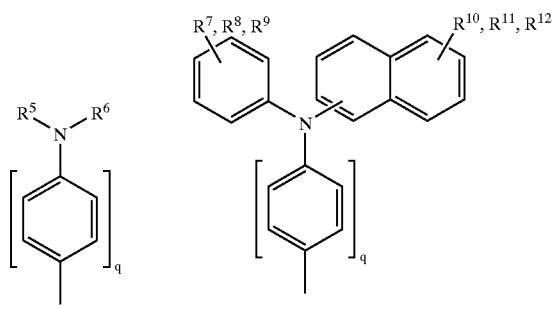
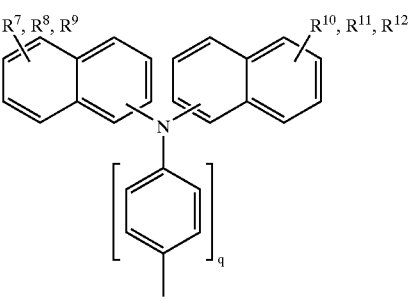
where q=0, 1, 2, 3, 4, 5 or 6
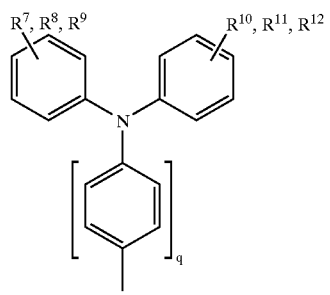
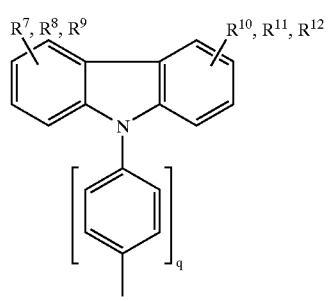
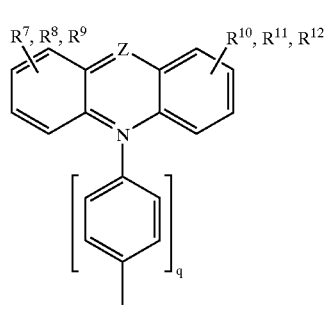
where q=0, 1, 2, 3, 4, 5 or 6
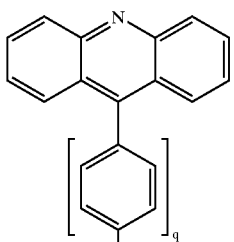
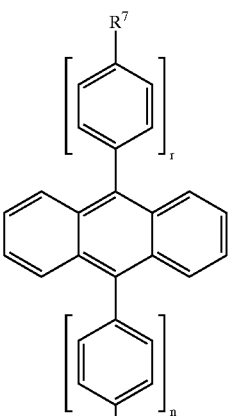
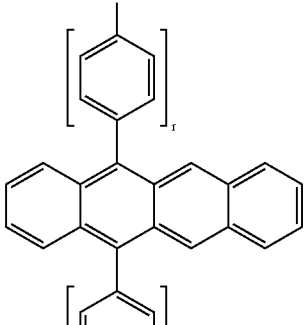
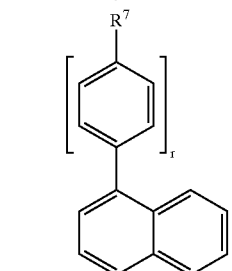
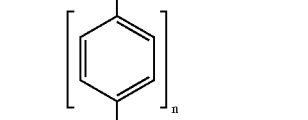
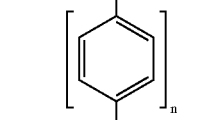
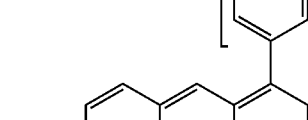
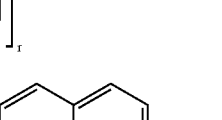
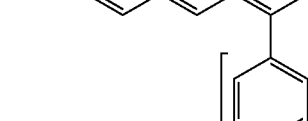
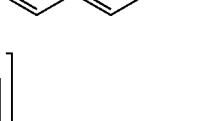
or
d) one of the following groups:
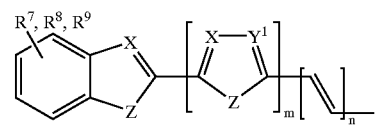
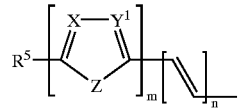

-continued

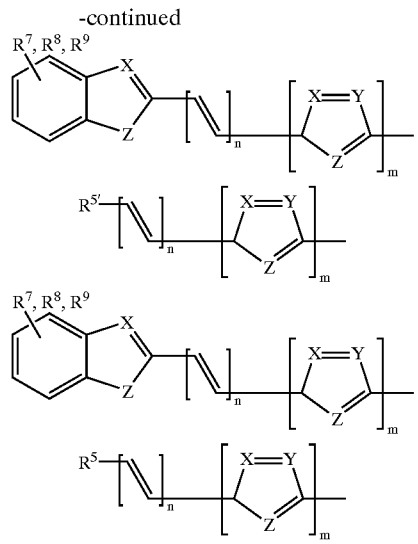

with the proviso that at least one, preferably at least two, of the radicals $K^1$,
L, M, $N^1$, $R^1$, $R^2$, $R^3$ and $R^4$ is one of the groups listed under c);

X and $Y^1$ are, independently of one another, $=CR^7$— or $=N$—;

Z is —O—, —S—, —$NR^5$—, —CRR—, —CR=CR— or —CR=N—;

$R^5$ and $R^6$ are, independently of one another,
a) hydrogen
b) a straight-chain or branched alkyl radical having 1 to 20 carbon atoms, where
b1) one or more non-adjacent $CH_2$ groups which are not bonded to nitrogen may be replaced by —O—, —S—, —CO—O—, —O—CO—, —O—CO—O— or —Si($CH_3$)$_2$, and/or
b2) one or more $CH_2$ groups may be replaced by —CH=CH—, —C≡C—, cyclopropane-1,2-diyl, 1,4-phenylene, 1,4-cyclohexylene or 1,3-cyclopentylene, and/or
b3) one or more H atoms may be replaced by F and/or Cl, and/or
b4) $R^5$ and $R^6$ together may also form a ring;
c) phenyl, biphenyl, 1-naphthyl, 2-naphthyl, 2-thienyl or 2-furanyl;

$R^7$, $R^8$, $R^9$, $R^{10}$, $R^{11}$ and $R^{12}$ are, independently of one another,
a) hydrogen, —CN, —F, —$NO_2$ or —Cl
b) a straight-chain or branched alkyl radical having 1 to 20 carbon atoms, where
b1) one or more non-adjacent $CH_2$ groups may be replaced by —O—, —S—, —CO—O—, —O—CO—, —O—CO—O—, —$NR^5$— or —Si($CH_3$)$_2$—, and/or
b2) one or more $CH_2$ groups may be replaced by —CH=CH—, —C≡C—, cyclopropane-1,2-diyl, 1,4-phenylene, 1,4-cyclohexylene or 1,3-cyclopentylene, and/or
b3) one or more H atoms may be replaced by F and/or Cl;
c) phenyl, biphenyl, 1-naphthyl, 2-naphthyl, 2-thienyl, 2-furanyl, —O-phenyl, —O-biphenyl, —O-1-naphthyl, —O-2-naphthyl, —O-2-thienyl or —O-2-furanyl, m, n, p, q and r are, independently of one another, an integer from 0 to 6, preferably 0, 1, 2, 3 or 4, particularly preferably 0, 1, 2 or 3.

The compounds of the formula (II) are preferably amorphous and are distinguished by high glass transition temperatures.

Preference is given to spirobifluorene derivatives of the formulae (II) a–c

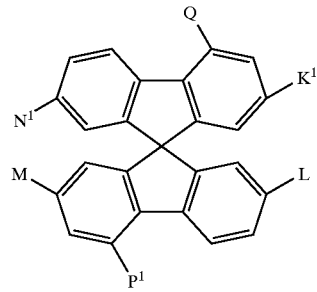

(II)

where the symbols have the following meanings:

II.a) $K^1=L=M=N^1$ and is from the group consisting of:

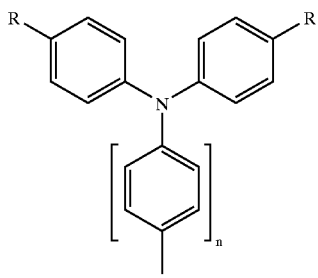

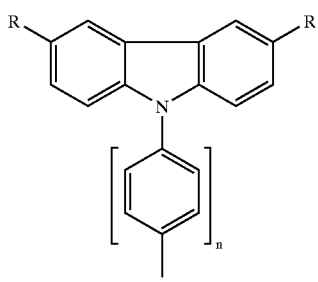

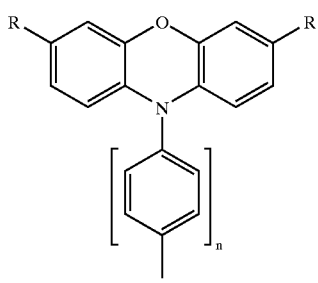

n = 0, 1, 2, 3, 4, 5 or 6

-continued
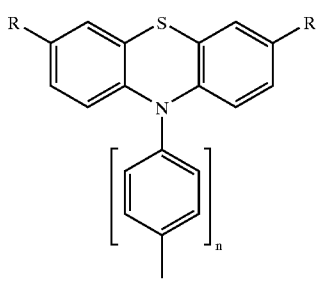
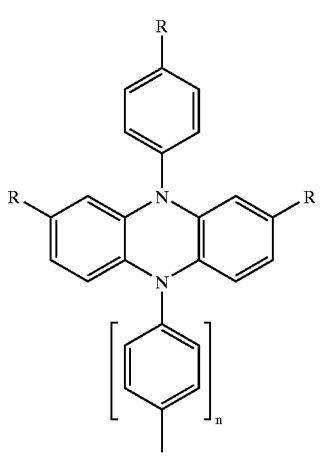
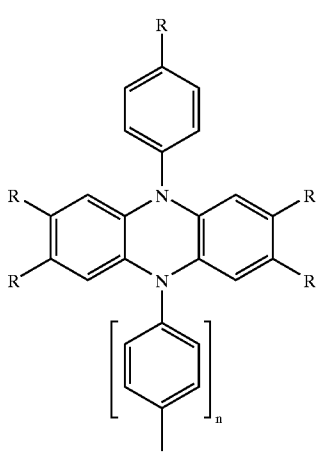
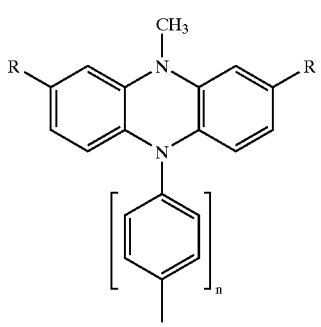
-continued
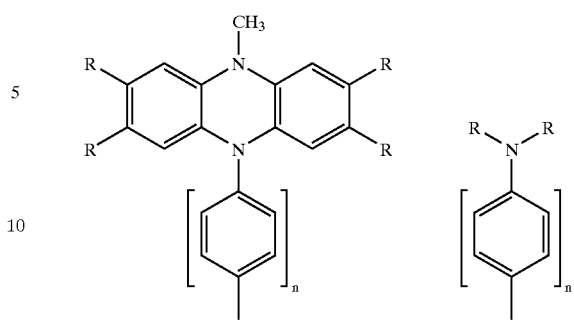
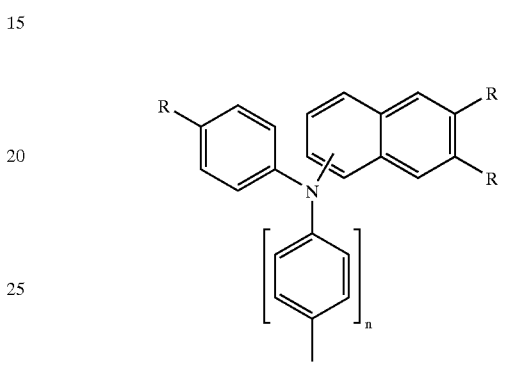
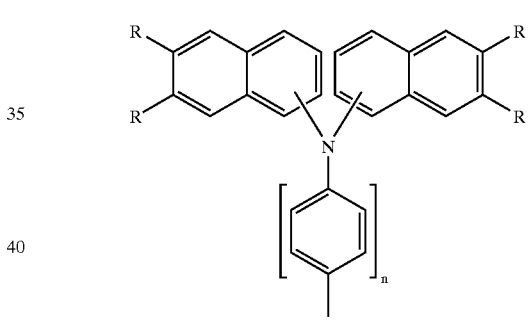
n = 0, 1, 2, 3, 4, 5 or 6
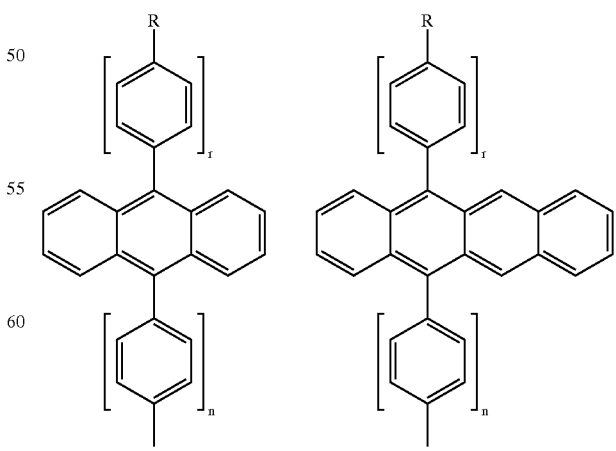

-continued

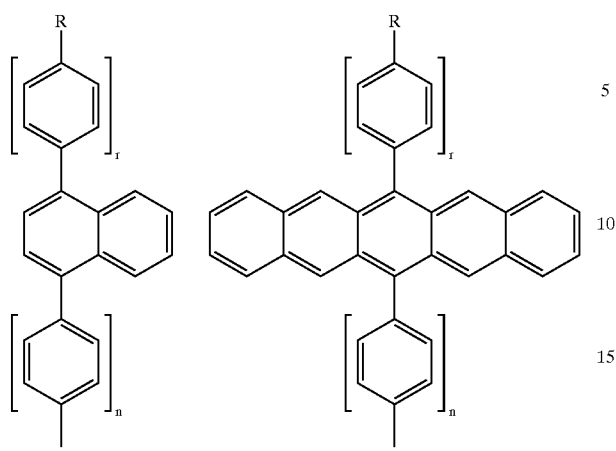

R is, independently of one another, H, alkyl, —O-alkyl, —S-alkyl, in each case having 1 to 20 carbon atoms, preferably 1 to 4 carbon atoms, phenyl, biphenyl, 1-naphthyl, 2-naphthyl, 2-thienyl, 2-furanyl, —O-phenyl, —O-biphenyl, —O-1-naphthyl, —O-2-naphthyl, —O-2-thienyl, —O-2-furanyl, CN or $NR_2$, where —O-alkyl/aryl, —S-alkyl/aryl, CN and $NR_2$ cannot be bonded to nitrogen;

n=0, 1, 2, 3 or 4, and Q and $P^1$ are, independently of one another, from the group consisting of

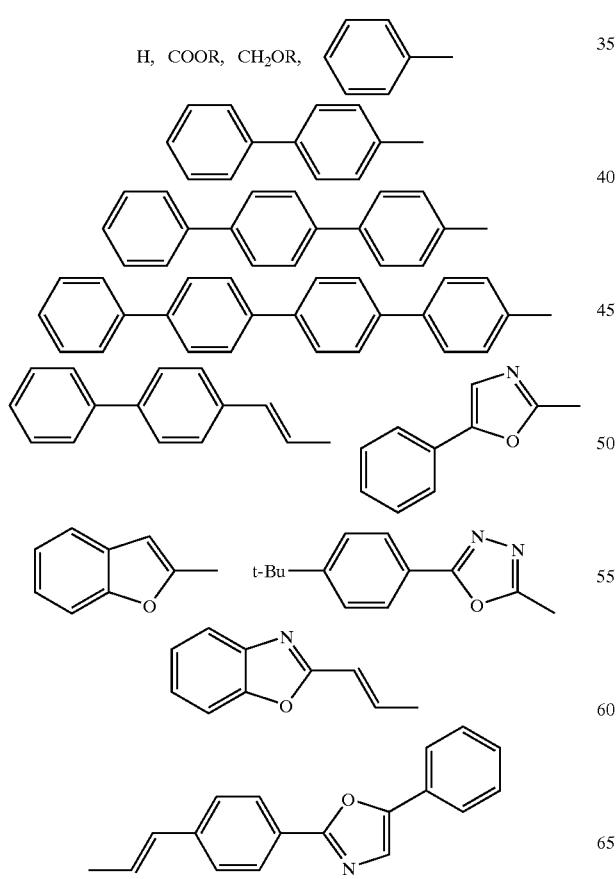

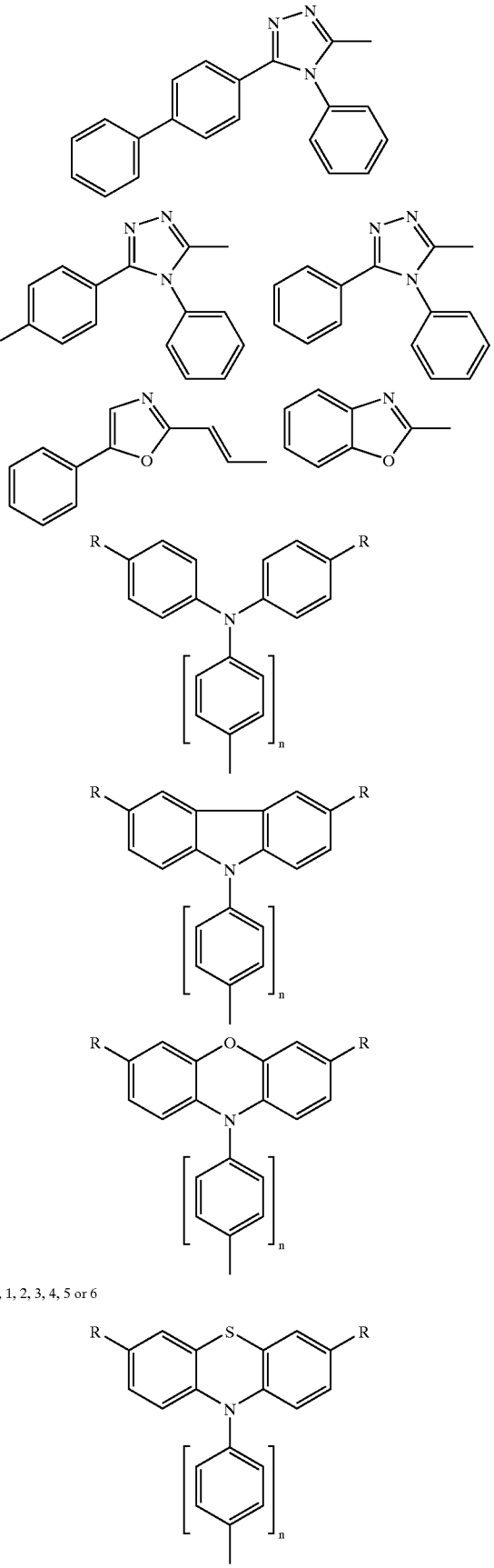

n = 0, 1, 2, 3, 4, 5 or 6

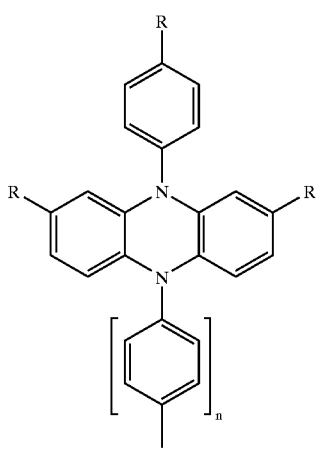
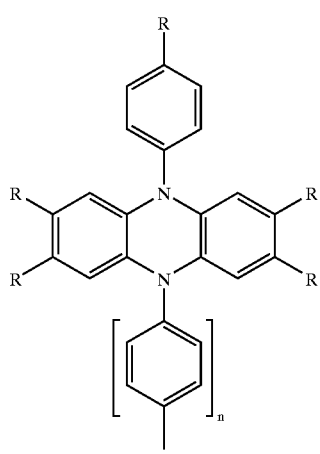
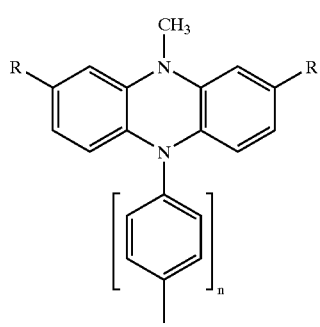
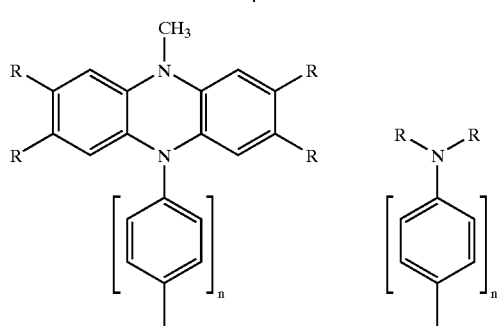
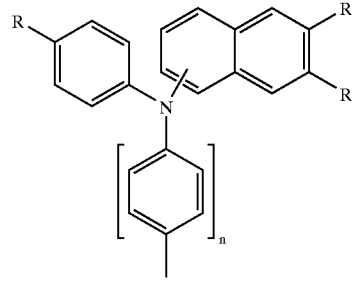
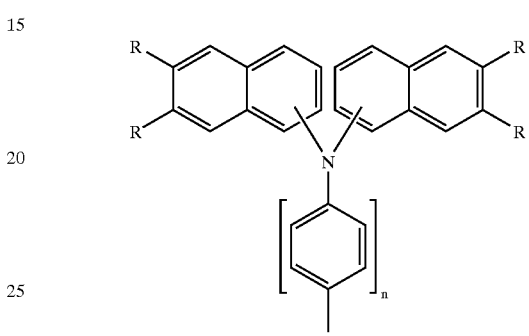
n = 0, 1, 2, 3, 4, 5 or 6
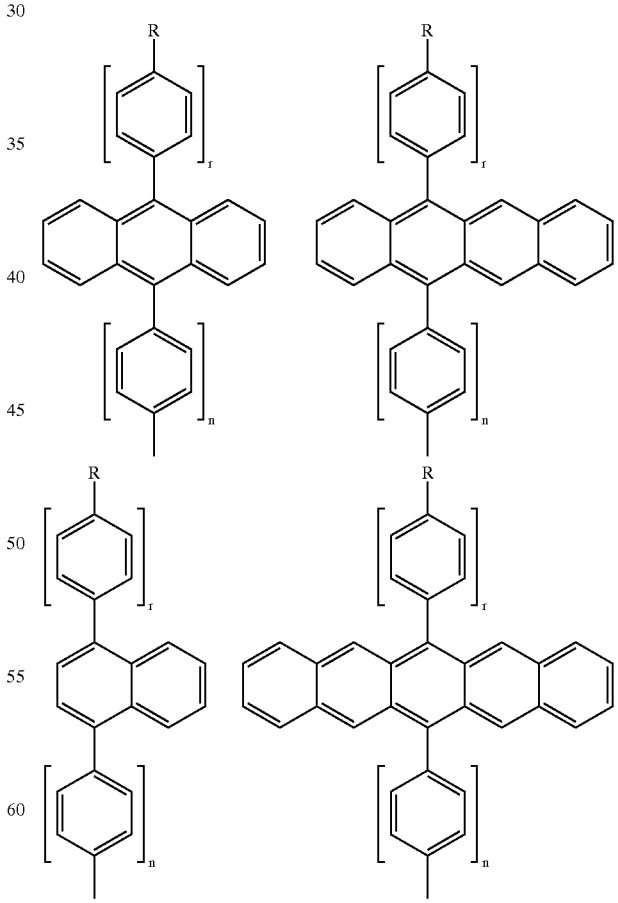
where the symbols and indices have the abovementioned meanings II.b) $K^1=N^1$ and is from the group consisting of
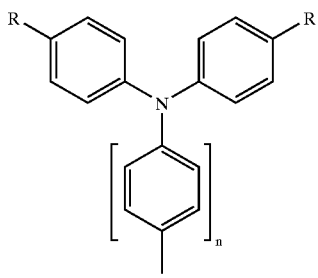
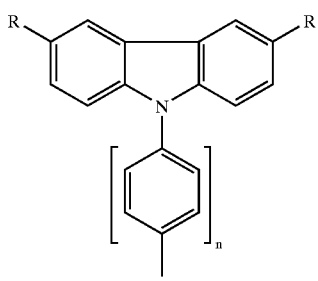
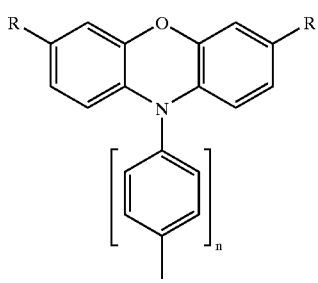
n = 0, 1, 2, 3, 4, 5 or 6
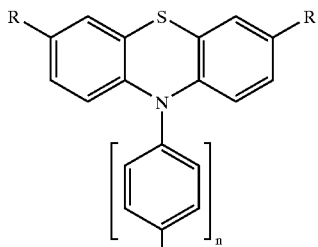
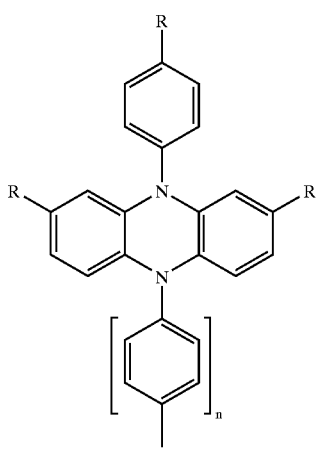
-continued
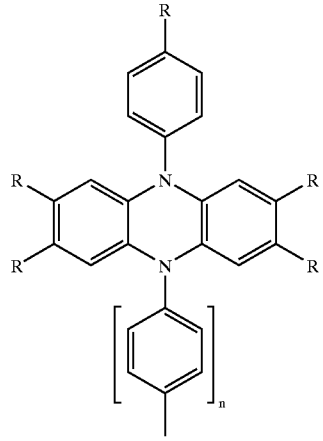
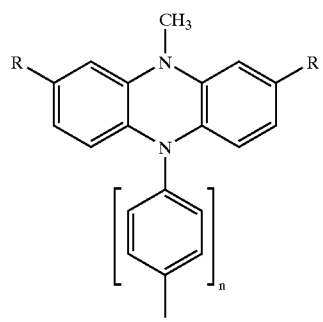
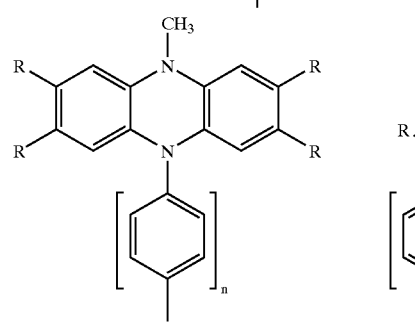
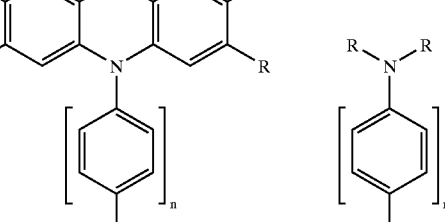
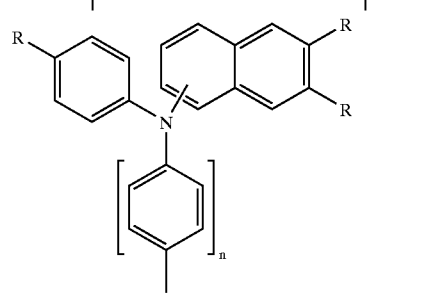
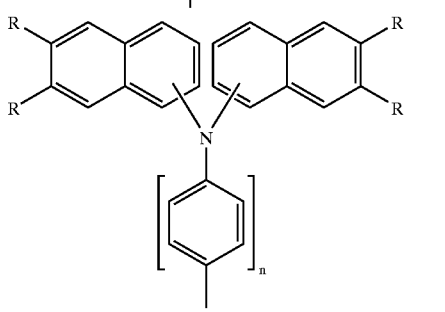
n = 0, 1, 2, 3, 4, 5 or 6

-continued
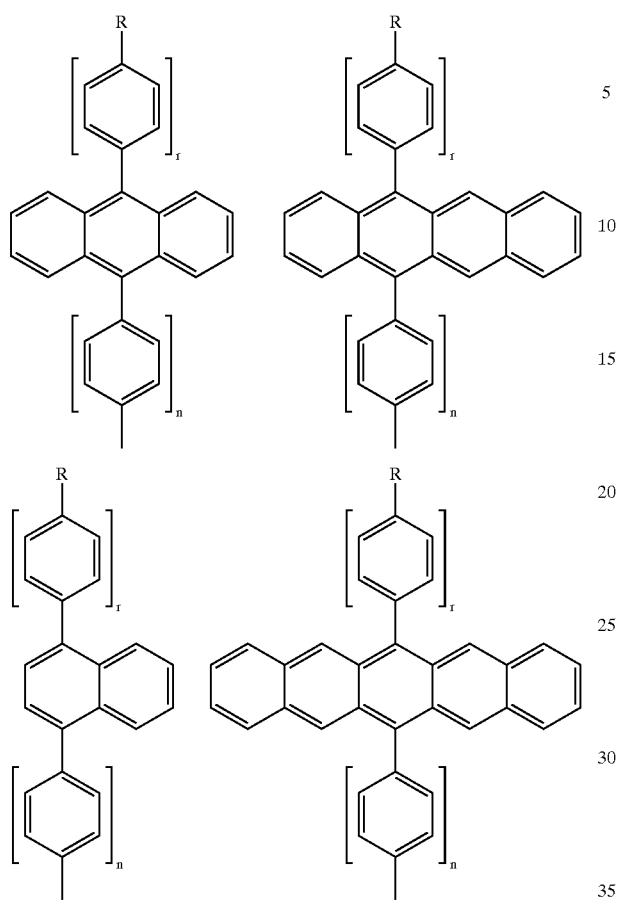
and L=M and is from the group consisting of
H, COOR, CH$_2$OR,
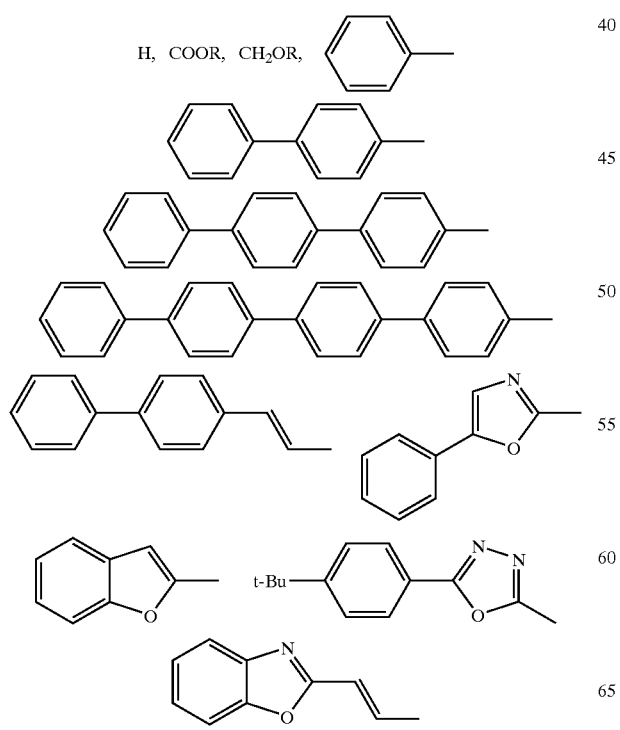
-continued
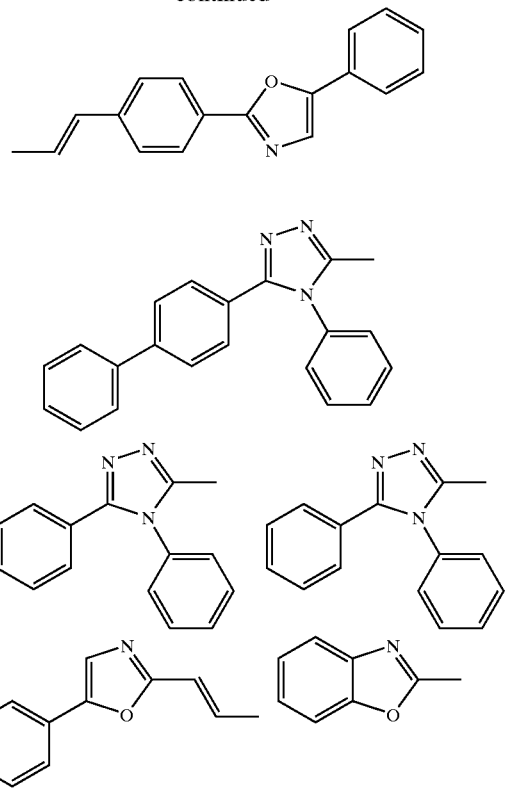
and Q and P$^1$ are, independently of one another, from the group consisting of
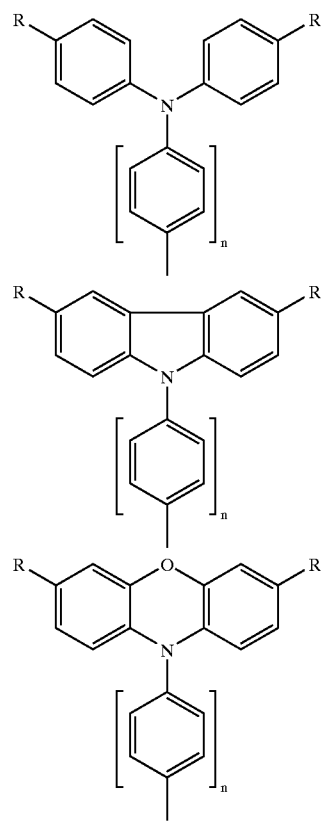
n = 0, 1, 2, 3, 4, 5 or 6

-continued
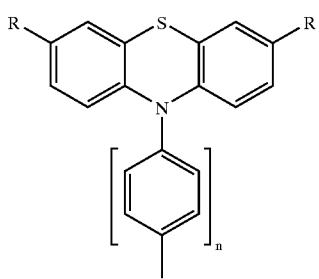
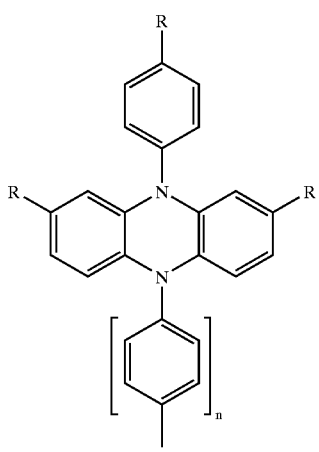
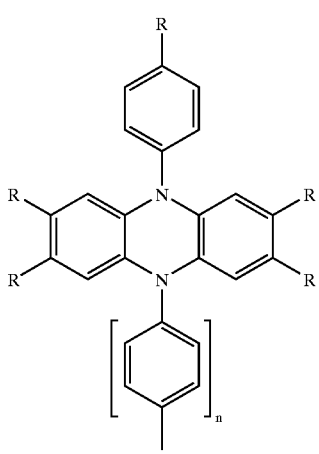
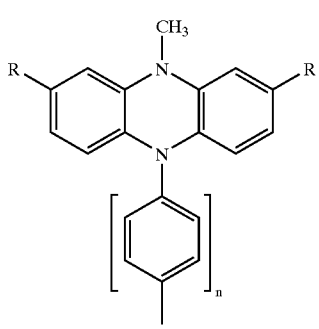
-continued
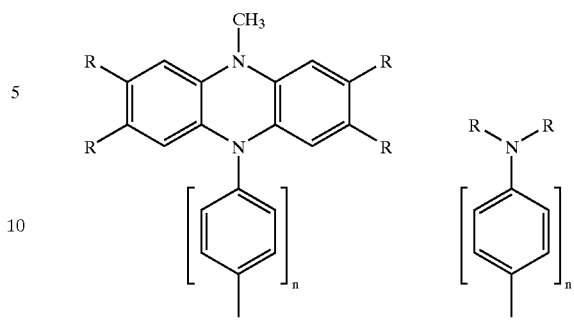
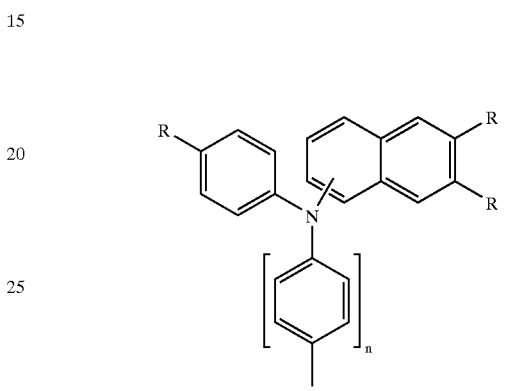
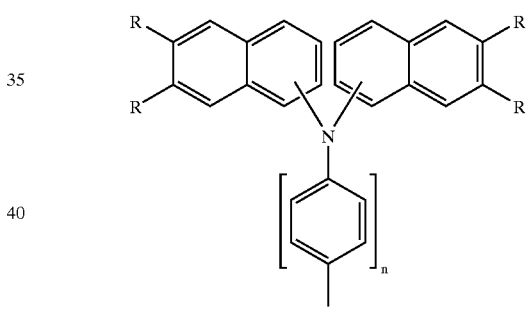
n = 0, 1, 2, 3, 4, 5 or 6
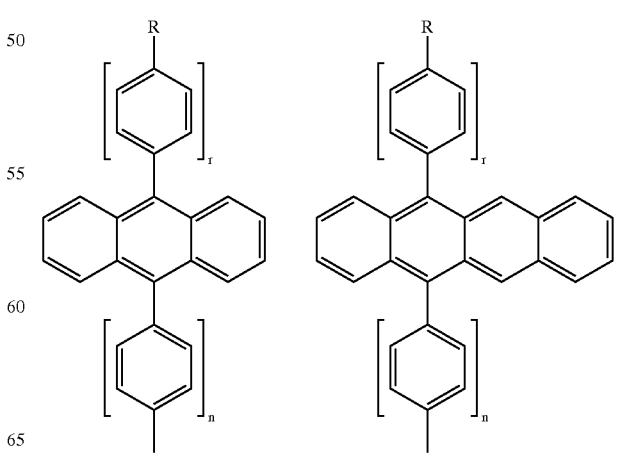

-continued
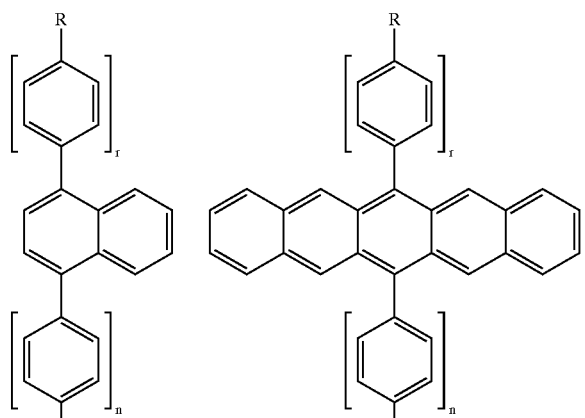
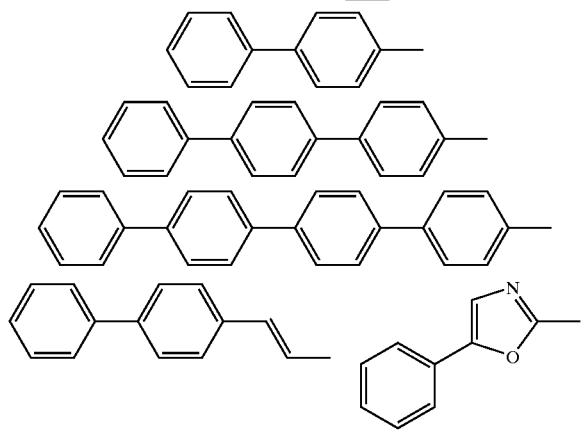
H, COOR, CH₂OR,
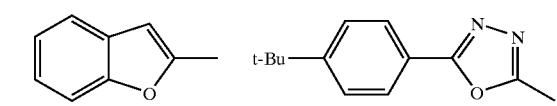
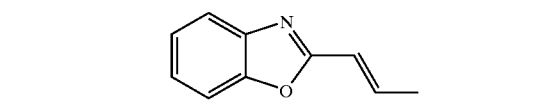
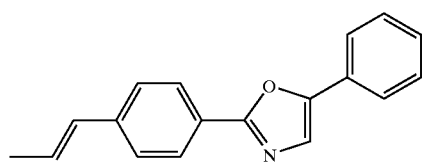
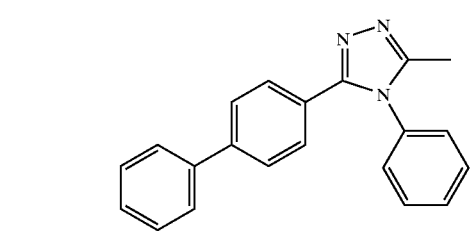
-continued
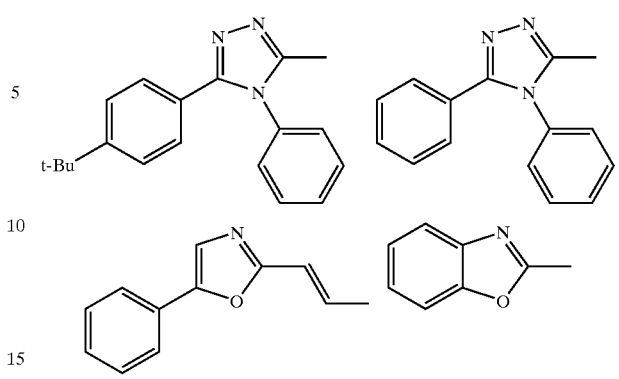
where the symbols and indices have the abovementioned meanings,
IIc) $K^1$=M and is from the group consisting of
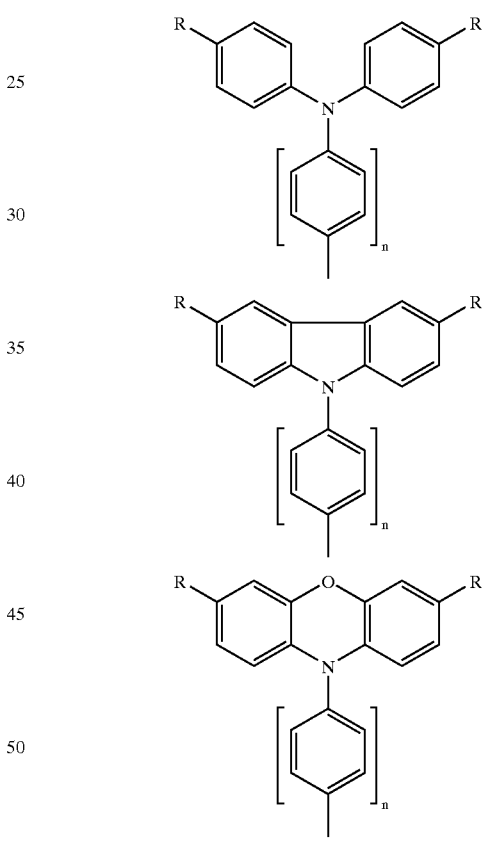
n = 0, 1, 2, 3, 4, 5 or 6
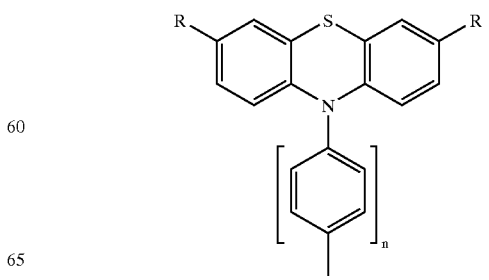

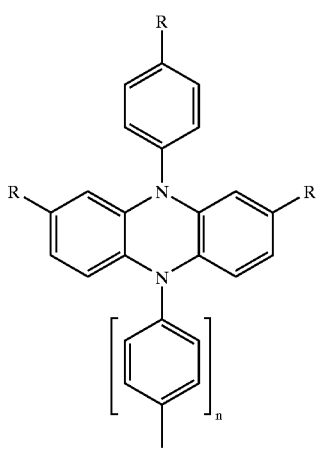
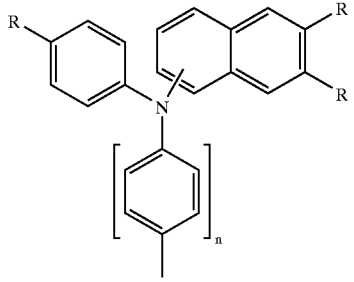
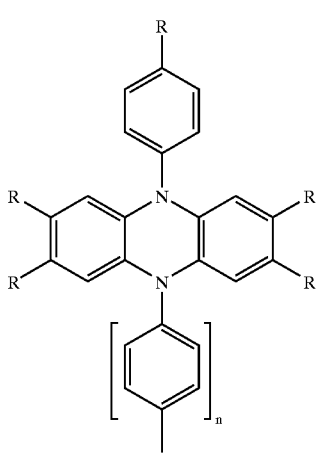
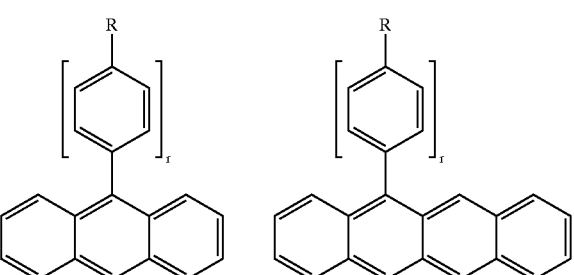
n = 0, 1, 2, 3, 4, 5 or 6
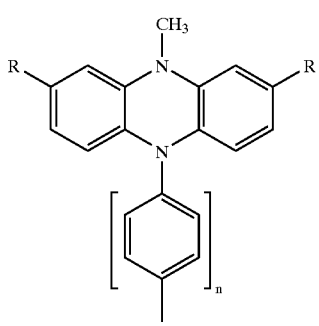
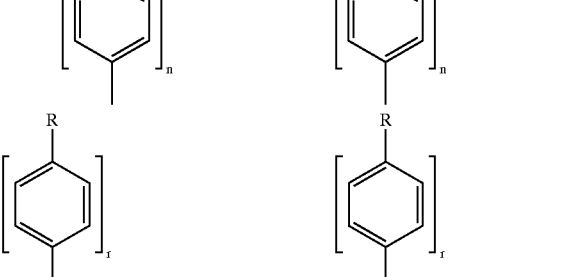
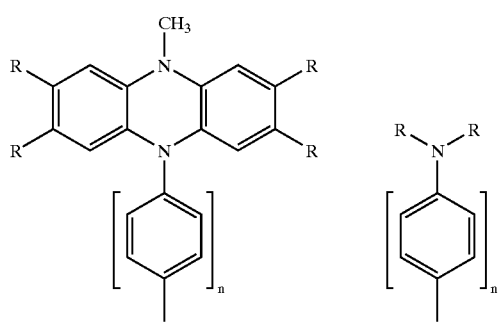
and M=N¹ and is from the group consisting of
H, COOR, CH₂OR, 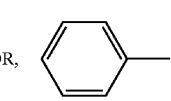

-continued
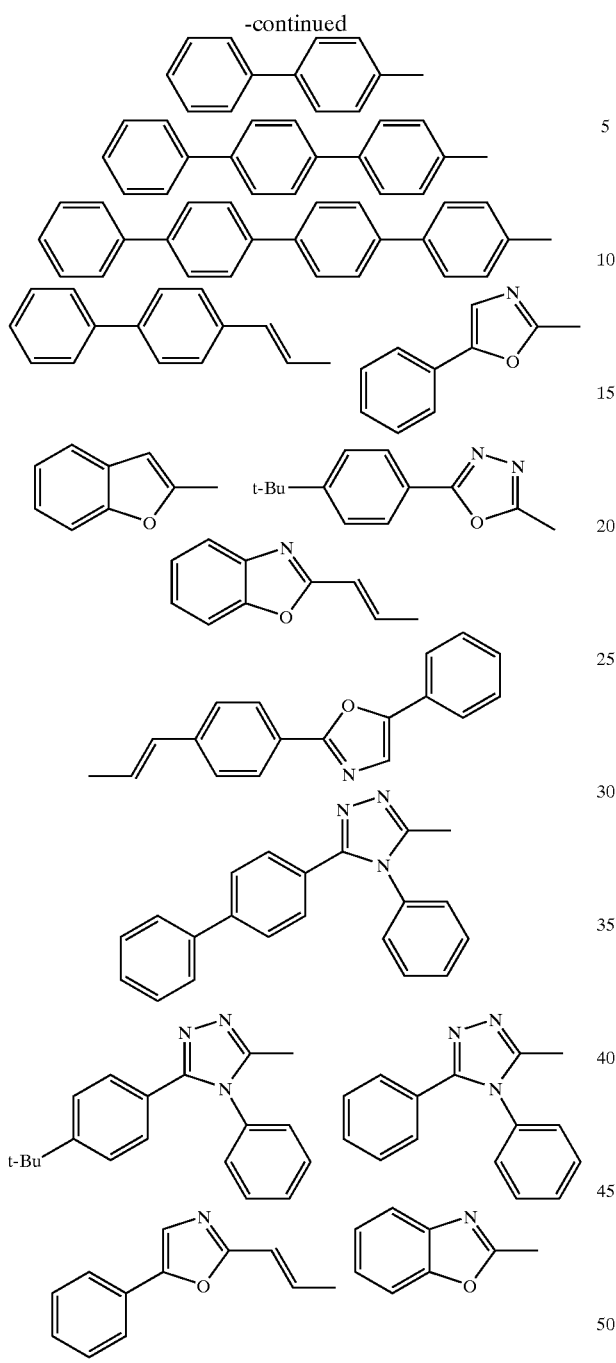
and Q and P¹ are, independently of one another, from the group consisting of
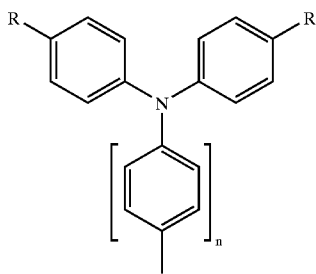
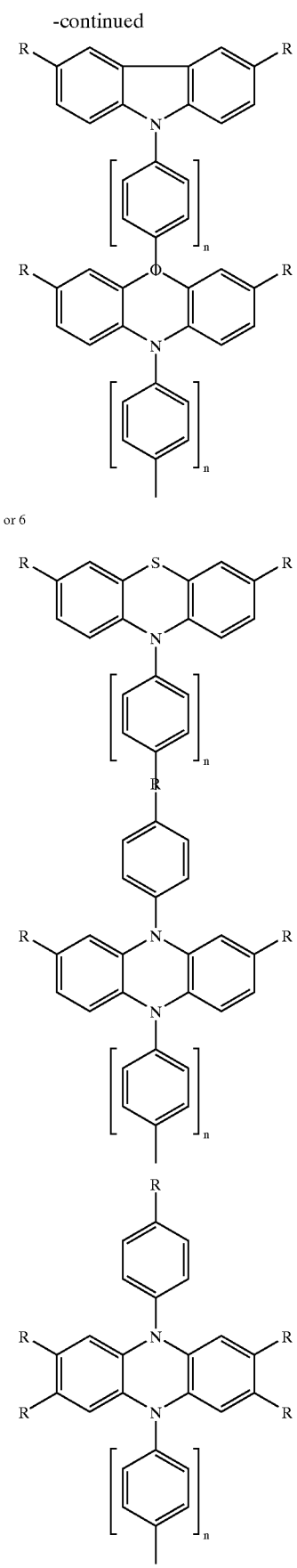
n = 0, 1, 2, 3, 4, 5 or 6

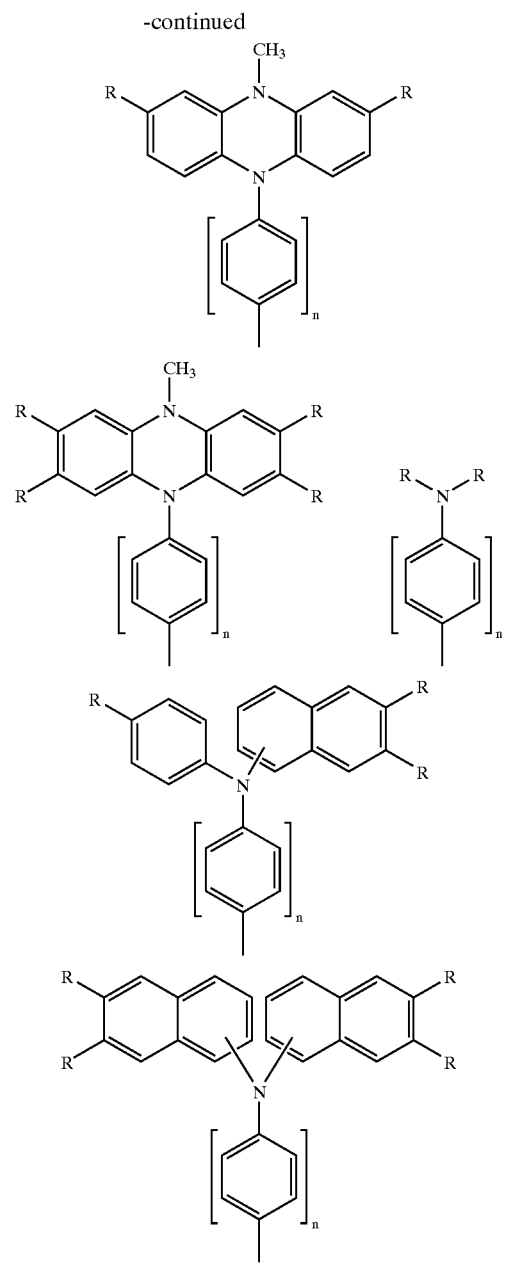
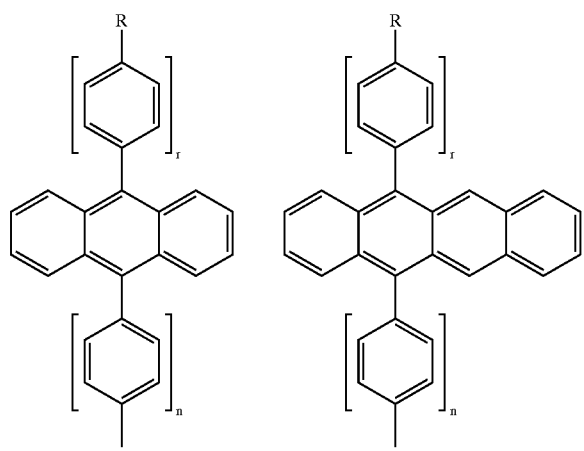
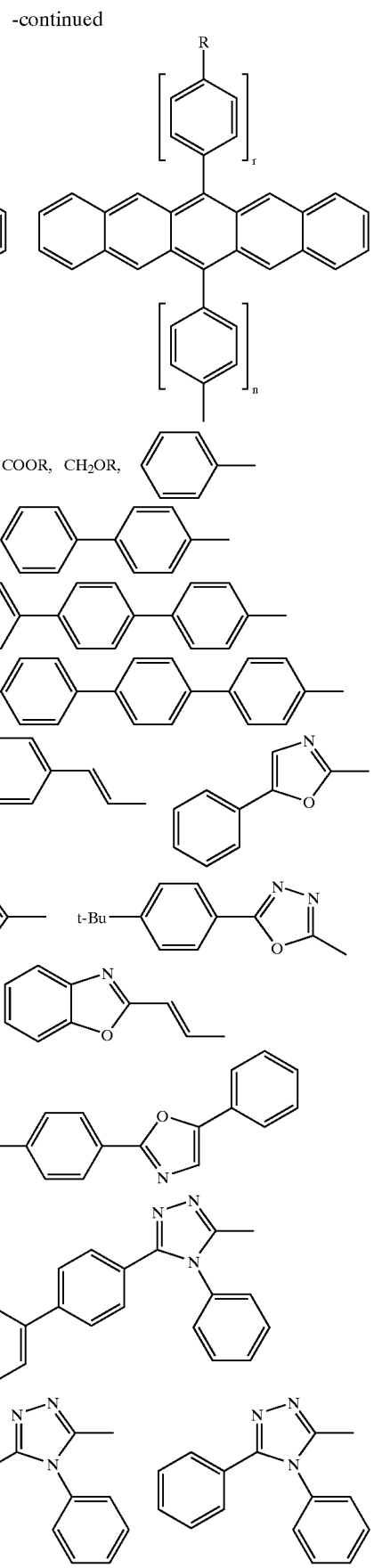

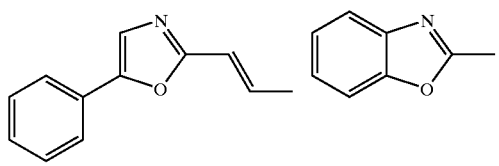

where the symbols and indices have the abovementioned meanings.

Particular preference is given to the following compounds of the formula

IIaa) $K^1=L=M=N^1$ and is from the group consisting of:

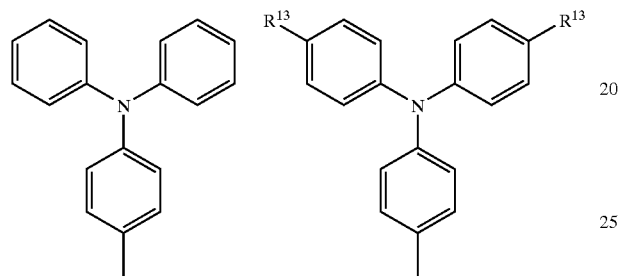

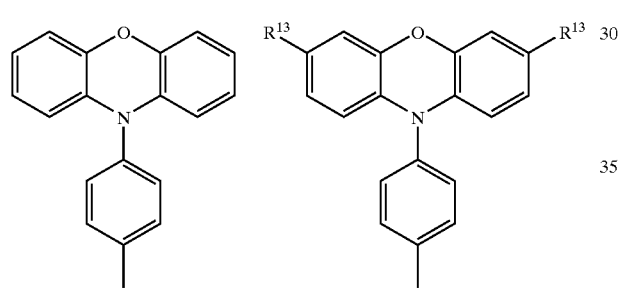

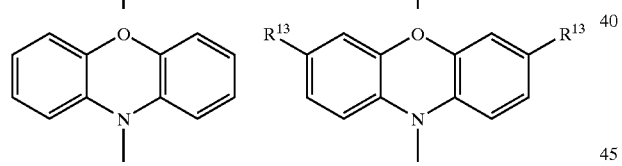

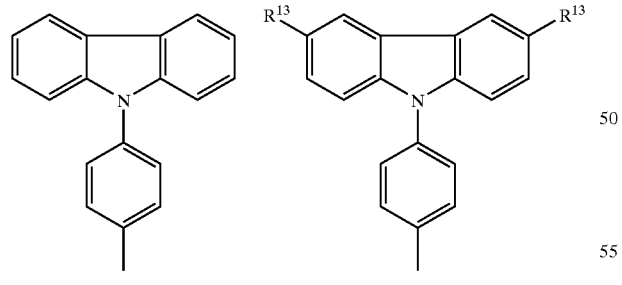

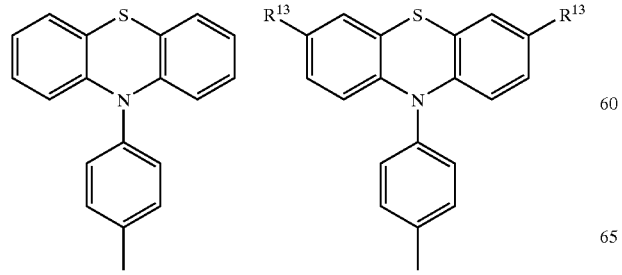

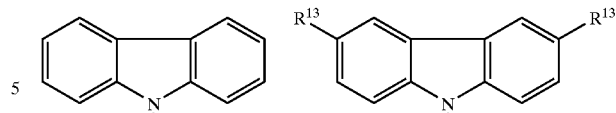

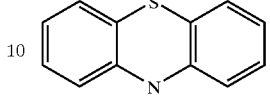

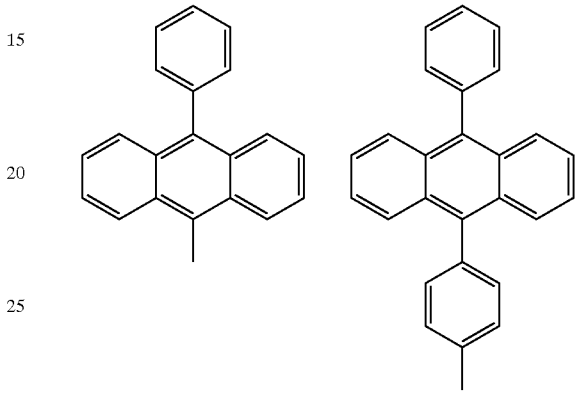

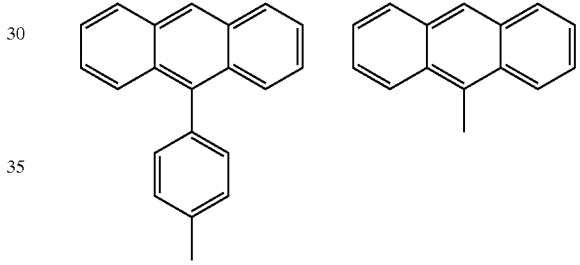

where $R^{13}$ is —O—CH$_3$, —O—C$_2$H$_5$, —S—CH$_3$, —S—C$_2$H$_5$, preferably —O—CH$_3$, —S—CH$_3$, particularly preferably —O—CH$_3$;

and $Q=P^1$ and is from the group consisting of

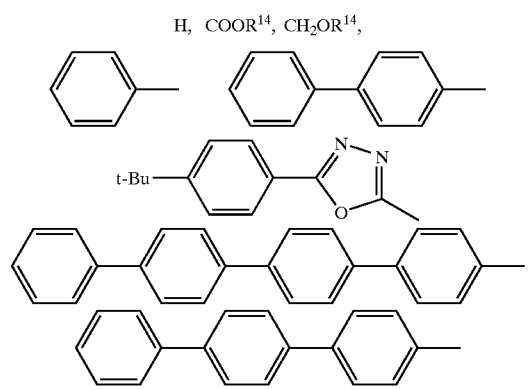

where $R^{14}$ is a straight-chain or branched alkyl group having 1 to 12, preferably 1 to 4, carbon atoms;

II.ba) $K^1=L=M=N^1=Q=P^1$ and is from the group consisting of

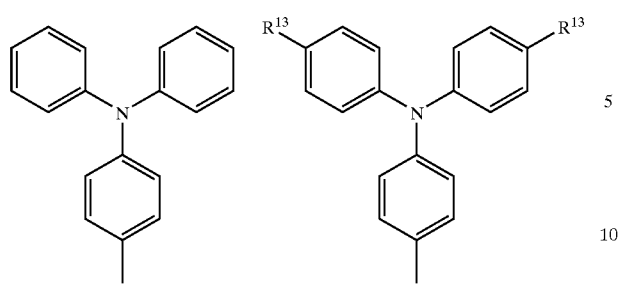
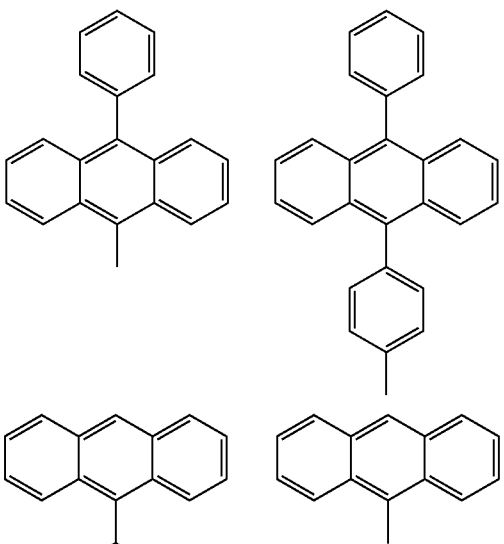
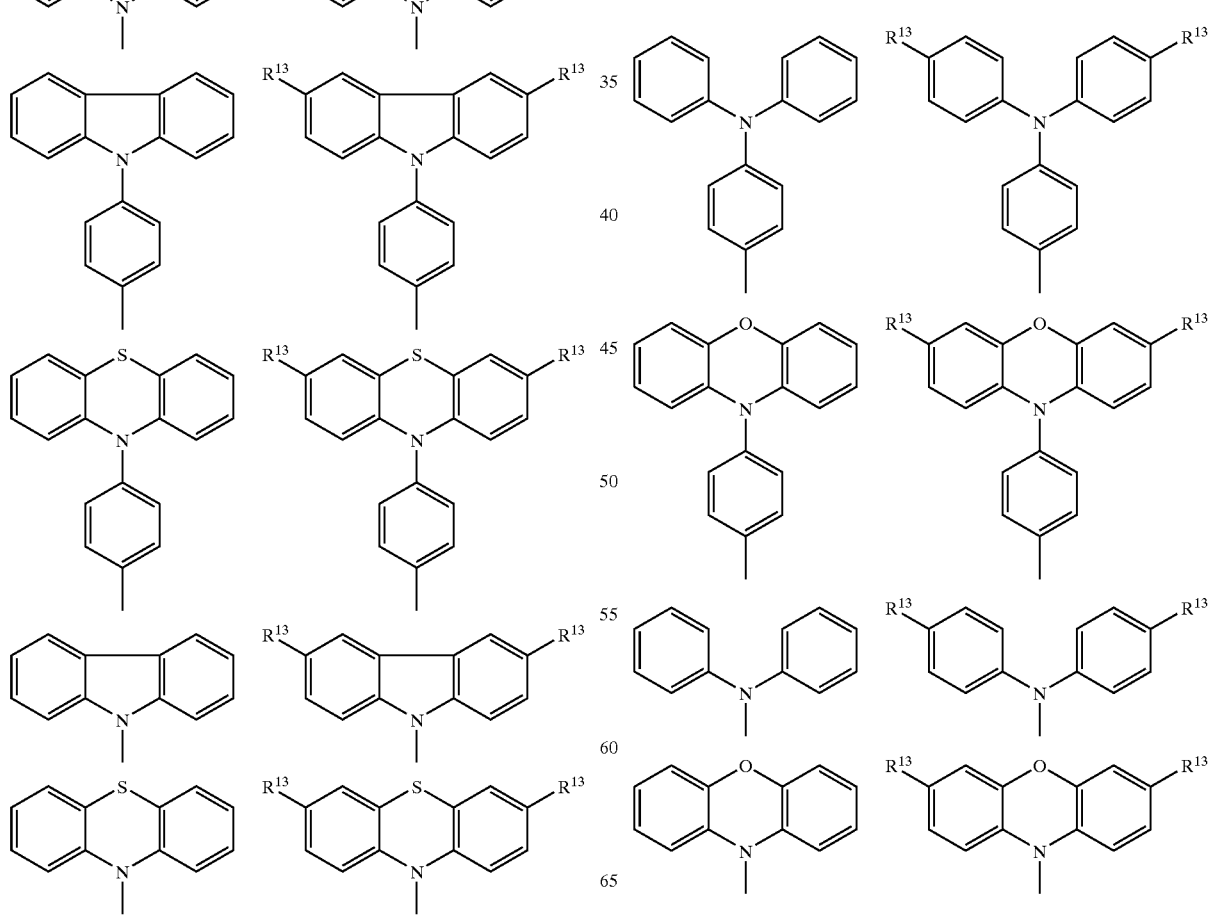
where R[13] has the abovementioned meanings;
II.ca) $K^1=L=M=N^1$ and is from the group consisting of

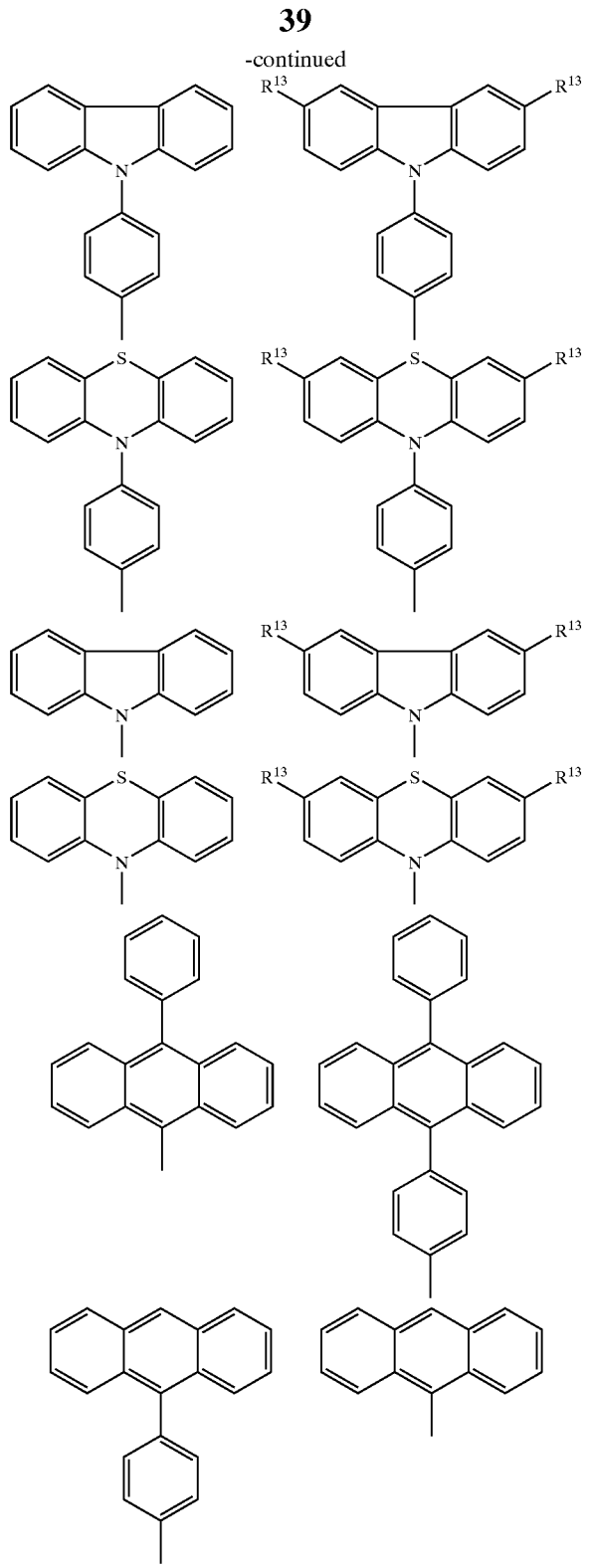

and Q=H and P¹ is from the group consisting of

H, COOR¹⁴, CH₂OR¹⁴,

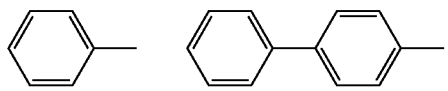

-continued

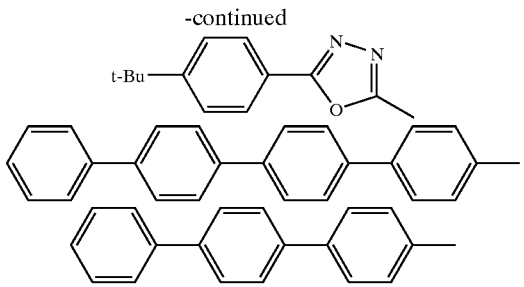

where R¹³ and R¹⁴ have the abovementioned meanings.

The spiro compounds used in accordance with the invention are prepared by methods known per se from the literature, as described in standard works on organic synthesis, for example Houben-Weyl, Methoden der Organischen Chemie [Methods of Organic Chemistry], Georg-Thieme-Verlag, Stuttgart, and in the corresponding volumes of the series "The Chemistry of Heterocyclic Compounds" by A. Weissburger and E. C. Taylor (editors).

The preparation is carried out under reaction conditions which are known and suitable for said reactions. Use can also be made here of variants which are known per se, but are not mentioned here in greater detail.

Compounds of the formula (II) are obtained, for example, starting from 9,9'-spirobifluorene, whose synthesis is described, for example, by R. G. Clarkson, M. Gomberg, J. Am. Chem. Soc. 1030, 52, 2881.

Compounds of the formula (IIa) can be prepared, for example, starting from a tetrahalogenation in positions 2,2', 7,7' of 9,9'-spirobifluorene and subsequent substitution reaction (see, for example, U.S. Pat. No. 5,026,894) or via tetraacetylation in positions 2,2',7,7' of 9,9'-spirobifluorene with subsequent C—C linkage after conversion of the acetyl groups into aldehyde groups or heterocyclization after conversion of the acetyl groups into carboxyl groups.

Compounds of the formula (IIb) can be prepared, for example, analogously to those of the formula (IIa), the stoichiometric ratios in the reaction being selected in such a way that positions 2,2' or 7,7' are functionalized (see, for example, J. H. Weisburger, E. K. Weisburger, F. E. Ray, J. Am. Chem. Soc. 1959, 72, 4253; F. K. Sutcliffe, H. M. Shahidi, D. Paterson, J. Soc. Dyers Color 1978, 94, 306, and G. Haas, V. Prelog, Helv. Chim. Acta 1969, 52, 1202).

Compounds of the formula (IIc) can be prepared, for example, by dibromination in the 2,2-position and subsequent diacetylation in the 7,7'-position of 9,9'-spirobifluorene with subsequent reaction analogously to the compounds (IIa).

Compounds of the formula (II) in which K¹, L, Q and P¹=H and M=N or Q and P¹=H, K¹=L and M=N¹ can be prepared, for example, through selection of suitably substituted starting compounds in the synthesis of the spirobifluorene, for example 2,7-dibromospirobifluorene can be synthesized from 2,7-dibromofluorenone and 2,7-dicarbethoxy-9,9'-spirobifluorene can be synthesized by using 2,7-dicarbethoxyfluorenone. The free 2',7'-positions of the spirobifluorene can then be further substituted independently.

For the synthesis of the groups $K^1$, L, M, $N^1$, $P^1$, $R^1$, $R^2$, $R^3$ and $R^4$, reference may be made, for example, to DE-A 23 44 732, 24 50 088, 24 29 093, 25 02 904, 26 36 684, 27 01 591 and 27 52 975 for compounds containing 1,4-phenylene groups;

DE-A 26 41 724 for compounds containing pyrimidine-2,5-diyl groups;

DE-A 40 26 223 and EP-A 03 91 203 for compounds containing pyridine-2,5-diyl groups;

DE-A 32 31 462 for compounds containing pyridazine-3,6-diyl groups;

N. Miyaura, T. Yanagi and A. Suzuki in Synthetic Communications 1981, 11, 513 to 519, DE-A-39 30 663; M. J. Sharp, W. Cheng, V. Snieckus, Tetrahedron Letters 1987, 28, 5093; G. W. Gray, J. Chem. Soc. Perkin Trans II 1989, 2041 and Mol. Cryst. Liq. Cryst. 1989, 172, 165; Mol. Cryst. Liq. Cryst. 1991, 204, 43 and 91; EP-A 0 449 015; WO 89/12039; WO 89/03821; EP-A 0 354 434 for direct linking of aromatic compounds and heteroaromatic compounds.

The preparation of disubstituted pyridines, disubstituted pyrazines, disubstituted pyrimidines and disubstituted pyridazines is described, for example, in the corresponding volumes of the series "The Chemistry of Heterocyclic Compounds" by A. Weissberger and E. C. Taylor (editors).

The detector according to the invention preferably comprises a semiconductor which has a very large band gap, preferably at least 3.0 eV. Suitable semiconductors are thus preferably metal oxide semiconductors, in particular the oxides of the transmission metals and the elements of the third main group and of the fourth, fifth and sixth sub-group (of the Periodic Table of the Elements), which for example the oxides of titanium, zirconium, hafnium, strontium, zinc, indium, yttrium, lanthanum, vanadium, niobium, tantalum, chromium, molybdenum, tungsten, but also oxides of tin, iron, nickel or silver, perovskites, such as $SrTiO_3$, $CaTiO_3$, or oxides of other metals of the second and third main group or mixed oxides or oxide mixtures of these metals. However, it is also possible to use any other metal oxide having semiconductor properties and a large energy separation (band gap) between the valence band and the conduction band. Particularly preferred semiconductor materials are titanium dioxide, $Nb_2O_5$ and ZnO, very particularly preferably titanium dioxide.

The semiconductor preferably has a roughness factor of greater than 1, particularly preferably greater than 20, very particularly greater than 150. The roughness factor is defined as the ratio between an actual/effective surface area and the area of the projection of this surface of a body, thus in this case the surface of the semiconductor.

The roughness factor can be determined, for example, by gravimetric adsorption methods, as described, for example, in S. Kohlrausch, Praktische Physik, Volume 1, p. 397 (Stuttgart: B. G. Teubner, 1985). In general, the size of the pores is 5–200 nm, preferably 10–50 nm.

A process for the production of polycrystalline metal oxide semiconductor layers using the SOL-GEL process (described in detail, for example, in Stalder and Augustynski, J. Electrochem. Soc. 1979, 126, 2007), where the percentage relative humidity of the ambient atmosphere in the metal alkoxide hydrolysis process step can be in the range from 30% to 80% and is kept constant within ±5%, preferably ±1%, gives metal oxide semiconductor layers with which particular sensitivity can be achieved in photodetectors according to the invention.

The roughness increases the contact area between semiconductor and charge transport layer.

As an example of the production of a titanium oxide layer ($TiO_2$) having a high roughness factor on a titanium substrate, the SOL-GEL process is described by way of example below.

The titanium substrate made from pure titanium having a purity of about 99.5% is firstly cleaned for about 30 minutes in approximately 18% strength boiling HCl. The titanium ethoxide solution can be obtained, for example, by dissolving 21 mmol of $TiCl_4$ in 10 ml of very pure ethanol (puriss.). This solution is then diluted with very pure methanol (puriss.) to give a titanium concentration in the range from about 25 to 50 mg/ml. One drop of the solution is placed on the titanium substrate, and the titanium alkoxide is hydrolyzed at room temperature for about 30 minutes at a humidity level of 48±1%. The substrate with the hydrolyzed layer is then heated at about 450° C. for about 15 minutes. This process is repeated a number of times. After 10 to 15-fold repetition, the $TiO_2$ layer has reached a thickness of about 20 mm. The substrate with the layer is then dried by heating at about 500° C. for about 30 minutes in a pure argon atmosphere (for example 99.997%). The $TiO_2$ layer produced in this way has a roughness factor in the region of 200. Metal oxide semiconductor layers of this type (also of other metals) can be produced on other substrates by analogous processes. The upper layers of the semiconductor may, if desired, be doped with a divalent or trivalent metal, as described, for example, in WO-A 91/16719.

The sensitivity, i.e. the photoelectronic yield for visible light, can be increased by chemisorption of so-called chromophores, also referred to as sensitizers or dyes, as charge carriers on the surface of the semiconductor. The two functions of light absorption and charge carrier separation are separated in these photoelectronic systems. Light absorption is undertaken by the chromophore in the surface region, and separation of the charge carriers takes place at the semiconductor/chromophore interface. Different chromophores have different spectral sensitivities. The choice of chromophore can thus be matched to the spectral composition of the light from the light source in order to increase the yield as much as possible. Suitable chromophores, i.e. sensitizers, are, in particular, the complexes of transition metals of the type metal ($L_3$), metal ($L_2$) of ruthenium and osmium (for example ruthenium tris(2,2'-bipyridyl-4,4'-dicarboxylate), ruthenium cis diaqua bipyridyl complexes, such as ruthenium cis-diaqua bis(2,2'-bipyridyl-4,4'-dicarboxylates) and porphyrins (for example zinc (tetra(4-carboxyphenyl)porphyrin) and cyanides (for example iron hexacyanide complexes) and phthalocyanines.

The chromophores can be chemisorbed, adsorbed or firmly attached in another manner in the region of the surface of the metal oxide semiconductor. Favorable results have been achieved, for example, with chromophores which are bound to the surface of the metal oxide semiconductor by means of carboxylic acid or phosphoric acid ligands.

Suitable chromophores are also described, for example, in Chem. Rev. 1995, 49–68.

Particular preference is given to the chromophores (VIII) and (IX)

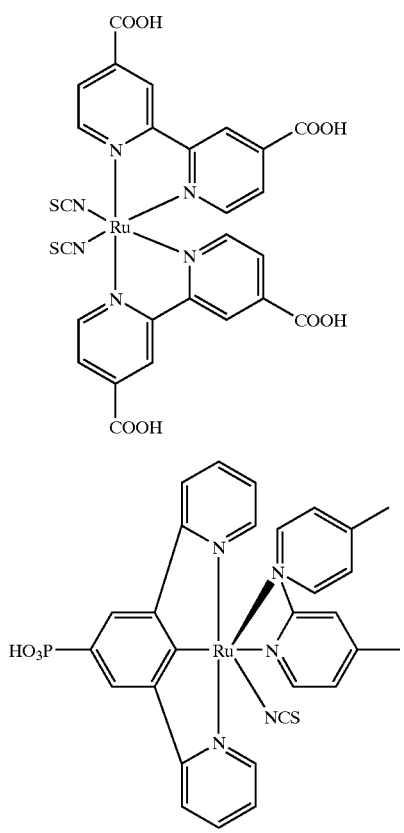

whose synthesis and properties are described in J. Chem. Soc. Chem. Comm. 1995, 65.

The application of the chromophore, for example $RuL_3^{4-}$, is carried out, for example, by immersing the substrate with the oxide layer into an ethanolic solution of $2 \times 10^{-4}$ M $RuL_3^{4-}$, for about one hour. Other chromophores can be applied to titanium oxide or other metal oxide semiconductors by analogous processes.

Suitable materials, preferably different, for the electrode and counterelectrode are stable, metallically conducting substances, for example Au, Ag, Pt or Cu, or other metals. However, it is also possible in some applications to use preferably light-transparent, conductive substances, such as doped metal oxides, for example indium-tin oxide, Sb-doped tin oxide, F-doped tin oxide or Al-doped tin oxide. The work function of the electrode material used can preferably be matched to the ionization potential of the hole transport material used.

The electrode can, as described in EP-A 0 333 641, be applied to a transparent substrate, for example glass, and bonded to the hole transport layer. In the cell described in this invention, it can preferably be applied directly to the hole transport layer by physical deposition methods, for example vapor deposition or sputtering or by printing methods using a conductive printing paste, without a second glass plate being necessary. This process is preferred if the weight of the cell is to be minimized.

If desired, the electrode can be coated with a further semiconductor between the electrode and the semiconductor layer, as described in WO-A 93/19479. This is preferred if the semiconductor layer has a roughness factor of >>1 in order to avoid direct charge transfer from the hole conductor layer to the electrode 11.

Suitable electrically insulating materials 16 and 17 and, if present, as side frame for the cell according to the invention are, for example, plastic or glass.

The invention therefore also relates to a process for the production of a radiation detector, which comprises
   a) applying a semiconductor layer, preferably in nanocrystalline form, to a conductive solid support, for example by CVD or printing methods,
   b) then applying a monolayer of a sensitizer dye, for example by dipping or jet printing,
   c) then applying a transport layer comprising a hole conductor material,
   d) then applying the counterelectrode, and, if desired,
   e) applying an insulating layer thereto.

The detector can advantageously be sealed, for example using an adhesive or a film.

The electro-optical detector according to the invention generally has a thickness in the range from 0.1 to 20 mm (with substrate).

In order to increase the radiation yield in the case of detection of UV radiation, the reverse of the cell can be constructed in such a way that the radiation is reflected back into the detector in diffuse form.

The detection takes place in a known manner which is familiar to the person skilled in the art, generally by measurement of the (photo)current, the change in conductivity or the voltage. The reading method to be selected depends on the desired use, the light intensity expected and the dynamic band width of the signals to be measured.

The current measurement can be carried out using a galvanometer (in the nA to A range), for example by means of a minigalvanometer with LCD display.

The conductivity change can be measured using a galvanometer in combination with an external voltage source. The voltage can be measured by means of a voltmeter. These detection methods are described in general, for example, in John Moore, Christopher Davis and Michael Coplan, Building Scientific Apparatus, pp. 257–264, Adison-Wesley, London, 1983.

The invention is explained in greater detail by the examples.

SYNTHESIS EXAMPLES

Example 1

9,9'-Spirobifluorene 7.66 g of magnesium turnings and 50 mg of anthracene were introduced under argon into 100 ml of dry diethyl ether in a 1 l three-necked flask fitted with reflux condenser, and reacted with 75 g of 2-bromobiphenyl dissolved in 60 ml of dry diethyl ether. 56.77 g of 9-fluorenone dissolved in 500 ml of dry diethyl ether were subsequently added dropwise with stirring. When the addition was complete, the mixture was boiled for a further 2 hours. The precipitated yellow magnesium complex was filtered off with suction and washed with ether. The yellow magnesium complex filtered off was then hydrolyzed in a solution of 48 g of ammonium chloride in 800 ml of ice-water. After the mixture had been stirred for 60 minutes, the fluorenol formed was filtered off with suction, washed with water and sucked dry.

The dried product was then refluxed for 2 hours in about 800 ml of glacial acetic acid with addition of 3 ml of conc. HCl. After cooling, the product was filtered off with suction, washed with water and dried. For further purification, the product was recrystallized once from acetone, giving 86 g of 9,9'-spirobifluorene as colorless crystals (82% yield).

Example 2

2,2'7,7'-Tetraiodo-9.9'-spirobifluorene 5.8 g (22.8 mmol) of iodine were added to 3.16 g (10 mmol) of 9,9'-spirobifluorene, dissolved in 30 ml of chloroform, at room temperature in a 100 ml two-necked flask fitted with reflux condenser and drying tube, and 10.75 g (25 mmol) of bis(trifluoroacetoxy)iodobenzene were subsequently added. The reaction mixture warmed to about 40°, with formation of a pale precipitate. After 1.5 hours, the product, which had already precipitated out, was filtered off with suction, and washed with chloroform and dried. The chloroform solutions were combined, and washed successively with saturated sodium sulfite solution, saturated sodium carbonate solution and water. After drying over sodium sulfate, the mixture was evaporated, and a second product fraction was obtained. The two product fractions were combined, boiled up in acetone, cooled and filtered with suction, giving 8.1 g of 2,2'7,7'-tetraiodo-9,9'-spirobifluorene as a colorless microcrystalline powder in virtually quantitative yield.

$^1$H-NMR (CDCl$_3$, ppm): 6.98 (d, J=1.48 Hz, 4H, H-1,1', 8,8'); 7.54 (dd, J=7.88, 1.48 Hz, 4H, H-3,3',6,6'); 7.72 (d, J=7.88 Hz, 4H, H-4,4',5,5').

Example 3

2,2',7,7'-Tetrakis(diphenylamino)-9,9'-spirobifluorene (Compound 2)

2.1 g (2.56 mmol) of tetraiodospirobifluorene were heated at the boil for 48 hours under nitrogen with 2.25 g (13.3 mmol) of diphenylamine with addition of 2.76 g (20 mmol) of potassium carbonate, 635 mg (10 mmol) of copper powder and 208 mg (0.79 mmol) of 18-crown-6 in 10 ml of o-dichlorobenzene. After cooling, the inorganic constituents were filtered off and washed with warm dichlorobenzene. The dichlorobenzene was removed by vacuum distillation (100 mbar, 135–140° C.). The residue was dissolved in chloroform, filtered over a short silica gel column and evaporated. For purification, the product was recrystallized first from chloroform/acetone and subsequently from chloroform/diethyl ether with addition of two drops of hydrazine hydrate. 1.4 g of 2,2',7,7'-tetrakis-(diphenylaminey9,9'-spirobifluorene were isolated in a yield of 56% in the form of very fine, yellowish-white crystal needles.

$^1$H-NMR (CDCl$_3$, ppm): 6.69 (d, J=1.83 Hz, 4H, H-1,1', 8,8'); 6.92 (dd, J=8.18 1.99 Hz, 4H, H-3,3',6,6'); 6.98 (m, 24H); 7.20 (m, 16H); 7.45 (d, J=8.18 Hz, 4H, H4,4',5,5').

Example 4

N,N,N',N',N'',N'',N''',N'''-Octakis(4-methoxyphenyl)-9,9'-spirobifluorene-2,2',7,7'-tetramine The reaction, analogous to the above procedure, of tetraiodospirobifluorene with 4,4'-dimethoxydiphenylamine gave N,N,N',N',N'',N'',N''',N'''-octakis(4-methoxyphenyl)-9,9'-spirobifluorene-2,2',7,7'-tetramine as a yellowish crystal powder in comparable yield.

$^1$H-NMR (CDCl$_3$, ppm): 3.76 (s, 24H, OCH$_3$); 6.54 (d, J=1.99 Hz, 4H, H-1,1',8,8'); 6.75 (dm, J=9.07 Hz, 16H); 6.79 (dd, J=8.18, 1.99 Hz, 4H, H-3,3',6,6'); 6.90 (dm, J=9.07 Hz, 16H); 7.35 (d, J=8.18 Hz, 4H, H-4,4',5,5').

The reference numerals in the following figures have the following meanings:

| | | | | | |
|---|---|---|---|---|---|
| 10A | immobilization zone | 40 | light | 81 | recognition element |
| 10B | light | 41 | support | 82 | support |
| 11 | enzyme | 42 | light source | 83 | detector |
| 12 | antibody | 43 | imaging optics | 84 | light source |
| 13 | antigen | 44 | data storage medium | 91 | reader |
| 14 | antibody | 45 | detector | 92 | support |
| 16 | detection | 46 | detector support | 93 | matrix |
| 17 | products | 50 | light | 94 | opt. device |
| 18 | catal. reaction | 51 | support | 95 | support |
| 19 | antibody | 52 | light source | 96 | matrix |
| 20 | radiation | 53 | storage medium | 97 | light source |
| 21 | support | 54 | detector | 98 | light |
| 22 | conductive layer | 55 | detector support | 101 | laser diode layer |
| 23 | semiconductor | 60 | light | 102 | chromo-/fluorophore |
| 24 | dye | 61 | substrate | 103 | antigen |
| 25 | charge transport layer | 62 | light source | 104 | light |
| 26 | counterelectrode | 63 | opt. Device | 105 | reflect. back wall |
| 27 | insulating layer | 64 | detector | 106 | cascade |
| 28 | insulating layer | 65 | substrate | 107 | light |
| 30 | radiation | 70 | light | 108 | antigen |
| 31 | support | 71 | light source | 109 | dye |
| 32 | conductive layer | 72 | support | 111 | measurement electronics |
| 33 | semiconductor | 73 | recognition element | 112 | film material |
| 34 | dye | 74 | opt. Device | 113 | binding zone |
| 35 | charge transport layer | 75 | matrix | 114 | detector support |
| 36 | counterelectrode | 76 | support | 115 | housing |
| 37 | insulating layer | 77 | transmit./emit. light | | |
| 38 | insulating layer | 80 | light | | |

What is claimed is:

1. A device for the detection and determination of the intensity of electromagnetic radiation, wherein the device comprises a matrix of detectors which have (i) a conductive layer, (ii) a photoactive layer of a semiconductor having a band width of greater than 2.5 eV which is applied to said conductive layer, (iii) a dye applied to the semiconductor, (iv) a charge transport layer comprising a hole conductor material applied above said dye applied to the semiconductor (v) a counter-electrode layer applied to said charge transport layer and (vi) insulating layers, wherein at least one side of the detector is transparent to the electromagnetic radiation and the detectors of said matrix are connected in parallel to an electronic measurement device.

2. The device as claimed in claim 1, wherein the semiconductor has a band gap of greater than 3 eV.

3. The device as claimed in claim 1, wherein the semiconductor layer has a roughness factor of >1.

4. A device as claimed in claim 1, wherein the semiconductor is a metal oxide.

5. A device as claimed in claim 1, wherein the dye contains a phosphonate or carboxyl group.

6. A device as claimed in claim 1, wherein the dye is a metal complex.

7. A device as claimed in claim 1, wherein the dye is a complex of Ru, Rh or Os.

8. A device as claimed in claim 1, wherein the dye contains at least one oligopyridyl ligand.

9. The device as claimed in claim 1, wherein the dye comprises a chemiluminescent, fluorescent or phosphorescent substance.

10. The device as claimed in claim 1, wherein the hole conductor material used is one or more spiro compounds of the formula (III)

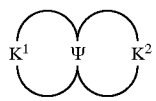

where ψ is C, Si, Ge or Sn, and $K^1$ and $K^2$, independently of one another, denote conjugated systems.

11. The device as claimed in claim 1, wherein the semiconductor layer has a roughness factor of >10.

12. The device as claimed in claim 4, wherein the semiconductor layer has a roughness factor of >100 and the semiconductor metal is titanium oxide.

13. The device as claimed in claim 10, wherein ψ is C or Si.

14. The device as claimed in claim 10, wherein ψ is C.

15. A device as claimed in claim 1, which comprises, as hole conductor material, one or more 9,9'-spirobifluorene derivatives of the formula (I):

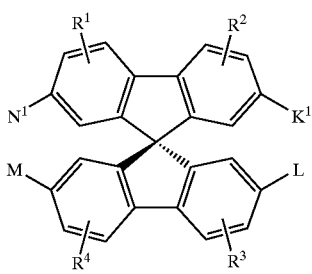

where the symbols have the following meanings:
$K^1$, L, M, $N^1$, $R^1$, $R^2$, $R^3$ and $R^4$ are identical or different and are
a) hydrogen, —$NO_2$—, —CN, —F or —Cl,
b) a straight-chain or branched alkyl radical having 1 to 20 carbon atom,
where
b1) one or more non-adjacent $CH_2$ groups is optionally replaced by —O—, —S—, —CO—O—, —O—CO—, —O—CO—O—, NR5 or —Si$(CH_3)_2$—,
b2) one or more $CH_2$ groups is optionally replaced by —CH=CH—, —C≡C—, 1,4-phenylene, 1,4-cyclohexylene or 1,3-cyclopentylene, or
b3) one or more H atoms may be replace by F or Cl, or b4) a combination of b1) to b3),
c) one of the following groups:

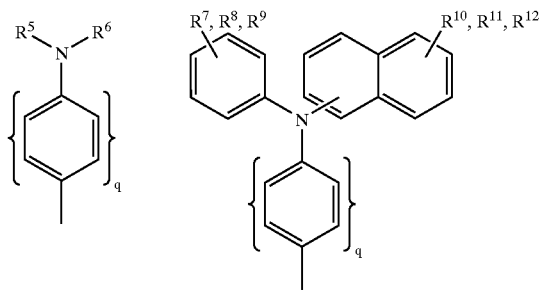

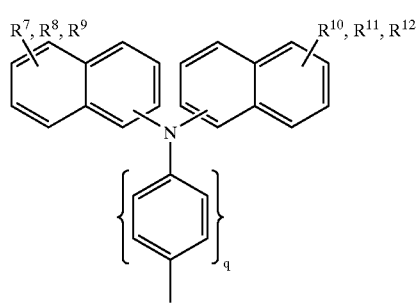

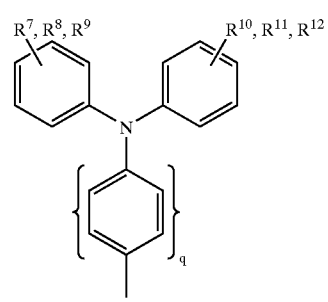

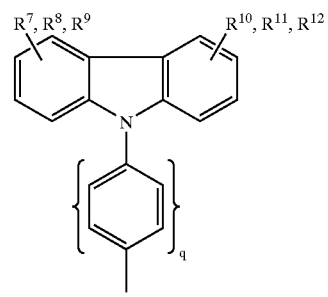

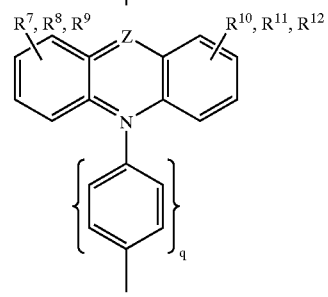

where q=0, 1, 2, 3, 4, 5 or 6

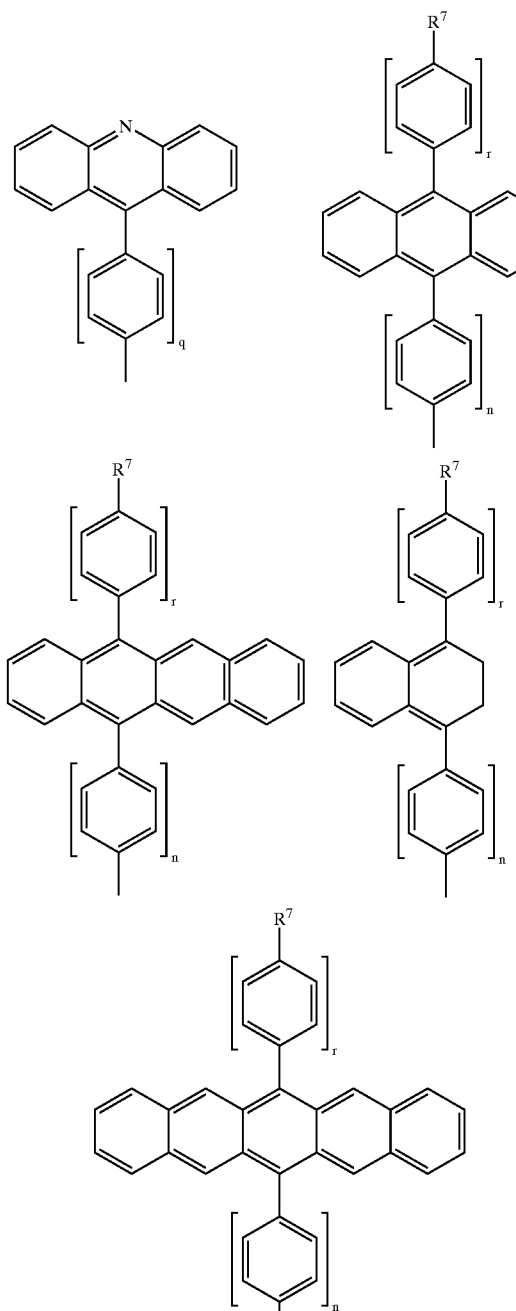

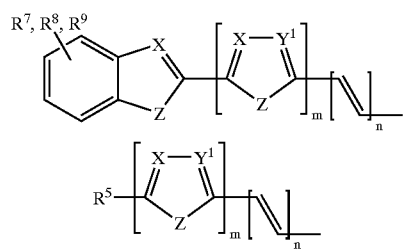

or
d) one of the following groups:

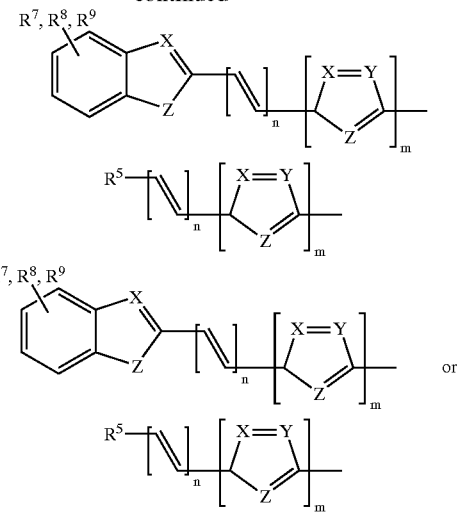

with the proviso that at least one of the radicals $K^1$, L, M, $N^1$, $R^1$, $R^2$, $R^3$ and $R^4$ is one of the groups listed under c);

X and $Y^1$ are independently of one another, $=CR^7-$ or $=N-$;

Z is $-O-$, $-S-$, $-NR^5-$, $-CRR-$, $-CR=CR-$ or $-CR=N-$;

$R^5$ and $R^6$ are, independently of one another,
a) hydrogen,
b) a straight-chain or branched alkyl radical having 1 to 20 carbon atoms,
where
b1) one or more non-adjacent $CH_2$ groups which are not bonded to nitrogen are optionally replaced by $-O-$, $-S-$, $-CO-O-$, $-O-CO-$, $-O-CO-O-$ or $-Si(CH_3)_2-$,
b2) one or more $CH_2$ groups optionally replaced by $-CH=CH-$, $-C\equiv C-$, cyclopropane-1,2-diyl, 1,4-phenylene, 1,4-cyclohexylene or 1,3-cyclopentylene,
b3) one or more H atoms optionally replaced by F or Cl,
b4) $R^5$ and $R^6$ together form a ring, or
b5) a combination of b1) to b4),
c) phenyl, biphenyl, 1-naphthyl, 2-naphthyl, 2-thienyl or 2-furanyl;

$R^7$, $R^8$, $R^9$, $R^{10}$, $R^{11}$ and $R^{12}$ are, independently of one another,
a) hydrogen, $-CN$, $-F$, $-NO_2$ or $-Cl$
b) a straight-chain or branched alkyl radical having 1 to 20 carbon atoms, where
b1) one or more non-adjacent $CH_2$ groups is optionally replaced by $-O-$, $-S-$, $-CO-O-$, $-O-CO-$, $-O-CO-O-$, $-NR^5-$ or $-Si(CH_3)_2-$,
b2) one or more $CH_2$ groups is optionally replaced by $-CH=CH-$, $-C\equiv C-$, cyclopropane-1,2-diyl, 1,4-phenylene, 1,4-cyclohexylene or 1,3-cyclopentylene, b3) one or more H atoms is optionally replaced by F or Cl; or b4) a combination of b1) to b3), c) phenyl, biphenyl, 1-naphthyl, 2-naphthyl, 2-thienyl, 2-furanyl, —O-phenyl, —O-biphenyl, —O-1-naphthyl, —O-2-naphthyl, —O-2-thienyl or —O-2-furanyl, m, n, q and r are, independently of one another, an integer from 0 to 6.

16. A method of detecting electromagnetic radiation which comprises determining the intensity of electromagnetic radiation using the device as claimed in claim 1.

17. The device as claimed in claim 1, wherein the dynamic band width has been matched by the measurement of the photovoltage.

18. The device as claimed in claim 1, wherein said dye is excited by the electromagnetic radiation of a wavelength between 400 nm and 1000 nm, and said semiconductor having a high band gap above 3 eV and said hole conductor material is an amorphous material.

19. The device as claimed in claim 20, wherein said dye is a photochromic dye, said semiconductor is a metal oxide and said hole conductor material is soluble in organic solvents.

20. The device as claimed in claim 1, wherein the hole conductor material used is one or more 9,9'-spirobifluorene derivatives of the formula (IV)

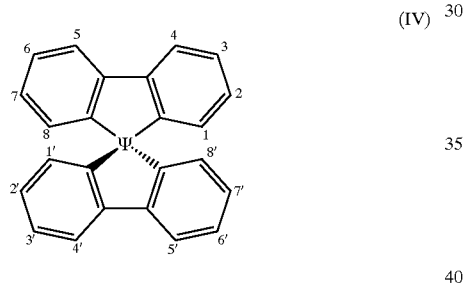

(IV)

where ψ is C, Si, or Sn and the benzo groups are optionally, independently of one another are substituted, wherein the substituents are a) H, —NO$_2$—, —CN, —F or —Cl, b) a straight-chain or branched alkyl radical having 1 to 20 carbon atom wherein one or more non-adjacent CH$_2$ groups are optionally replaced by —O—, —S—, —CO—O—, —O—CO—, —O—CO—O—, NR$^5$, —Si(CH$_3$)$_2$—, —CH=CH—, —C C—, 1,4-phenylene, 1,4-clohexylene or 1,3-cyclopentylene, and optionally one or more H atoms are replaced by F, Cl, c) a group of the following groups:

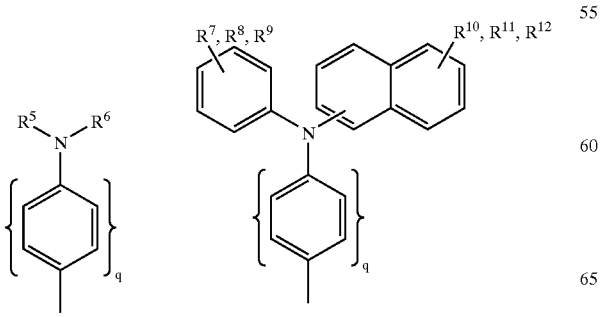

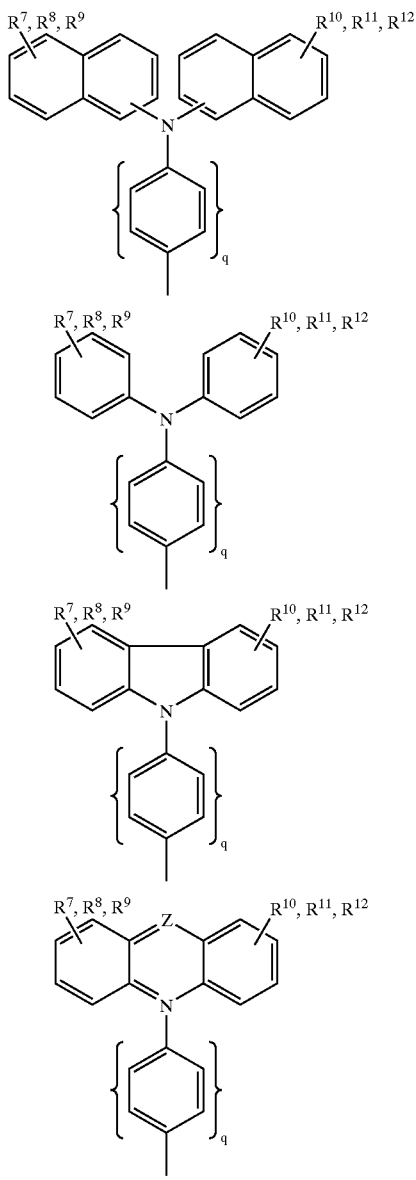

where q=0, 1, 2, 3, 4, 5 or 6

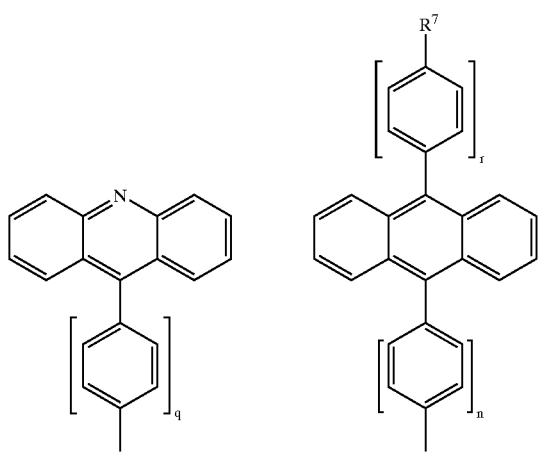

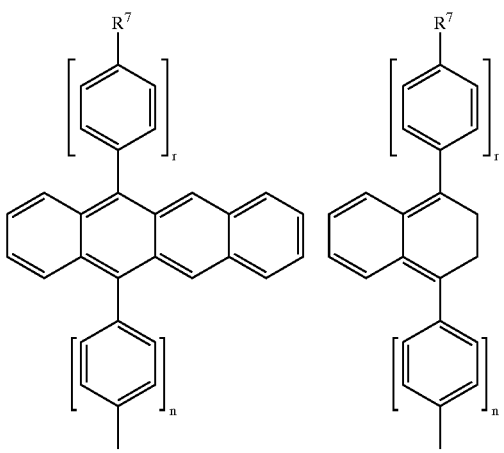

or

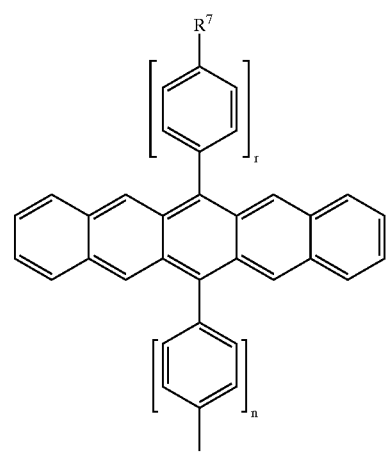

or d) one of the following groups:

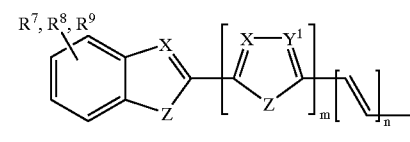

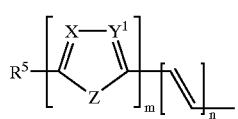

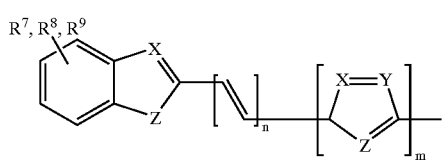

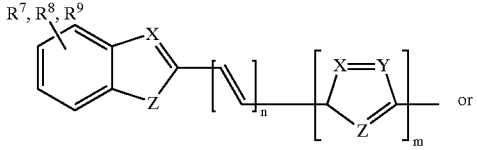

or

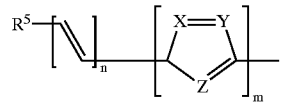

with the proviso that at least one of the radicals $K^1$, L, M, $N^1$, $R^1$, $R^2$, $R^3$ and $R^4$ is one of the groups listed undec c);

X and $Y^1$ are independently of one another, =$CR^7$— or =N—;

Z is —O—, —S—, —$NR^5$—, —CRR—, —CR=CR— or —CR=N—;

$R^5$ and $R^6$ are, independently of one another,
  a) hydrogen,
  b) a straight-chain or branched alkyl radical having 1 to 20 carbon atoms,
    where
    b1) one or more non-adjacent $CH_2$ groups which are not bonded to nitrogen are optionally replaced by —O—, —S—, —CO—O—, —O—CO—, —O—CO—O— or —Si($CH_3$)$_2$,
    b2) one or more $CH_2$ groups optionally replaced by —CH=CH—, —C C—, cyclopropane-1,2-diyl, 1,4-phenylene, 1,4-cyclohexylene or 1,3-cyclopentylene,
    b3) one or more H atoms optionally replaced by F or Cl,
    b4) $R^5$ and $R^6$ together form a ring, or
    b5) a combination of b1) to b4),
  c) phenyl, biphenyl, 1-naphthyl, 2-naphthyl, 2-thienyl or 2-furanyl;

$R^7$, $R^8$, $R^9$, $R^{10}$, $R^{11}$ and $R^{12}$ are, independently of one another,
  a) hydrogen, —CN, —F, —$NO_2$ or —Cl
  b) a straight-chain or branched alkyl radical having 1 to 20 carbon atoms, where
    b1) one or more non-adjacent $CH_2$ groups is optionally replaced by —O—, —S—, —CO—O—, —O—CO—, —O—CO—O—, —$NR^5$— or —Si($CH_3$)$_2$—,
    b2) one or more $CH_2$ groups is optionally replaced by —CH=CH—, —C C—, cyclopropane-1,2-diyl, 1,4-phenylene, 1,4-cyclohexylene or 1,3-cyclopentylene,
    b3) one or more H atoms is optionally replaced by F or Cl; or
    b4) a combination of b1) to b3),
  c) phenyl, biphenyl, 1-naphthyl, 2-naphthyl, 2-thienyl, 2-furanyl, —O-phenyl, —O-biphenyl, —O-1-naphthyl, —O-2-naphthyl, —O-2-thienyl or —O-2-furanyl, m, n, q and r are, independently of one another, an integer from 0 to 6.
21. A device as claimed in claim 1, wherein the device comprises, as hole conductor material, one or more 9,9'-spirobifluorene derivatives of the formula (II):
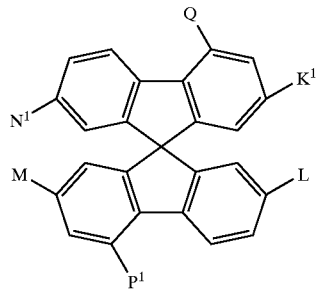
(II)
where the symbols have the following meanings:
K$^1$, L, M, and N$^1$ are identical or different and are
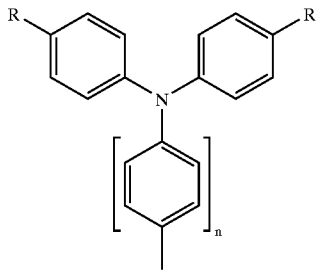
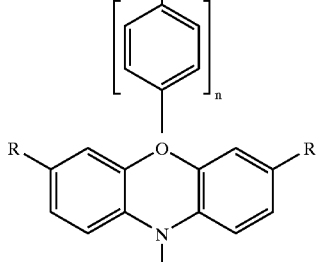
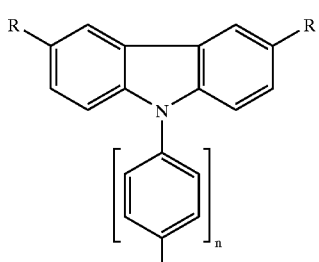
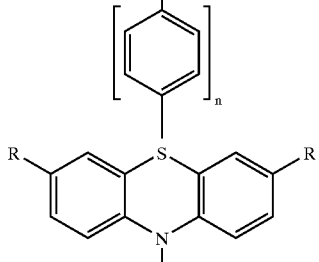
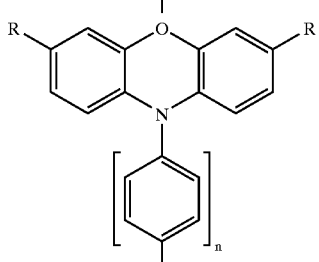
-continued
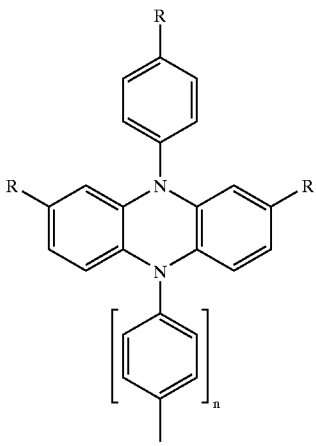
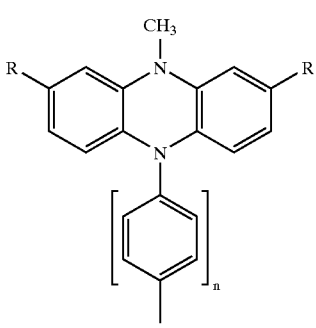
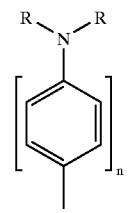
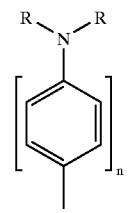

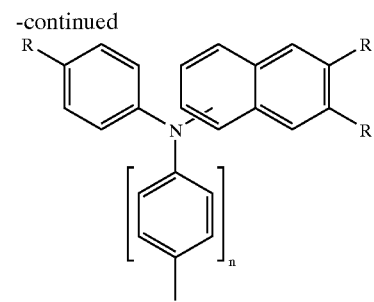

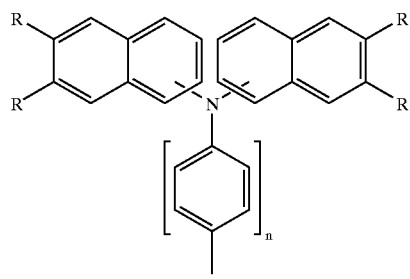

n = 0, 1, 2, 3, 4, 5, or 6

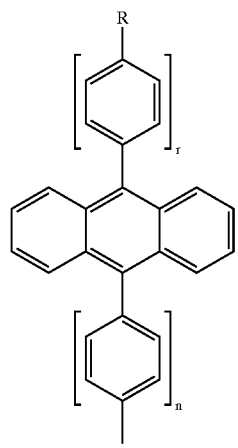

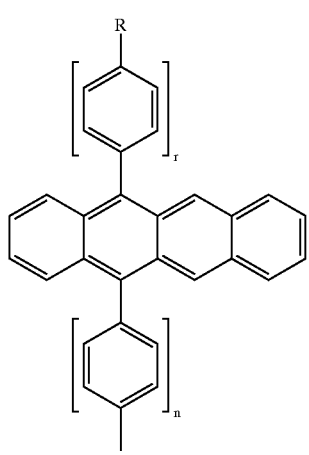

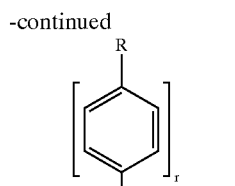

or

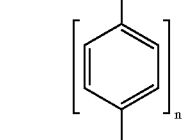

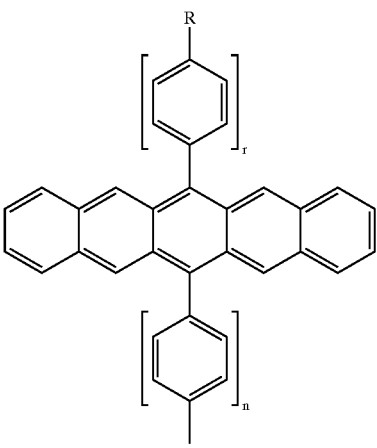

R are identical or different and are H, alkyl, —O-alkyl, —S-alkyl, in each case having 1 to 20 carbon atoms, phenyl, biphenyl, 1-naphthyl, 2-naphthyl, 2-thienyl, 2-furanyl, —O-phenyl, —O-biphenyl, —O-1-naphthyl, —O-2-naphthyl, —O-2-thienyl, —O-2-furanyl, —CN or —NR$_2$, where —O-alkyl/aryl, —S-alkyl/aryl, —CN and —NR$_2$ cannot be bonded to nitrogen;

n is an integer from 0 to 4, and Q and P$^1$ are, independently of one another, and are

H, COOR, CH$_2$OR,

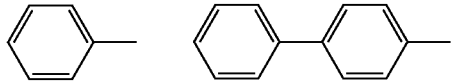

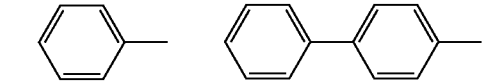

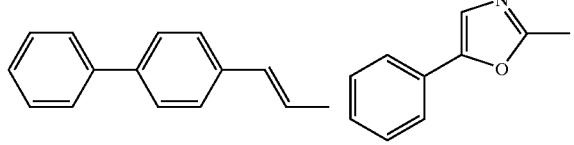

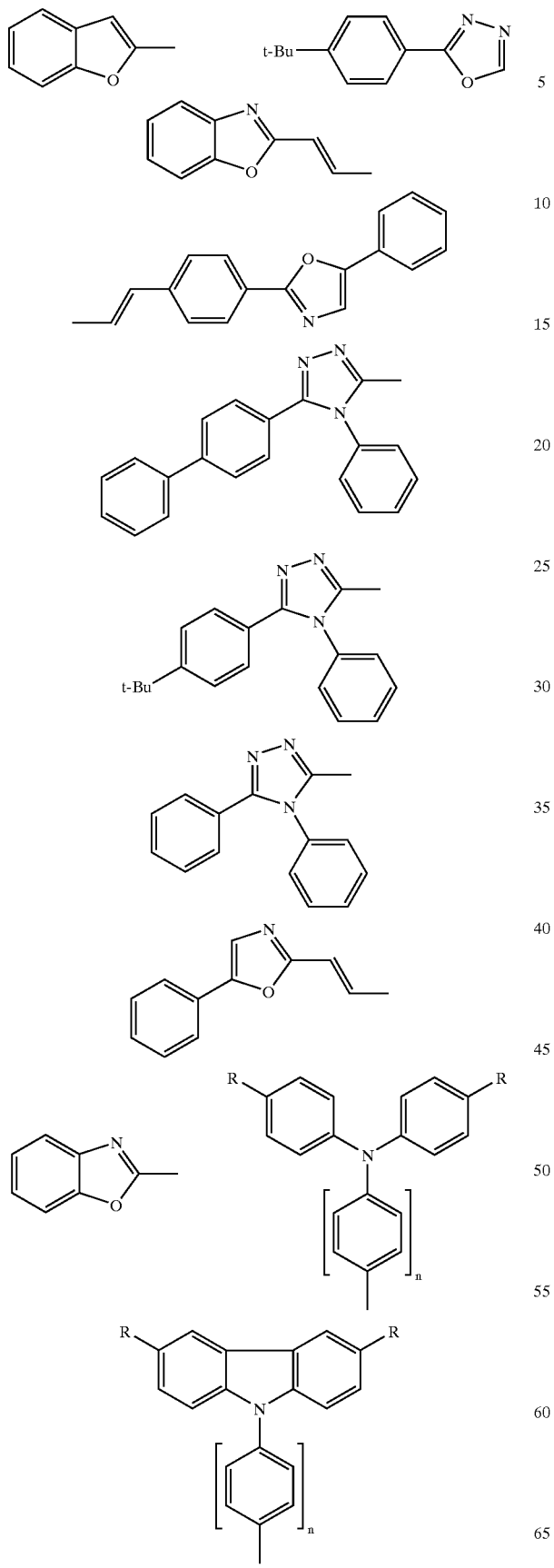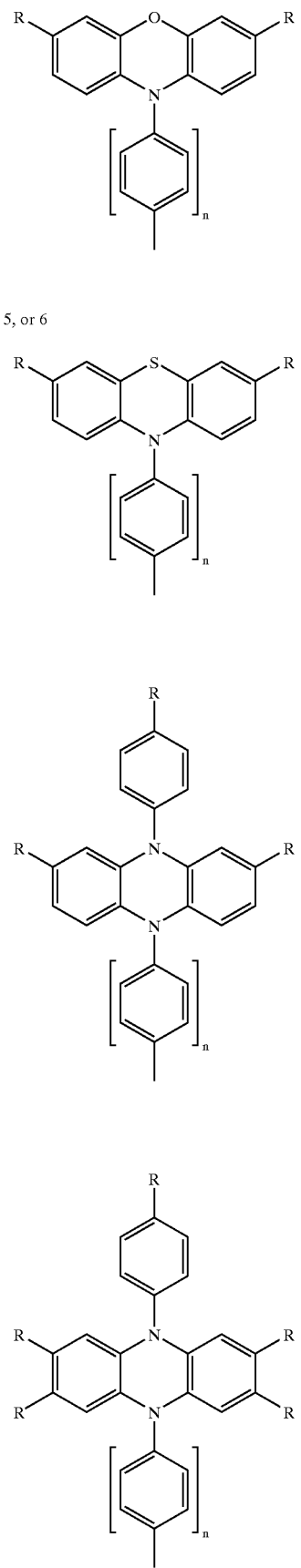
n = 0, 1, 2, 3, 4, 5, or 6

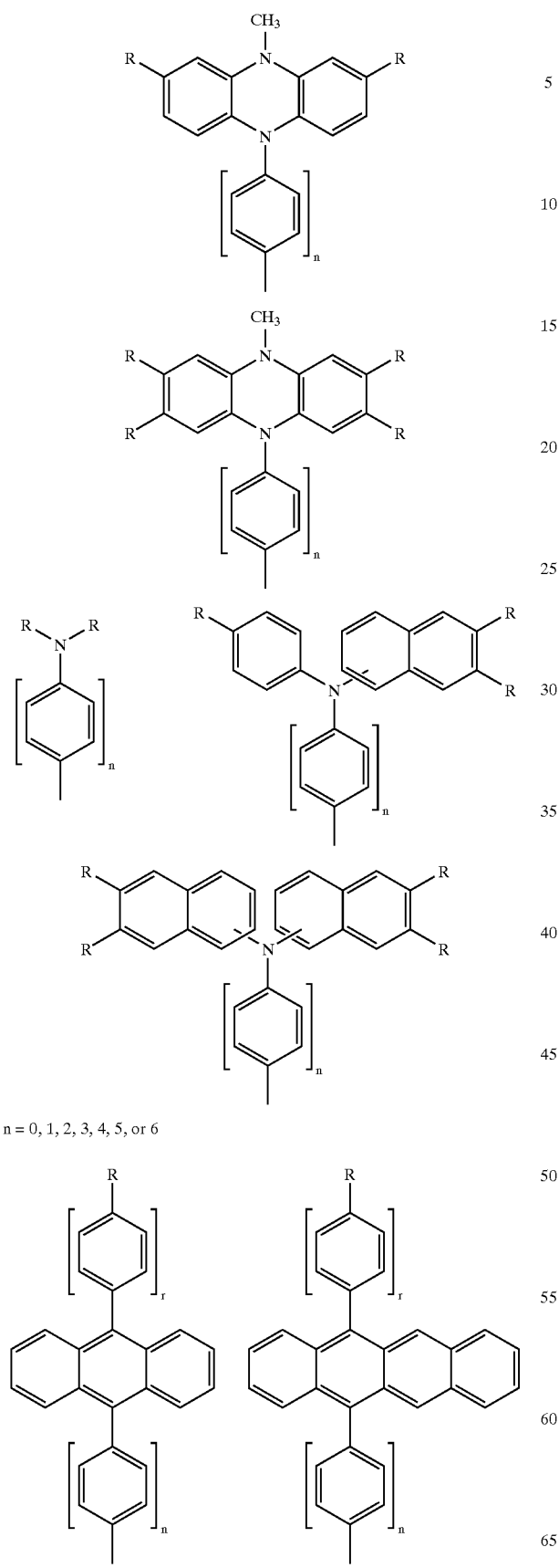
n = 0, 1, 2, 3, 4, 5, or 6
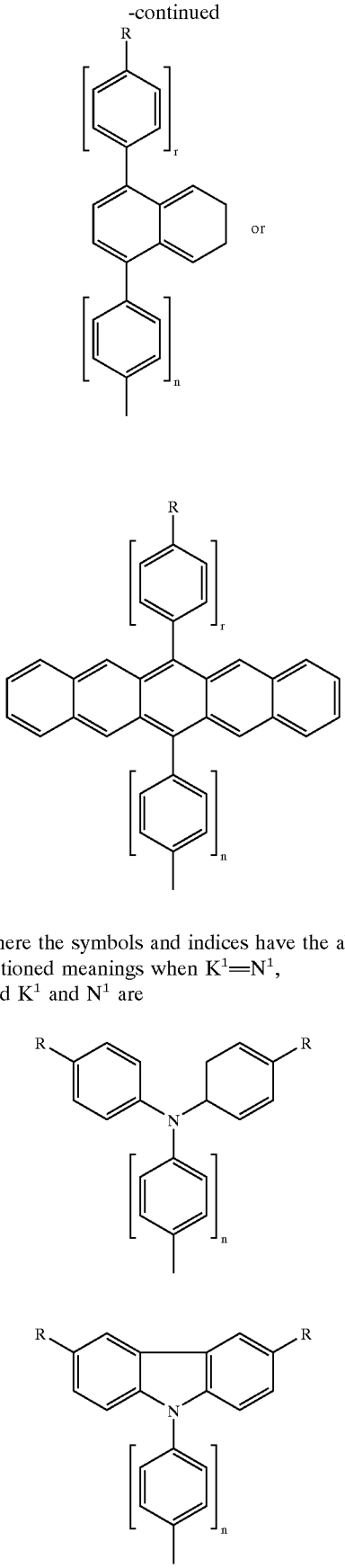
where the symbols and indices have the abovementioned meanings when $K^1 = N^1$, and $K^1$ and $N^1$ are
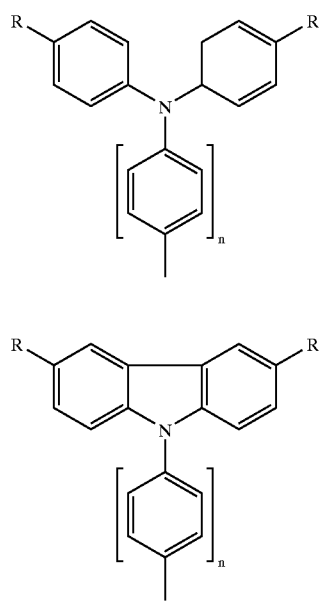

-continued
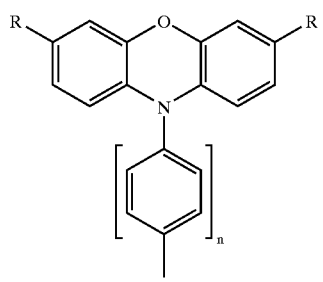
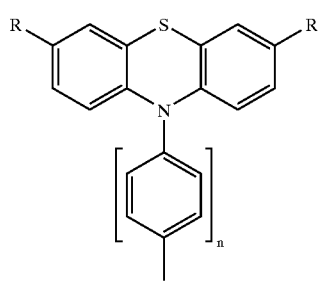
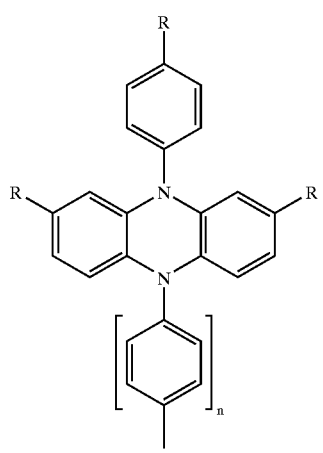
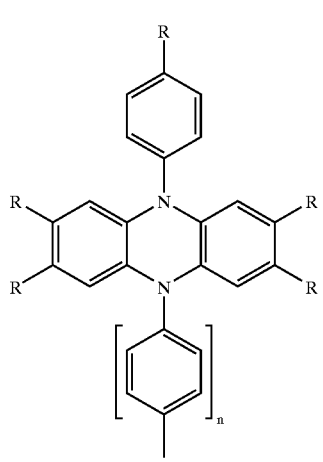
-continued
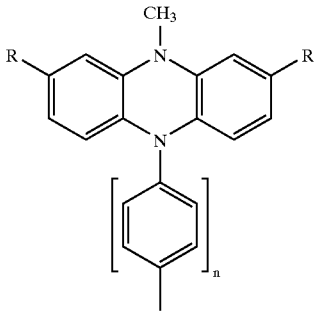
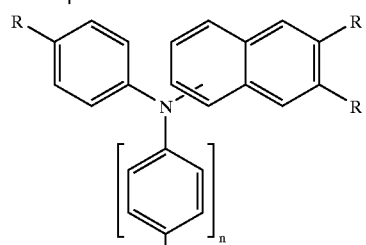
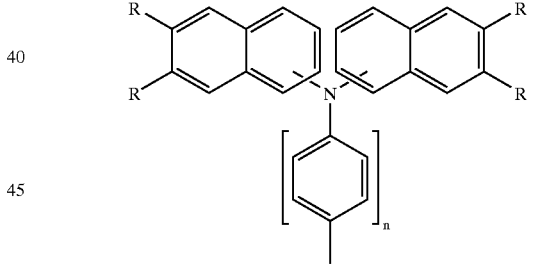
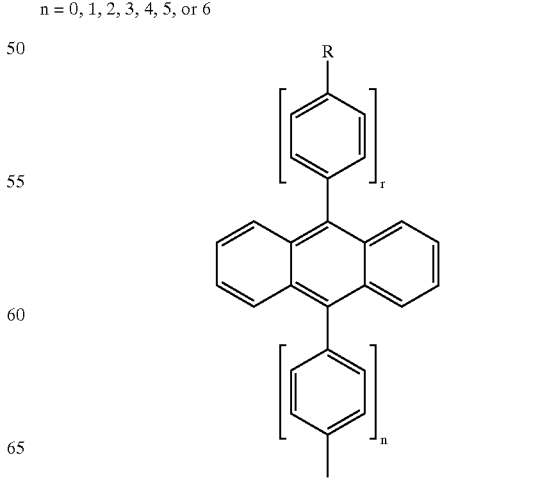
n = 0, 1, 2, 3, 4, 5, or 6

-continued
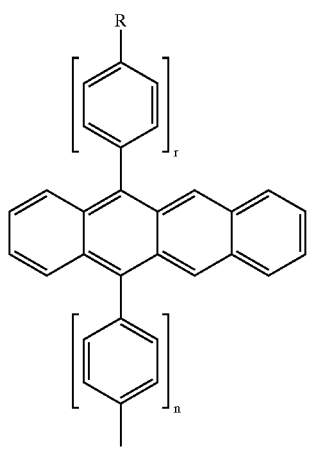
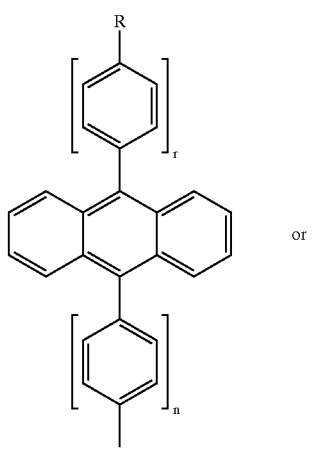 or
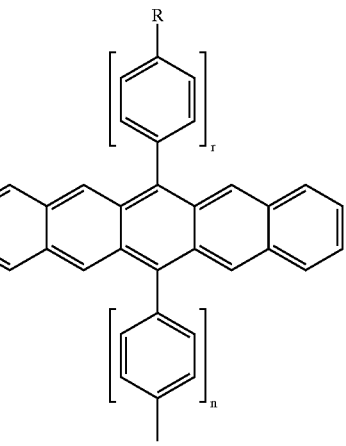
and when L=M, L and M are
H, COOR, CH₂OR,
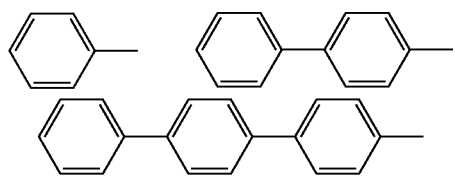
-continued
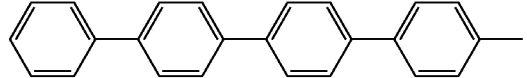
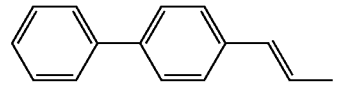
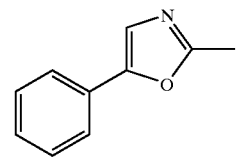
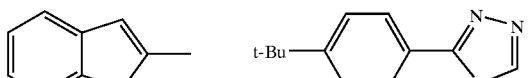
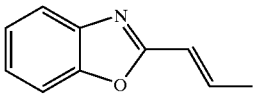
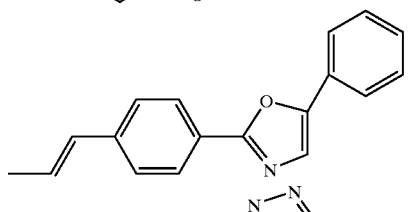
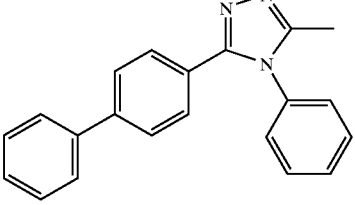
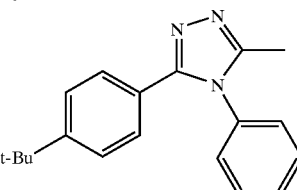
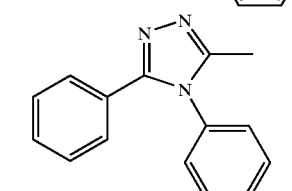
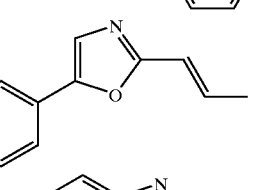 or
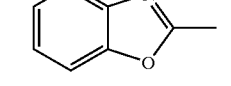

and Q and P¹, independently of one another, are
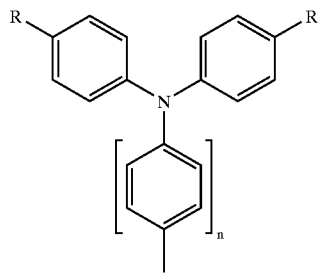
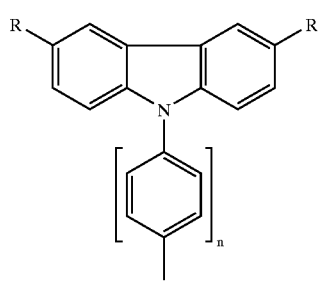
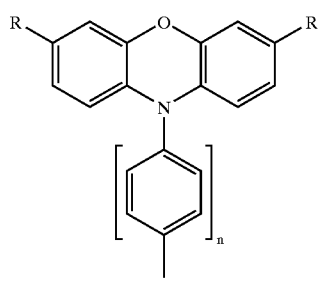
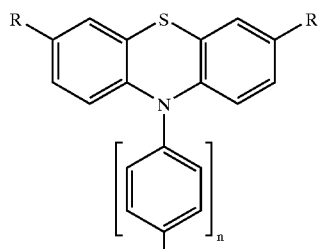
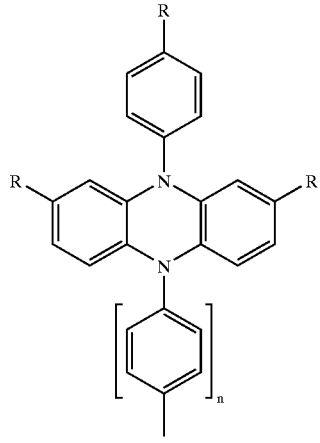
-continued
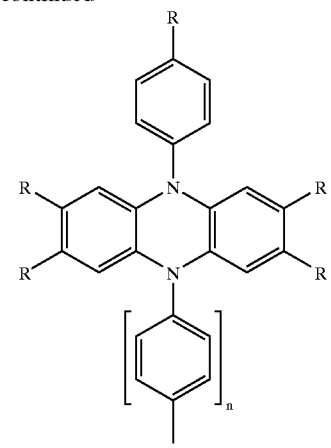
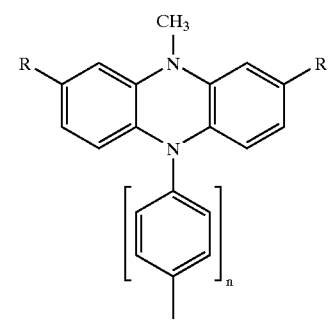
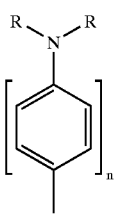
n = 0, 1, 2, 3, 4, 5, or 6

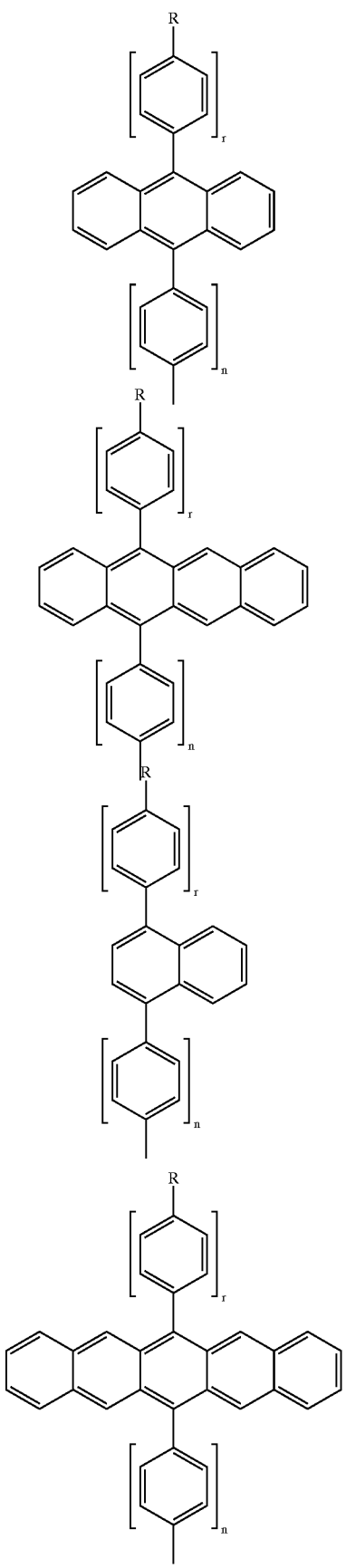
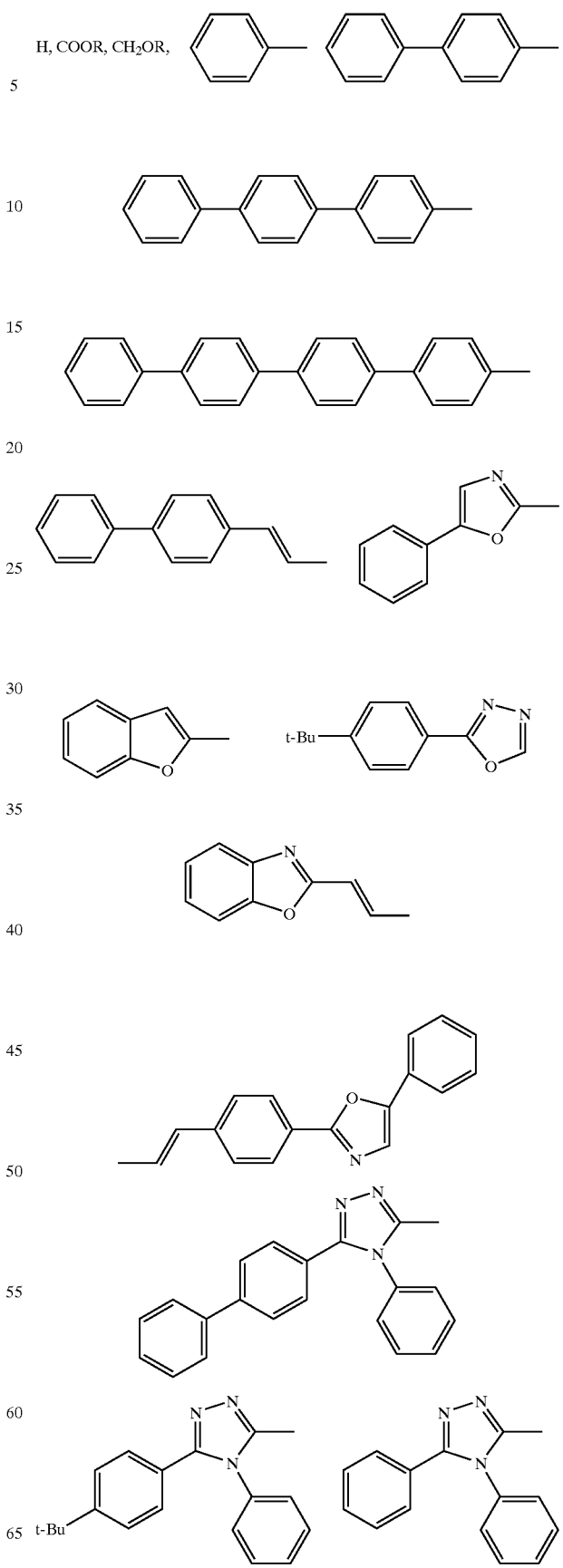

-continued
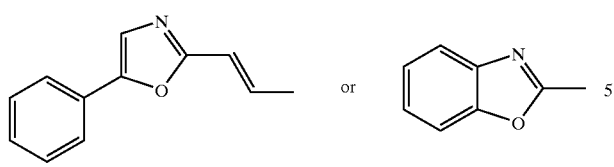
where the symbols and indices have the above-mentioned meanings,
when $K^1=M$, $K^1$ and M are
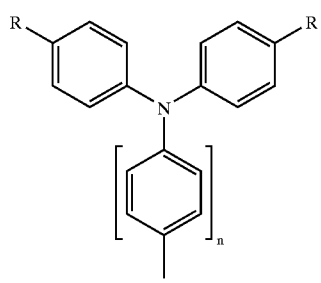
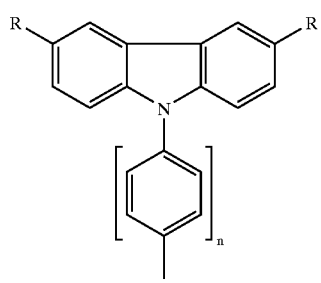
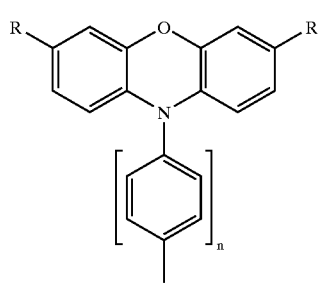
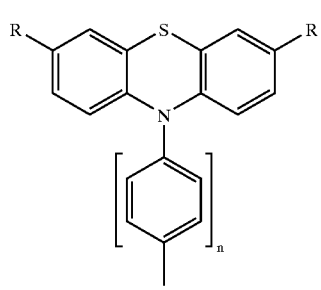
-continued
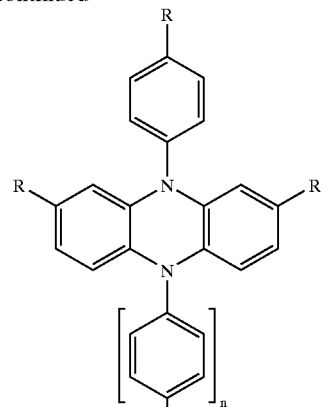
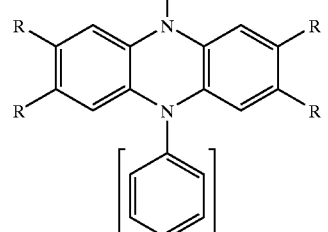
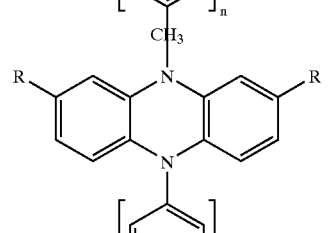
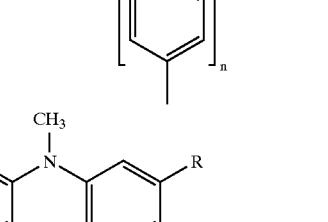
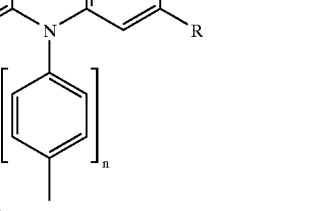 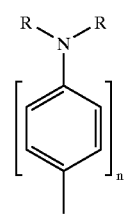
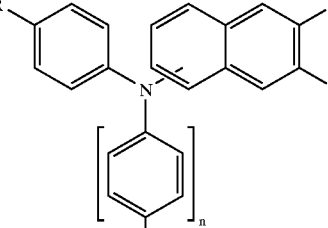

-continued
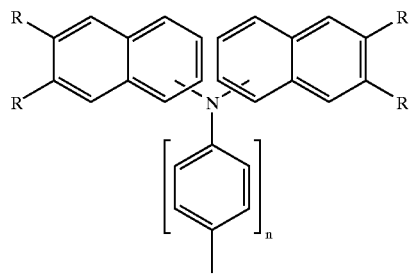
n = 0, 1, 2, 3, 4, 5, or 6
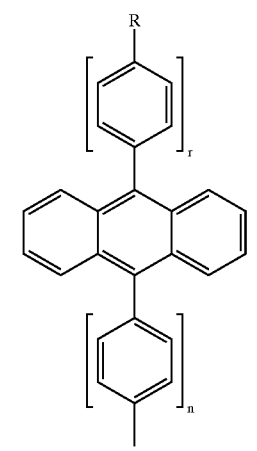
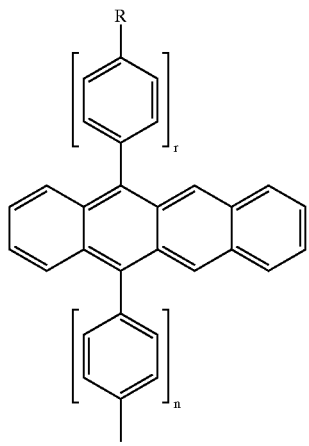
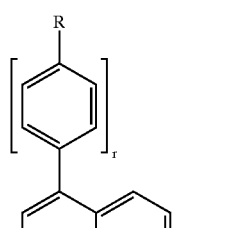
or
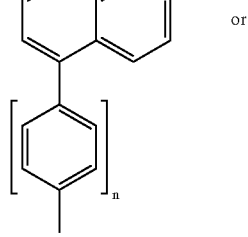
-continued
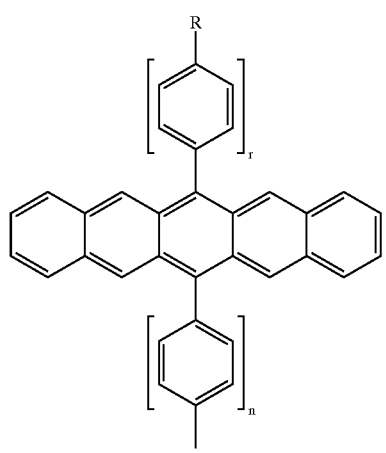
and when M=N¹, M and N¹ are
H, COOR, $CH_2OR_1$
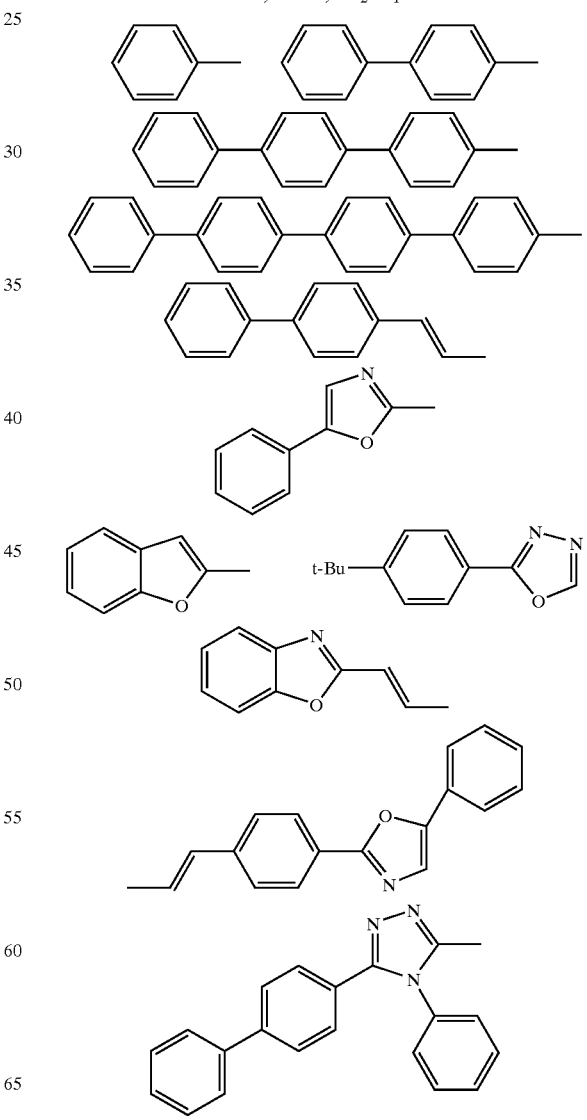

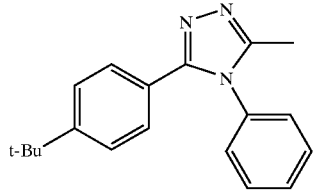
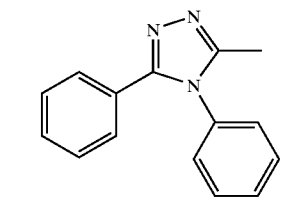
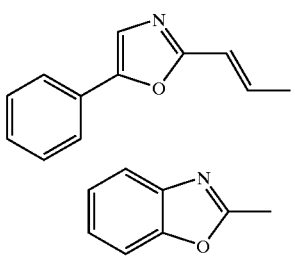 or 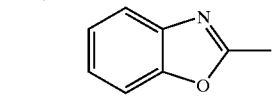
and Q and P¹ independently of one another, are
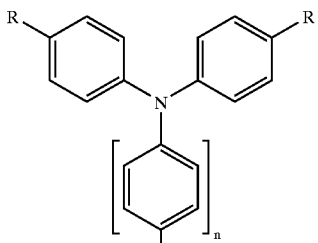
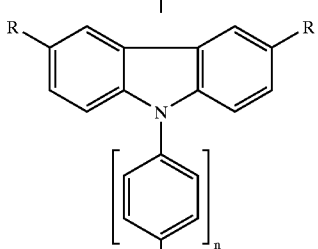
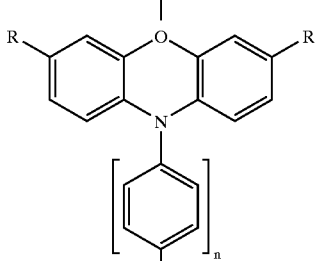
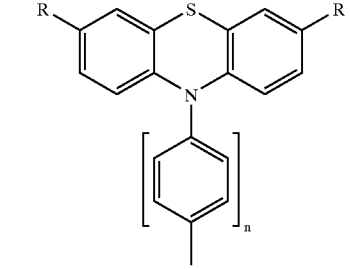
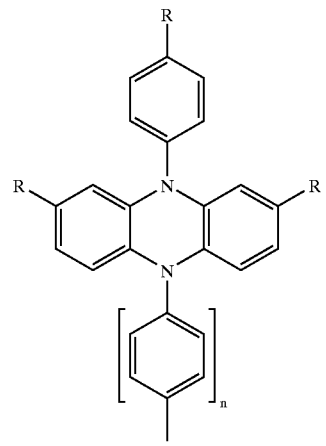
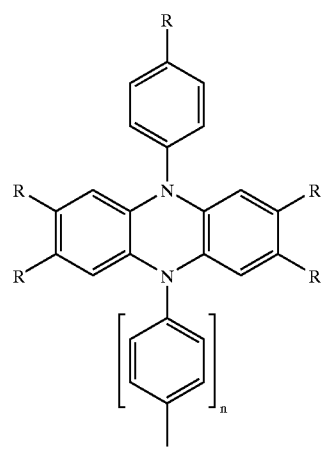
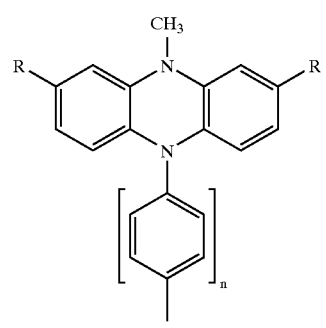

-continued
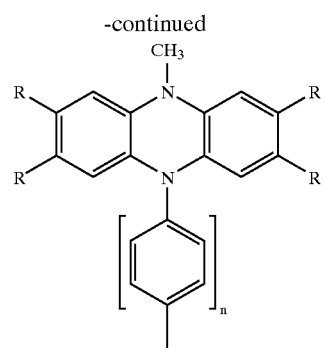
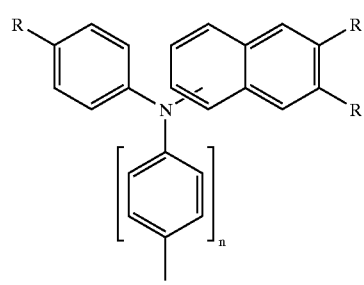
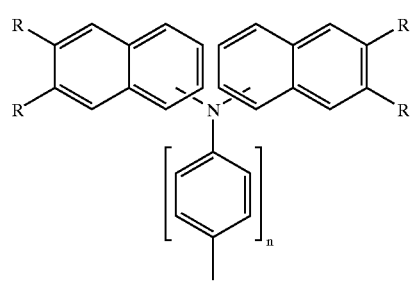
n = 0, 1, 2, 3, 4, 5, or 6
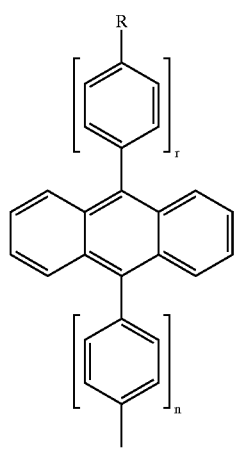
-continued
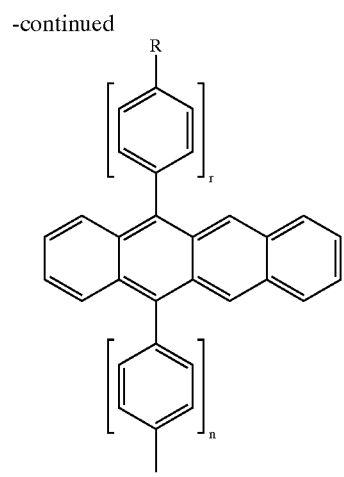
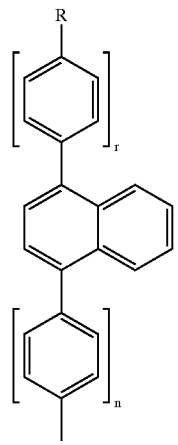
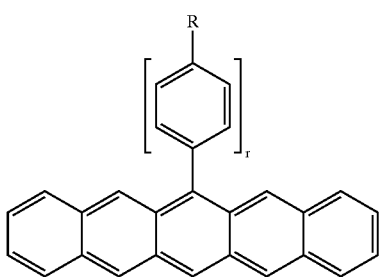
H, COOR, CH$_2$OR, 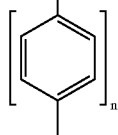
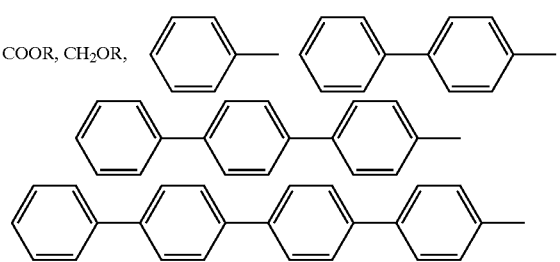

-continued

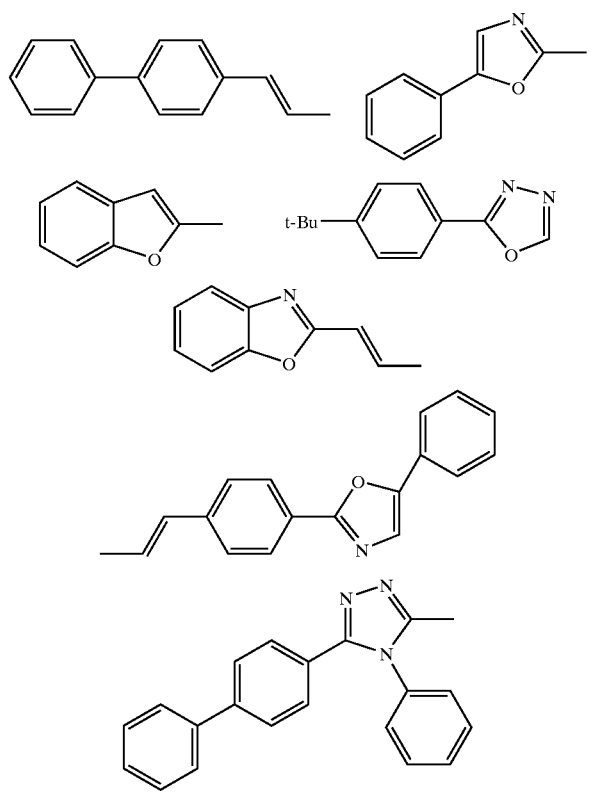

-continued

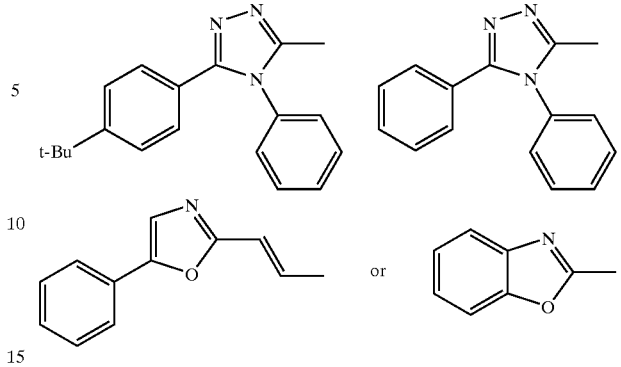

in which the symbols and indices have the abovementioned meanings.

22. A selective chemical analysis system comprising the device as claimed in claim 1 and a molecular detection system which is read out via electromagnetic radiation wherein the chemical analysis system is environmental analysis system, biomolecular analysis system or diagnostic analysis system.

23. A selective chemical analysis system comprising the device as claimed in claim 1 and a molecular detection system which is read out via electromagnetic radiation wherein the chemical analysis system is an immuno diagnostic system, gene diagnostic system or a combinatorial analysis system.

24. The device as claimed in claim 15, wherein m, n, q and r are independently of one another 0, 1, 2 or 3.

* * * * *

UNITED STATES PATENT AND TRADEMARK OFFICE
CERTIFICATE OF CORRECTION

PATENT NO. : 6,664,071 B1
DATED : December 16, 2003
INVENTOR(S) : Norbert Windhab et al.

It is certified that error appears in the above-identified patent and that said Letters Patent is hereby corrected as shown below:

<u>Column 54,</u>
Line 17, "undec c)" should read -- under c) --.

Signed and Sealed this

Sixteenth Day of March, 2004

JON W. DUDAS
*Acting Director of the United States Patent and Trademark Office*